United States Patent
Greco et al.

[11] Patent Number: 5,888,971
[45] Date of Patent: Mar. 30, 1999

[54] MACROCYCLIC PEPTIDES USEFUL IN THE TREATMENT OF THROMBIN RELATED DISORDERS

[75] Inventors: Michael N. Greco, Lansdale; Bruce E. Maryanoff, Forest Grove, both of Pa.

[73] Assignee: Ortho Pharmaceutical Corporation, Inc., Raritan, N.J.

[21] Appl. No.: 603,666

[22] Filed: Feb. 20, 1996

[51] Int. Cl.[6] .............................. C07K 7/56; A61K 38/12

[52] U.S. Cl. .................................. 514/9; 514/10; 514/11; 514/18; 530/317; 530/330; 530/331

[58] Field of Search ...................... 530/317, 330, 530/331; 514/9, 10, 11, 18

[56] References Cited

PUBLICATIONS

Greco et al, Bioorganic Medicinal Chemistry Letters (1996) 6 (24) 1996.

*Primary Examiner*—Robert Gerstl

[57] ABSTRACT

Compounds of Formula I

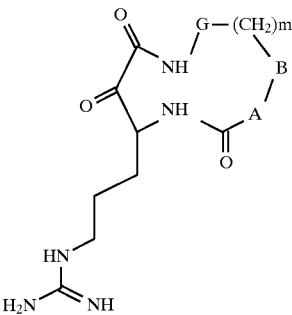

and Formula III

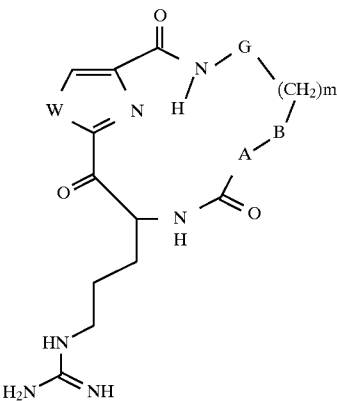

which are useful in the treatment of thrombin and trypsin related disorders.

53 Claims, No Drawings

MACROCYCLIC PEPTIDES USEFUL IN THE TREATMENT OF THROMBIN RELATED DISORDERS

This invention relates a series of macrocyclic peptides, intermediates used in their manufacture and pharmaceutical compositions containing them. The compounds are inhibitors of serine proteases, particularly α-thrombin and may be used in a variety of thrombin related disorders such as venous thrombosis and arterial thrombosis.

BACKGROUND OF THE INVENTION

With a rapidly aging population, diseases of the vascular system are of great concern to our society. Arterial thrombosis is the major cause of death in the form of heart attacks and strokes, while venous thrombosis is associated with pulmonary embolism which occurs after surgery or extended periods of inactivity.

Thrombin is a multifunctional serine protease whose role in thrombosis and hemostasis has been documented by a number of sources (See generally, Tapparelli, et al. *TiPS* 1993, 14, 366–76). Thrombin acts as a procoagulant through proteolytic cleavage of fibrinogen to form fibrin and as an anticoagulant through activation of the protein C pathway (followed by inactivation of coagulation factors V and VIII.)

The concentration of active thrombin is limited by a number of feedback mechanisms involving endogenous factors and proteins. In addition to protein C, antithrombin III is another regulating protein which forms a complex with endogenous heparin. This complex binds to active thrombin, thus inactivating it.

Current anticoagulant therapy consists of three classes of compounds: heparins, coumarins and low molecular weight heparins. These drugs act indirectly to limit the concentration of active thrombin. Heparins and low molecular weight heparins interact with antithrombin III and the coumarins inhibit a number of vitamin K dependent coagulation factors. Although these drugs are prescribed for diseases associated with venous thrombosis and arterial thrombosis, their use is limited. They have a number of side effects, a slow onset of action and only the coumarins are orally active (warfarin and dicumarol).

Indirect thrombin inhibitors have been shown to be less effective at controlling associated diseases than direct thrombin inhibitors. Thus the search for orally active direct thrombin inhibitors is underway in a number of laboratories. These efforts have produced a number of acyclic peptidyl compounds which directly inhibit thrombin. PPACK, argatroban, (D)-NAPAP, hirulog-1 and DUP 714 are examples of these inhibitors. Many of these compounds lack useful oral activity, and many have a poor selectivity for thrombin versus other serine proteases. Therefore, a need remains for new direct thrombin inhibitors.

When compared to acyclic peptides, cyclic peptides have a number of structural features that have been linked to changes in the biological activity of simple peptides. Due to the absence of polar end groups and a relatively rigid structure, cyclic peptides are hypothesized to be more membrane permeable and less susceptible to peptidases. Potentially one could incorporate the structure of simple peptides, within rigid, non-polar macrocyclic framework, to produce active bioavailable compounds.

Cyclotheonamide A (CtA) is a cyclic peptide which was isolated from *Theonella.sp*, a marine sponge. It inhibits a variety of serine proteases particularly thrombin and trypsin.

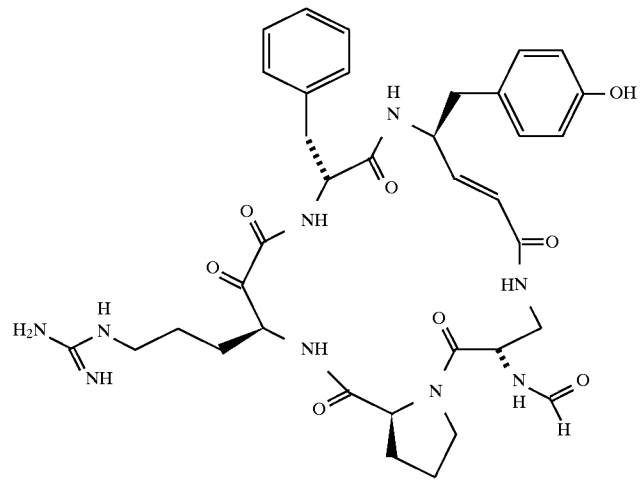

cyclotheonamide A (CtA)

Although this molecule inhibits thrombin (Ki# ca. 1–2 nM), it is a scarce natural product which is difficult to extract from its natural source. In addition, CtA is not an optimal candidate for treating thrombin-related disorders as its selectivity for thrombin over trypsin does not favor thrombin. The invention described below claims a novel macrocyclic peptides that inhibit thrombin at nanomolar levels and exhibit reasonable selectivity for thrombin over trypsin.

The invention relates to new compounds of the Formula I

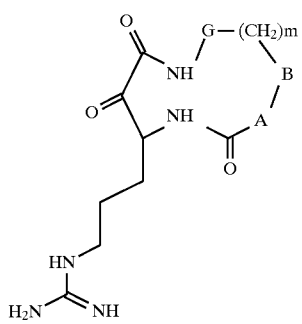

wherein:

m is 2 to 12;

A is

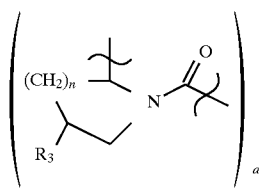

where the amido carbonyl is bound to B and the α aminomethine is bound to the depicted ring carbonyl, $R_3$ is hydrogen, hydroxy or $C_{1-5}$alkoxy, n is 1 or 2 and a is 0 or 1;

B is

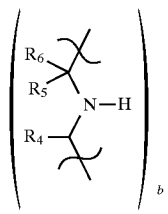

where the amido carbonyl of B is bound to the depicted ring methylenes and the methine is bound to A, $R_4$ is selected from the group consisting of any of hydrogen, $C_{1-5}$alkyl, carboxy $C_{1-5}$alkyl, phenyl, substituted phenyl (where the phenyl substituents are $C_{1-5}$alkyl, carboxy $C_{1-5}$alkoxycarbonyl, carboxamido, amino, $C_{1-5}$alkylamino, hydroxy, $C_{1-5}$alkylcarbonylamino, $C_{1-5}$alkoxy, fluorine, bromine or chlorine), phenyl$C_{1-5}$alkyl, substituted phenyl$C_{1-5}$alkyl (where the phenyl substituents are $C_{1-5}$alkyl, carboxy $C_{1-5}$alkoxycarbonyl, carboxamido, amino, $C_{1-5}$alkylamino, hydroxy, $C_{1-5}$alkylcarbonylamino, $C_{1-5}$alkoxy, fluorine bromine or chlorine), 3-pyridyl$C_{1-5}$alkyl, 4-pyridyl$C_{1-5}$alkyl, diphenyl$C_{1-2}$alkyl, naphthyl or substituted naphthyl (where the naphthyl substituents are $C_{1-5}$alkyl, carboxy $C_{1-5}$alkoxycarbonyl, carboxamido, amino, $C_{1-5}$alkylamino, hydroxy, $C_{1-5}$alkylcarbonylamino, $C_{1-5}$alkoxy, fluorine bromine or chlorine), $R_5$ and $R_6$ are each hydrogen or taken together with the carbon to which each is attached to form a carbonyl, and b is 0 or 1;

G is

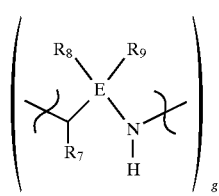

where the amine of G is bound to the ring methylenes and the methine is bound to the depicted amide, $R_7$ is independently selected from the group consisting of hydrogen, $C_{1-5}$alkyl, carboxy$C_{1-5}$alkyl, phenyl, substituted phenyl (where the phenyl substituents are $C_{1-5}$alkyl, carboxy $C_{1-5}$alkoxycarbonyl, carboxamido, amino, $C_{1-5}$alkylamino, hydroxy, $C_{1-5}$alkylcarbonylamino, $C_{1-5}$alkoxy, fluorine bromine or chlorine), phenyl$C_{1-5}$alkyl, substituted phenyl$C_{1-5}$alkyl (where the phenyl substituents are $C_{1-5}$alkyl, carboxy $C_{1-5}$alkoxycarbonyl, carboxamido, amino, $C_{1-5}$alkylamino, hydroxy, $C_{1-5}$alkylcarbonylamino, $C_{1-5}$alkoxy, fluorine bromine or chlorine), 3-pyridyl$C_{1-5}$alkyl, 4-pyridyl$C_{1-5}$alkyl, diphenyl$C_{1-2}$alkyl, and naphthyl, substituted naphthyl (where the naphthyl substituents are $C_{1-5}$alkyl, carboxy $C_{1-5}$alkoxycarbonyl, carboxamido, amino, $C_{1-5}$alkylamino, hydroxy, $C_{1-5}$alkylcarbonylamino, $C_{1-5}$alkoxy, fluorine bromine or chlorine), E is carbon or $C(CH_2)_q$—, where q is 0 to 12, with the proviso that the sum of q and m cannot exceed 24, $R_8$ and $R_9$ are hydrogen or taken together with the carbon of E to form a carbonyl, and g is 0 or 1;

and pharmaceutically acceptable salts thereof.

An additional aspect of the invention relates to novel compounds of the Formula II which are intermediates in the synthesis of compounds for the Formula I,

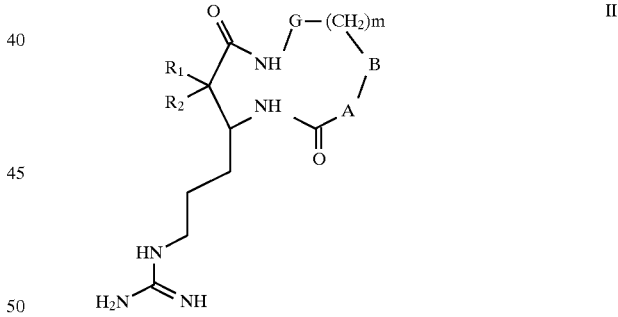

wherein:

$R_1$ is hydroxy;

$R_2$ is hydrogen;

m is 2 to 12;

A is

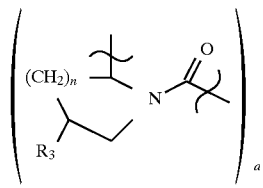

where the amido carbonyl is bound to B and the a aminomethine is bound to the depicted ring carbonyl, $R_3$ is hydrogen or $C_{1-5}$alkoxy,
n is 1 or 2, and
a is 0 or 1;
B is

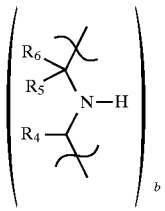

where the amido carbonyl of B is bound to the depicted ring methylenes and the methine is bound to A, $R_4$ is selected from the group consisting of hydrogen, $C_{1-5}$alkyl, carboxy$C_{1-5}$alkyl, phenyl, substituted phenyl (where the phenyl substituents are $C_{1-5}$alkyl, carboxy $C_{1-5}$alkoxycarbonyl, carboxamido, amino, $C_{1-5}$alkylamino, hydroxy, $C_{1-5}$alkylcarbonylamino, $C_{1-5}$alkoxy, fluorine bromine or chlorine), phenyl$C_{1-5}$alkyl, substituted phenyl$C_{1-5}$alkyl (where the phenyl substituents are $C_{1-5}$alkyl, carboxy $C_{1-5}$alkoxycarbonyl, carboxamido, amino, $C_{1-5}$alkylamino, hydroxy, $C_{1-5}$alkylcarbonylamino, $C_{1-5}$alkoxy, fluorine bromine or chlorine), 3-pyridyl$C_{1-5}$alkyl, 4-pyridyl$C_{1-5}$alkyl, diphenyl$C_{1-2}$alkyl, naphthyl or substituted naphthyl (where the naphthyl substituents are $C_{1-5}$alkyl, carboxy $C_{1-5}$alkoxycarbonyl, carboxamido, amino, $C_{1-5}$alkylamino, hydroxy, $C_{1-5}$alkylcarbonylamino, $C_{1-5}$alkoxy, fluorine, bromine or chlorine), $R_5$ and $R_6$ are each hydrogen or taken together with the carbon to which each is attached to form a carbonyl,
b is 0 or 1;
G is

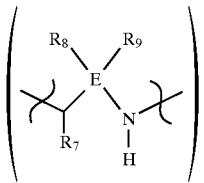

where the amine of G is bound to the ring methylenes and the methine is bound to the depicted amide, $R_7$ is selected from the group consisting of hydrogen, $C_{1-5}$alkyl, carboxy$C_{1-5}$alkyl, phenyl, substituted phenyl (where the phenyl substituents are $C_{1-5}$alkyl, carboxy $C_{1-5}$alkoxycarbonyl, carboxamido, amino, $C_{1-5}$alkylamino, hydroxy, $C_{1-5}$alkylcarbonylamino, $C_{1-5}$alkoxy, fluorine bromine or chlorine), phenyl$C_{1-5}$alkyl, substituted phenyl$C_{1-5}$alkyl (where the phenyl substituents are $C_{1-5}$alkyl, carboxy $C_{1-5}$alkoxycarbonyl, carboxamido, amino, $C_{1-5}$alkylamino, hydroxy, $C_{1-5}$alkylcarbonylamino, $C_{1-5}$alkoxy, fluorine bromine or chlorine), 3-pyridyl$C_{1-5}$alkyl, 4-pyridyl$C_{1-5}$alkyl, diphenyl$C_{1-2}$alkyl, naphthyl or substituted naphthyl (where the naphthyl substituents are $C_{1-5}$alkyl, carboxy $C_{1-5}$alkoxycarbonyl, carboxamido, amino, $C_{1-5}$alkylamino, hydroxy, $C_{1-5}$alkylcarbonylamino, $C_{1-5}$alkoxy, fluorine, bromine or chlorine), E is carbon or $C(CH_2)_q$—, where q is 0 to 12, with the proviso that the sum of q and m cannot exceed 25, $R_8$ and $R_9$ are each hydrogen or taken together with the carbon of E to form a carbonyl,
g is 0 or 1;
or pharmaceutically acceptable salts thereof.

Yet another aspect of the invention relates to novel thrombin inhibitors of the Formula III.

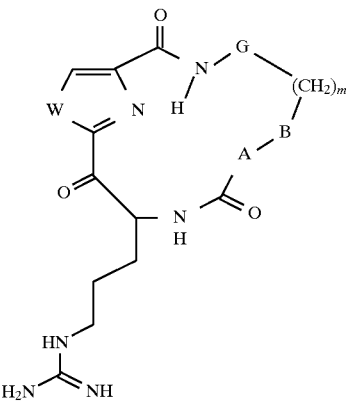

wherein:
m is 2 to 12;
W is nitrogen, sulfur or oxygen;
A is

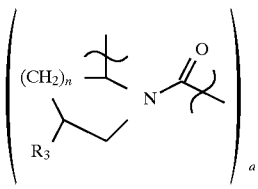

where the amido carbonyl is bound to B and the α aminomethine is bound to the depicted ring carbonyl, $R_3$ is hydrogen, hydroxy or $C_{1-5}$alkoxy,
n is 1 or 2;
a is 0 or 1;
B is

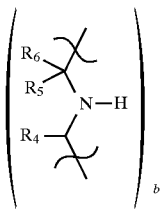

where the amido carbonyl of B is bound to the depicted ring methylenes and the methine is bound to A, $R_4$ is selected from the group consisting of hydrogen, $C_{1-5}$alkyl, carboxy$C_{1-5}$alkyl, phenyl, substituted phenyl (where the phenyl substituents are $C_{1-5}$alkyl, carboxy $C_{1-5}$alkoxycarbonyl, carboxamido, amino, $C_{1-5}$alkylamino, hydroxy, $C_{1-5}$alkylcarbonylamino, $C_{1-5}$alkoxy, fluorine bromine or chlorine), phenyl$C_{1-5}$alkyl, substituted phenyl$C_{1-5}$alkyl (where the phenyl substituents are $C_{1-5}$alkyl, carboxy $C_{1-5}$alkoxycarbonyl, carboxamido, amino, $C_{1-5}$alkylamino, hydroxy, $C_{1-5}$alkylcarbonylamino, $C_{1-5}$alkoxy, fluorine bromine or chlorine), 3-pyridyl$C_{1-}$ 5alkyl, 4-pyridylC$_{1-5}$alkyl, diphenylC$_{1-2}$alkyl, naphthyl or substituted naphthyl (where the naphthyl substituents are C$_{1-5}$alkyl, carboxy C$_{1-5}$alkoxycarbonyl, carboxamido, amino, C$_{1-5}$alkylamino, hydroxy, C$_{1-5}$alkylcarbonylamino, C$_{1-5}$alkoxy, fluorine bromine or chlorine), R$_5$ and R$_6$ are each hydrogen or taken together with the carbon to which they are attached to form a carbonyl, b is 0 or 1;

G is

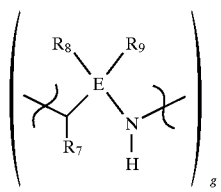

where the amine of G is bound to the ring methylenes and the methine is bound to the depicted amide, R$_7$ is independently selected from the group consisting of hydrogen, C$_{1-5}$alkyl, carboxyC$_{1-5}$alkyl, phenyl, substituted phenyl (where the phenyl substituents are C$_{1-5}$alkyl, carboxy C$_{1-5}$alkoxycarbonyl, carboxamido, amino, C$_{1-5}$alkylamino, hydroxy, C$_{1-5}$alkylcarbonylamino, C$_{1-5}$alkoxy, fluorine bromine or chlorine), phenylC$_{1-5}$alkyl, substituted phenylC$_{1-5}$alkyl (where the phenyl substituents are C$_{1-5}$alkyl, carboxy C$_{1-5}$alkoxycarbonyl, carboxamido, amino, C$_{1-5}$alkylamino, hydroxy, C$_{1-5}$alkylcarbonylamino, C$_{1-5}$alkoxy, fluorine bromine or chlorine), 3-pyridylC$_{1-5}$alkyl, 4-pyridylC$_{1-5}$alkyl, diphenylC$_{1-2}$alkyl, naphthyl or substituted naphthyl (where the naphthyl substituents are C$_{1-5}$alkyl, carboxy C$_{1-5}$alkoxycarbonyl, carboxamido, amino, C$_{1-5}$alkylamino, hydroxy, C$_{1-5}$alkylcarbonylamino, C$_{1-5}$alkoxy, fluorine bromine or chlorine), E is carbon or C(CH$_2$)$_q$—, where q is 0 to 12, with the proviso that the sum of q and m cannot exceed 25, R$_8$ and R$_9$ are each hydrogen or taken together with the carbon of E to form a carbonyl, g is 0 or 1;

or pharmaceutically acceptable salts thereof.

The terms used in describing the invention are commonly used and known to those skilled in the art. However, the terms that could have other meanings are defined. "Independently" means that when there are more than one substituent, the substitutents may be the same or different. The term "alkyl" refers to straight, cyclic and branched-chain alkyl groups and "alkoxy" refers to O-alkyl where alkyl is as defined supra. "CBZ" refers to benzyloxycarbonyl. "BOC" refers to t-butoxycarbonyl and "Ts" refers to toluenesulfonyl. "DCC" refers to 1,3-dicyclohexylcarbodiimide, "DMAP" refers to 4-N'N-dimethylaminopyridine and "HOBT" refers to 1-hydroxybenzotriazole hydrate. "FMoc" refers to N-(9-fluorenylmethoxycarbonyl). Amino acid refers to compounds where the amino group and the carboxy group are on different carbon atoms. The term α-amino acid, refers to compounds where both the carboxy and the amino group are attached to the same carbon atom. The stereochemistry of this carbon is indicated by the terms "D and L" where D indicates right-handed chirality.

DETAILED DESCRIPTION OF THE INVENTION

The compounds of the invention may be prepared by a number of synthetic schemes, where the macrocyclic ring members A, B, and G dictate the appropriate synthesis. The starting protected mono and di-peptides are either known or readily synthesized by standard techniques known in the art. See Bodansky, M. *Practice of Peptide Synthesis*; Springer Verlag, 1984. All syntheses include a series of peptide coupling reactions, where the macrocycle is built, oxidized and deprotected.

As illustrated, Scheme I may be used to prepare a compound of Formula I where m is 7;

A is

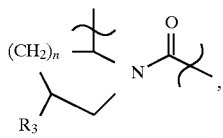

where R$_3$ is hydrogen and n is 1;

B is

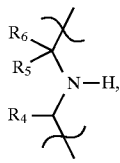

where R$_4$ is 2-methyl-1-propyl and R$_5$ is taken together with R$_6$ to form a carbonyl. A known N-protected α-amino acid Ia, is coupled at room temperature to a known C-protected amino acid Ib, using HOBT/DCC in an inert solvent, such as DMF, CH$_3$CN or THF, over 5–24 h. Although HOBT/DCC is the preferred coupling agent other agents can be used and include: BOP, BOP-Cl and PyBrOP. The protecting groups are chosen in order to permit selective removal, where the favored protecting groups are CBZ for nitrogen and t-butoxycarbonyl for carboxy. However, other well known protecting groups may be substituted and are described in Green, Theodora *Protecting Groups in Organic Synthesis*; John Wiley & Sons, New York, 1981. As illustrated the CBZ group is removed by hydrogenation at approximately 20 psig using Pd(OH)$_2$/C as a catalyst. However, other conditions may be used such as catalytic transfer hydrogenation using Pd/C and formic acid. The resulting C-protected di-peptide Ic, is coupled to an N-protected aliphatic amino acid, Id, followed by removal of the N-protecting group to give amine Ie. As illustrated, the CBZ serves as the N-protecting group and Pd/(OH)$_2$ is the hydrogenation catalyst. However either the protecting group or the reaction conditions may be modified as previously described. Intermediate Ie is coupled to 6-[[imino[4-methylbenzenesulfonyl)-amino]methyl]amino]-2-(R,S)-[[2-(trimethylsilyl)ethoxy]methoxy]-3(S)-[9-phenylmethoxycarbonyl)-amino]hexanoic acid, ( Maryanoff et al. *Journal of the American Chemical Society* 1995, 117, 1225–39) using HOBT/DCC at room temperature for 4–24 h in an inert solvent and deprotected with Pd(OH)$_2$ to give the arginine derivative If. The t-butoxycarbonyl and SEM protecting groups are removed with TFA and the resulting intermediate is coupled at room temperature with BOP-Cl and DMAP in an inert solvent such as CH$_2$Cl$_2$ to give the hydroxy macrocyclic derivative Ig. Compound Ig is oxidized using the Dess-Martin periodinane in an anhydrous aprotic solvent and deprotected using HF in the presence of a carbocation scavenger such as anisole, thioanisole, pentamethylbenzene, dimethylsulfide or cresol to give a compound of Formula I.

This scheme may be used to form the compounds of the invention where m is 2–12, A is

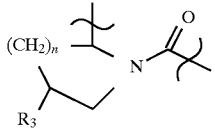

where n is 1 or 2 and $R_3$ is hydrogen or $C_{1-5}$alkoxy, and B is

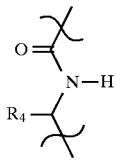

where $R_4$ is hydrogen, $C_{1-5}$alkyl, phenyl, substituted phenyl (where the phenyl substituents are $C_{1-5}$alkyl, carboxy $C_{1-5}$alkoxycarbonyl, carboxamido, amino, $C_{1-5}$alkylamino, hydroxy, $C_{1-5}$alkylcarbonylamino, $C_{1-5}$alkoxy, fluorine bromine or chlorine), phenyl$C_{1-5}$alkyl, substituted phenyl$C_{1-5}$alkyl (where the phenyl substituents are $C_{1-5}$alkyl, carboxy $C_{1-5}$alkoxycarbonyl, carboxamido, amino, $C_{1-5}$alkylamino, hydroxy, $C_{1-5}$alkylcarbonylamino, $C_{1-5}$alkoxy, fluorine bromine or chlorine), 3-pyridyl$C_{1-5}$alkyl, 4-pyridyl$C_{1-5}$alkyl, naphthyl, substituted naphthyl or diphenyl$C_{1-2}$alkyl. For example to prepare compounds where m is 2–12, the illustrated reactant Id, 8-(N-benzyloxycarbonyl)aminooctanoic acid, is replaced with an analog of "m" methylenes such as 6-(N-benzyloxycarbonyl)aminohexanoic acid. To prepare a compound where A is

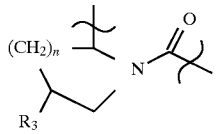

$R_3$ is hydrogen and n is 2, simply replace Ib, D-Pro-O-t-Bu, with D-pipecolinic acid -t-butyl ester To prepare a compound where B is

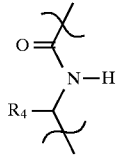

and $R_4$ is 3-pyridylmethyl, replace Ia N-BOC-D-leucine with N-BOC-D-3-pyridyl-alanine. When active aromatic substituents are desired such as hydroxy, amino or carboxy, those compounds may be prepared as protected derivatives where the protecting groups well known in the art are described in Green, Theodora *Protecting Groups in Organic Synthesis*; John Wiley & Sons, New York, 1981. For example to prepare a compound where $R_4$ is 4-hydroxybenzyl, a t-butyldimethylsilyl group is used as protecting group and removed with HF in the last step of the scheme.

SCHEME I

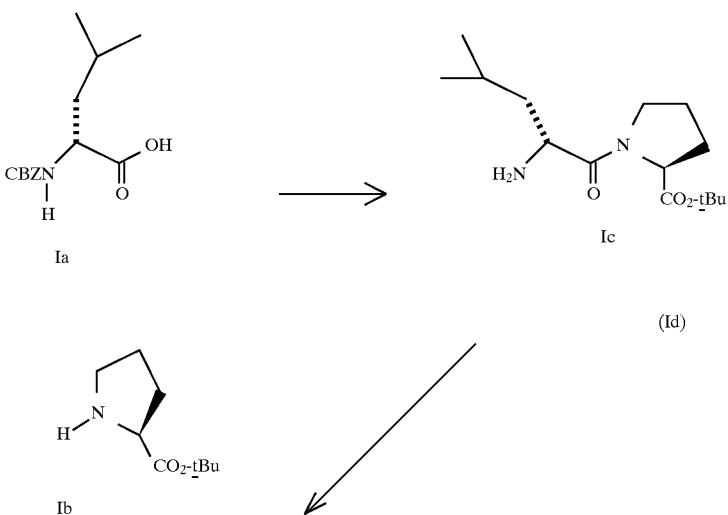

-continued
SCHEME I
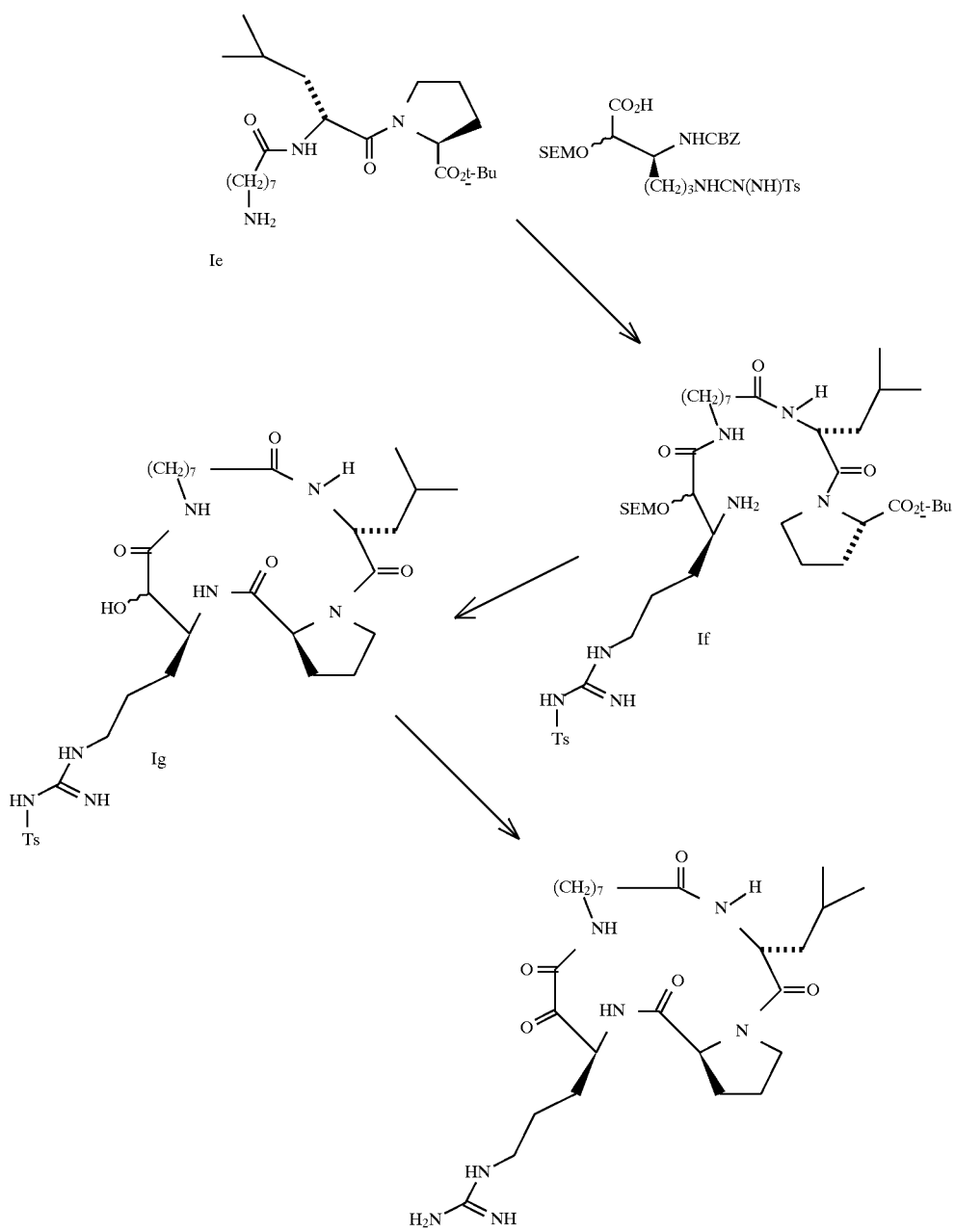
Another method of synthesis, illustrated by Scheme II, may be used to prepare a compound of Formula I where m is 4;
A is
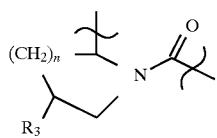
where $R_3$ is hydrogen and n is 1;
B is
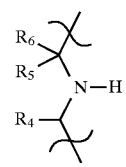

where $R_4$ is benzyl and $R_5$ is taken together with $R_6$ to form a carbonyl; and
G is

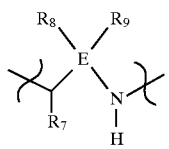

where E, $R_8$ and $R_9$ are taken together to form a carbonyl and $R_7$ is 4-chlorobenzyl.

A known N-protected -α-amino acid IIa, is coupled at room temperature to a known C-protected amino acid IIb, using HOBT/DCC in an inert solvent, such as DMF, $CH_3CN$ or THF, over 5–24 h. Although HOBT/DCC is the preferred coupling agent other agents may be used and include: BOP, BOP-Cl and PyBrOP. The protecting groups are chosen in order to permit selective removal, where the favored protecting groups are CBZ for nitrogen and -t-butoxycarbonyl for carboxy. However, other protecting groups well known in the art may be substituted and are described in Green, Theodora, *Protecting Groups in Organic Synthesis*; John Wiley & Sons, New York, 1981. As illustrated the -t-butoxycarbonyl group is removed with TFA to give the N-protected di-peptide IIc. This intermediate is coupled to an C-protected di-peptide IId, followed by removal of the N-protecting group to give amine IIe. As illustrated the CBZ serves as the N-protecting group and $Pd/(OH)_2$ is the hydrogenation catalyst. However either the protecting group or the reaction conditions may be modified as previously described. Intermediate IIe is coupled to 6-[[imino[4-methylbenzenesulfonyl)-amino]methyl]amino]-2-(R,S)-[[2-(trimethylsilyl)ethoxy]methoxy]-3(S)-[9-phenylmethoxycarbonyl)-amino]hexanoic acid, (Maryanoff et al. *Journal of the American Chemical Society* 1995, 117, 1225–39) using HOBT/DCC at room temperature for 4–24 h in an inert solvent and deprotected with $Pd(OH)_2$ to give the arginine derivative hf. The t-butoxycarbonyl and SEM protecting groups are removed with TFA and the resulting intermediate is coupled at room temperature with BOP-Cl and DMAP in an inert solvent such as $CH_2Cl_2$ to give the hydroxy macrocyclic derivative IIg. Compound IIg is oxidized using the Dess-Martin periodinane in an anhydrous aprotic solvent and deprotected using HF in the presence of a carbocation scavenger to give a compound of Formula I.

This scheme may be used to form the compounds of the invention where m is 2–12, A is

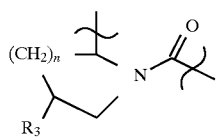

where $R_3$ is hydrogen or $C_{1-5}$alkoxy, B is

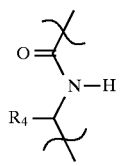

where $R_4$ is hydrogen, $C_{1-5}$alkyl, phenyl, substituted phenyl (where the phenyl substituents are $C_{1-5}$alkyl, carboxy $C_{1-5}$alkoxycarbonyl, carboxamido, amino, $C_{1-5}$alkylamino, hydroxy, $C_{1-5}$alkylcarbonylamino, $C_{1-5}$alkoxy, fluorine bromine or chlorine), phenyl$C_{1-5}$alkyl, substituted phenyl$C_{1-5}$alkyl (where the phenyl substituents are $C_{1-5}$alkyl, carboxy $C_{1-5}$alkoxycarbonyl, carboxamido, amino, $C_{1-5}$alkylamino, hydroxy, $C_{1-5}$alkylcarbonylamino, $C_{1-5}$alkyl, fluorine bromine or chlorine), 3-pyridyl$C_{1-5}$alkyl, 4-pyridyl$C_{1-5}$alkyl or diphenyl$C_{1-2}$alkyl, and G is

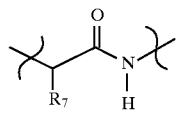

where $R_7$ is hydrogen, $C_{1-5}$alkyl, phenyl, substituted phenyl (where the phenyl substituents are $C_{1-5}$alkyl, carboxy $C_{1-5}$alkoxycarbonyl, carboxamido, amino, $C_{1-5}$alkylamino, hydroxy, $C_{1-5}$alkylcarbonylamino, $C_{1-5}$alkoxy, fluorine bromine or chlorine), phenyl$C_{1-5}$alkyl, substituted phenyl$C_{1-5}$alkyl (where the phenyl substituents are $C_{1-5}$alkyl, carboxy $C_{1-5}$alkoxycarbonyl, carboxamido, amino, $C_{1-5}$alkylamino, hydroxy, $C_{1-5}$alkylcarbonylamino, $C_{1-5}$alkoxy, fluorine bromine or chlorine), 3-pyridyl$C_{1-5}$alkyl, 4-pyridyl$C_{1-5}$alkyl, naphthyl or diphenyl$C_{1-2}$alkyl. For example to prepare compounds where m is 2–12, the illustrated reactant IIb, 5-aminopentanoic acid -t-butyl ester is replaced with an analog of "m" methylenes such as 7-aminoheptanoic acid -t-butyl ester. To prepare a compound where A is

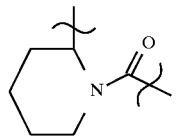

and B is

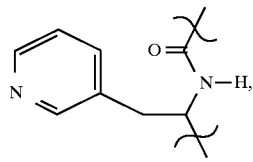

replace the illustrated reactant IId with 3-pyridylalanine-pipecolinic acid (O-tBu) A compound where G is

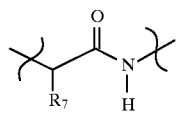

and $R_7$ is butyl can be prepared by replacing IIa with N-BOC-D-norleucine. When the aromatic substituents hydroxy, amino or carboxy are desired, those compounds may be prepared as protected derivatives where the protecting groups well known in the art are described in Green, Theodora *Protecting Groups in Organic Synthesis*; John Wiley & Sons, New York, 1981. For example to prepare compound where $R_4$ or $R_7$ is 4-aminobenzyl, an allyloxycarbonyl group is used as protecting group and removed with tetrakis(triphenylphosphine)palladium(0) at the end of the scheme.

SCHEME II
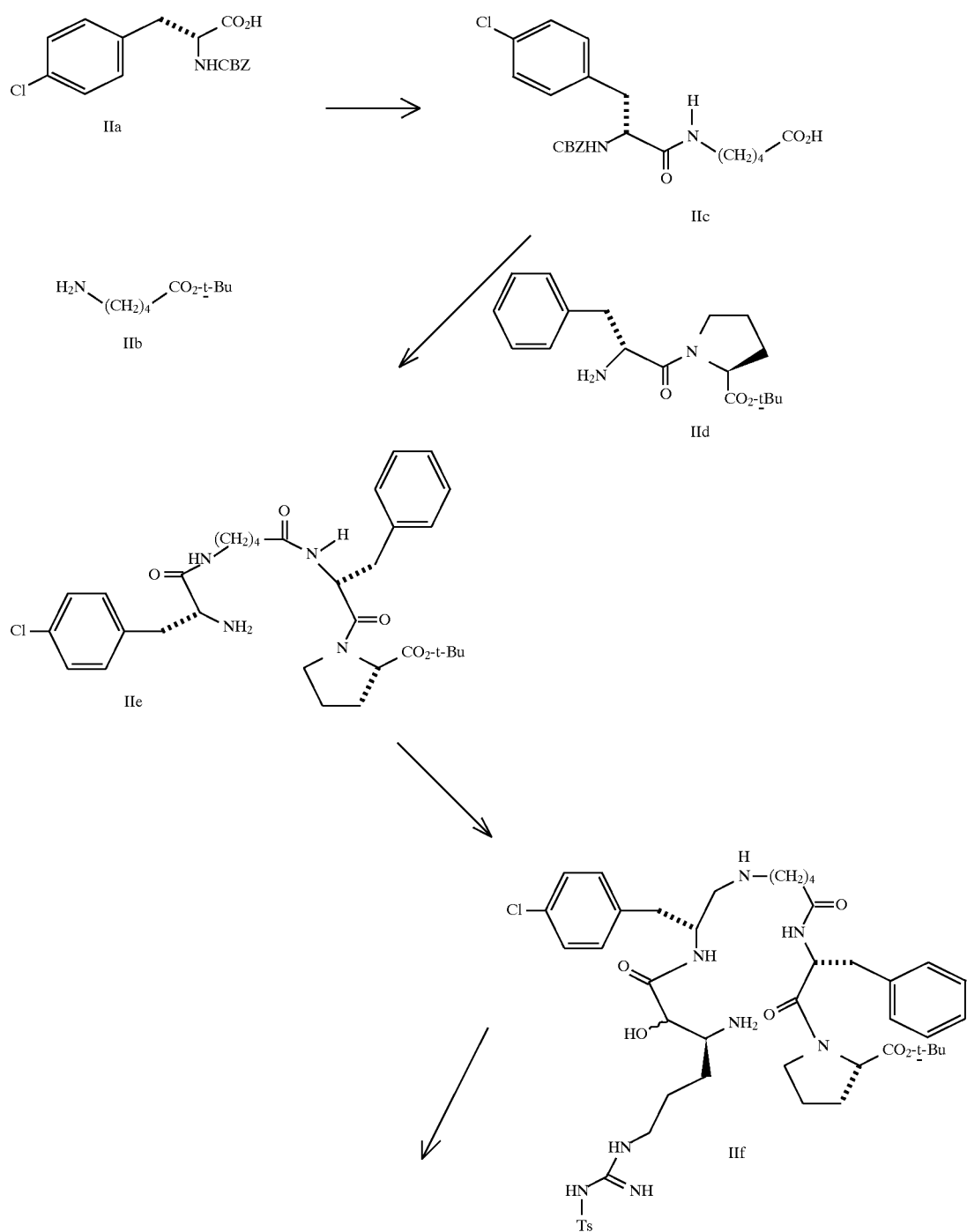

-continued
SCHEME II

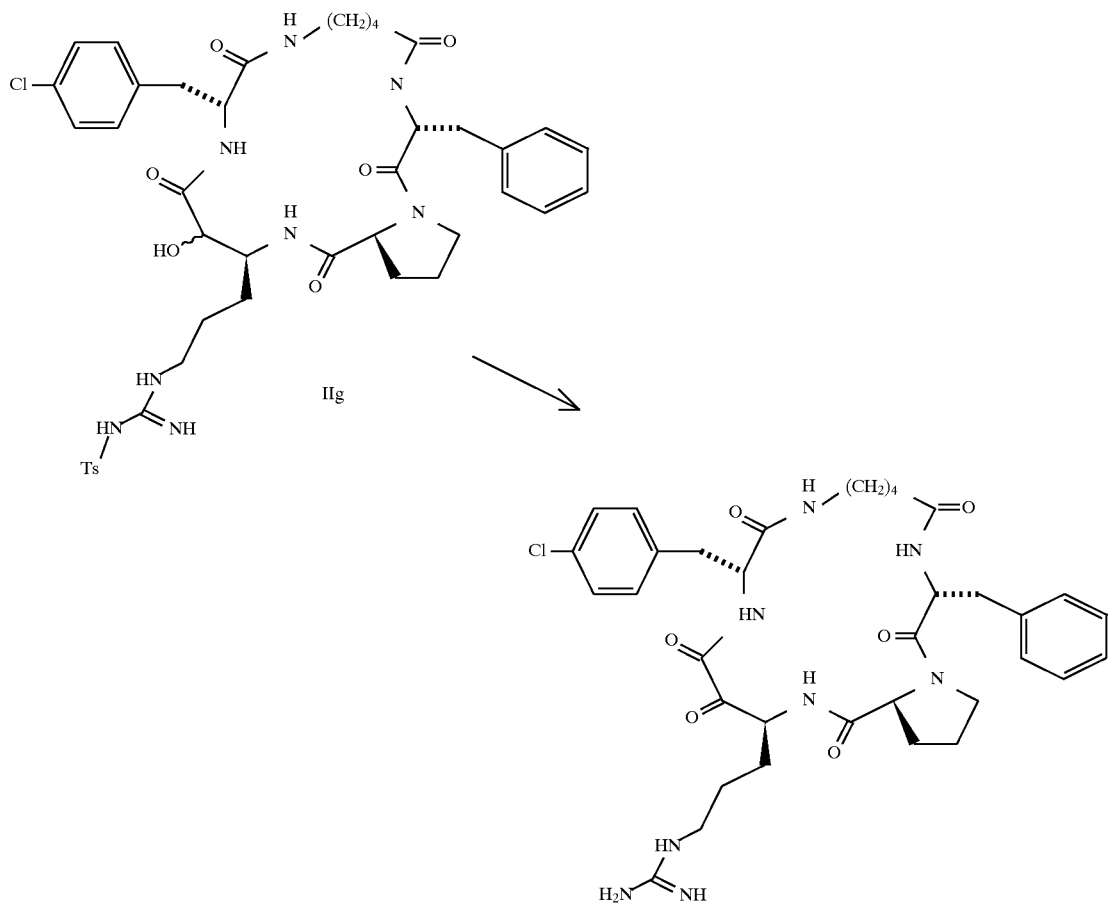

Yet another method, illustrated by Scheme III, is used to prepare a compound of Formula I where m is 3;

A is

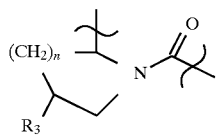

where $R_3$ is hydrogen and n is 2;

B is

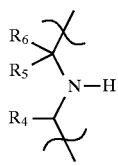

where $R_4$ is benzyl and both $R_5$ as well as $R_6$ are hydrogen. A known N-protected aldehyde IIIa, is reductively aminated at room temperature to a known C-protected amino acid IIIb, using $NaB(OAc)_3H$ in an inert solvent, such as $CH_2Cl_2$ or $(CH_2)_2Cl_2$, over 2–16 h. The protecting groups are chosen in order to permit selective removal, where the favored protecting groups are Fmoc for nitrogen and t-butoxycarbonyl for carboxy. However, other protecting groups may be substituted as previously discussed. The free amine of the resulting product IIIc is protected as the CBZ and the Fmoc group of the other amine is cleaved with an anhydrous base such as piperidine to give IIId. Intermediate IIId is coupled to 6-[[imino[4-methylbenzenesulfonyl)-amino]methyl]amino]-2-(R, S)-[[2-(trimethylsilyl)ethoxy]methoxy]-3(S)-[9-fluorenylmethoxycarbonyl)-amino]hexanoic acid, (Maryanoff et al. *Journal of the American Chemical Society* 1995, 117, 1225–39) using HOBT/DCC at room temperature for 4–24 h in an inert solvent and deprotected with $Pd(OH)_2$ to give the arginine derivative IIIe. The Fmoc group is removed with an organic base and the t-butoxycarbonyl and SEM protecting groups are removed with TFA. The resulting intermediate is coupled at room temperature with BOP-Cl and DMAP in an inert solvent such as $CH_2Cl_2$ to give the hydroxy macrocyclic derivative IIIf. Compound IIIf is oxidized using the Dess-Martin periodinane in an anhydrous aprotic solvent and deprotected using HF in the presence of a carbocation scavenger to give a compound of Formula I.

This Scheme III may be used to form the compounds of the invention where m is 2–12, A is

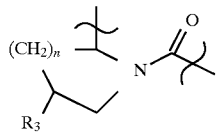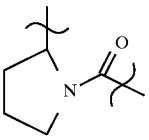

where $R_3$ hydrogen or $C_{1-5}$alkoxy and n is 1 or 2, and B is and B is

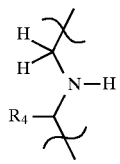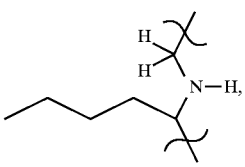

where $R_4$ is hydrogen, $C_{1-5}$alkyl, phenyl, substituted phenyl (where the phenyl substituents are $C_{1-5}$alkyl, carboxy $C_{1-5}$alkoxycarbonyl, carboxamido, amino, $C_{1-5}$alkylamino, hydroxy, $C_{1-5}$alkylcarbonylamino, $C_{1-5}$alkoxy, fluorine bromine or chlorine), 3-pyridyl$C_{1-5}$alkyl, 4-pyridyl$C_{1-5}$alkyl or diphenyl$C_{1-2}$alkyl. For example to prepare compounds where m is 2–12, the illustrated reactant IIIa, is replaced with an analog of "m" methylenes such as 5-(N-9-fluorenylmethoxycarbonyl)aminopentaldehyde. To prepare a compound where A is replace the illustrated reactant IIIb with norleucine-proline-(O-t-Bu). When active aromatic substituents are desired such as hydroxy, amino or carboxy, those compounds may be prepared as protected derivatives where the protecting groups well known in the art are described in Green, Theodora *Protecting Groups in Organic Synthesis*; John Wiley & Sons, New York, 1981. For example to prepare compound where $R_4$ is 4-carboxybenzyl, an methylester is used as protecting group and removed with aqueous LiOH prior to oxidation with Dess Martin periodiane.

SCHEME III

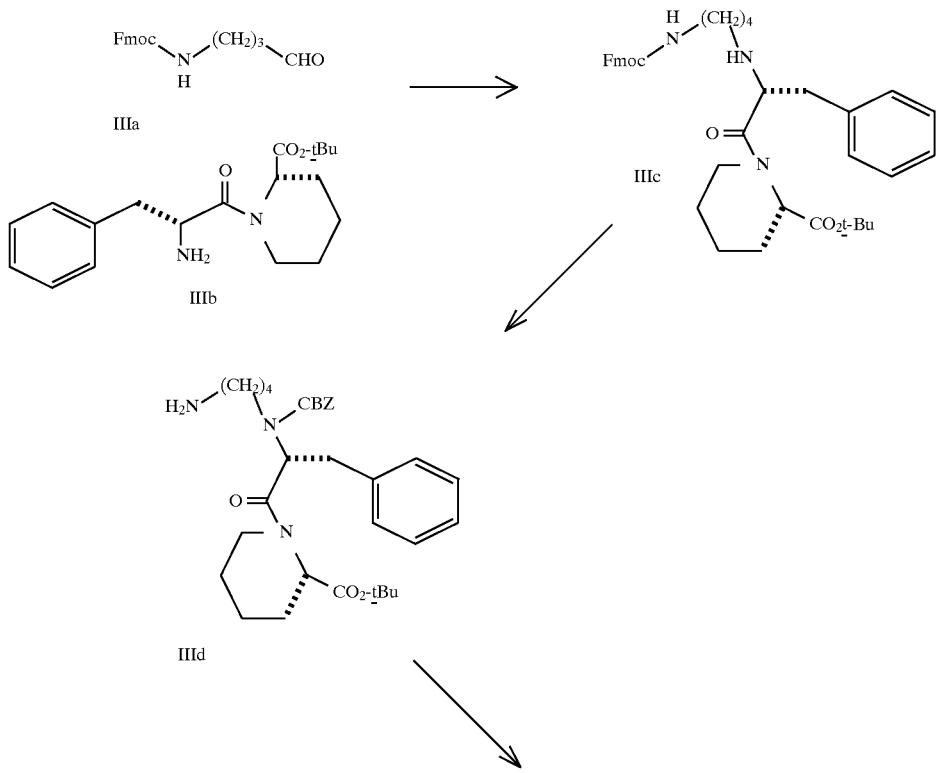

-continued
SCHEME III
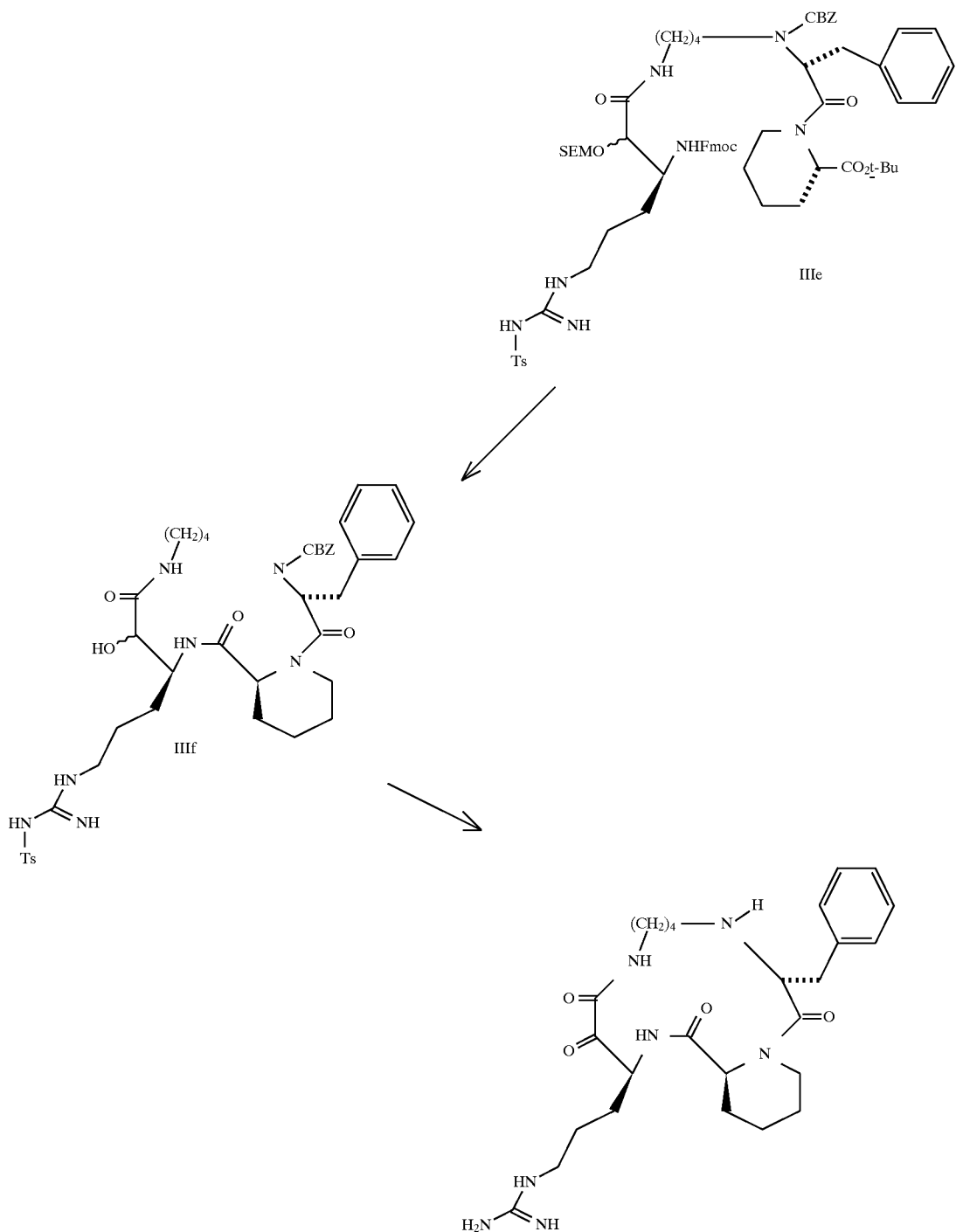
Another method of synthesis is illustrated by Scheme IV may be used to prepare a compound of Formula I where m is 5;
A is
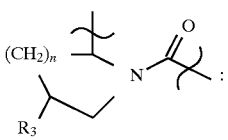

where $R_3$ is hydrogen and n is 1; and

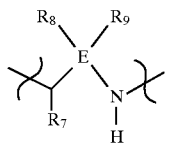

G is
where E, $R_8$ and $R_9$ are taken together to form a carbonyl and $R_7$ is phenyl.

A known N-protected amino acid IVa, is coupled at room temperature to a known C-protected amino acid IVb, using HOBT/DCC in an inert solvent, such as DMF, $CH_3CN$ or THF, over 5–24 h. Although HOBT/DCC is the preferred coupling agent other agents be used and include: BOP, BOP-Cl and PyBrOP. The preferred protecting groups are CBZ for nitrogen and t-butoxycarbonyl for carboxy; however, other protecting groups may be substituted as discussed previously. As illustrated the t-butoxycarbonyl group is removed with TFA to give the N-protected di-peptide IVc. This intermediate is coupled to an C-protected di-peptide IVd, followed by removal of the N-protecting group to give amine IVe. As illustrated the CBZ serves as the N-protecting group and $Pd/(OH)_2$ is the hydrogenation catalyst. However either the protecting group or the reaction conditions may be modified as previously described. Intermediate IVe is coupled to 6-[[imino[4-methylbenzenesulfonyl)-amino]methyl]amino]-2-(R,S)-[[2-(trimethylsilyl)ethoxy]methoxy]-3(S)-[9-phenylmethoxycarbonyl)-amino]hexanoic acid, (Maryanoff et al. *Journal of the American Chemical Society* 1995, 117, 1225–39) using HOBT/DCC at room temperature for 4–24 h in an inert solvent and deprotected with $Pd(OH)_2$ to give the arginine derivative IVf. The t-butoxycarbonyl and SEM protecting groups are removed with TFA and the resulting intermediate is coupled at room temperature with BOP-Cl and DMAP in an inert solvent such as $CH_2Cl_2$ to give the hydroxy macrocyclic derivative IVg. Compound IVg is oxidized using periodinane in an anhydrous aprotic solvent and deprotected using HF in the presence of a carbocation scavenger to give a compound of Formula I.

This Scheme IV may be used to form the compounds of the invention where m is 2–12, A is

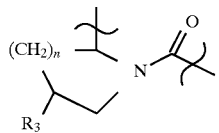

and G is

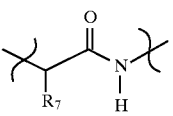

where $R_7$ is hydrogen, $C_{1-5}$alkyl, phenyl, substituted phenyl (where the phenyl substituents are $C_{1-5}$alkyl, carboxy $C_{1-5}$alkoxycarbonyl, carboxamido, amino, $C_{1-5}$alkylamino, hydroxy, $C_{1-5}$alkylcarbonylamino, $C_{1-5}$alkoxy, fluorine bromine or chlorine), phenyl$C_{1-5}$alkyl, substituted phenyl$C_{1-5}$alkyl (where the phenyl substituents are $C_{1-5}$alkyl, carboxy $C_{1-5}$alkoxycarbonyl, carboxamido, amino, $C_{1-5}$alkylamino, hydroxy, $C_{1-5}$alkylcarbonylamino, $C_{1-5}$alkoxy, fluorine bromine or chlorine), 3-pyridyl$C_{1-5}$alkyl, 4-pyridyl$C_{1-5}$alkyl naphthyl or diphenyl$C_{1-2}$alkyl. For example to prepare compounds where m is 2–12, the illustrated reactant IVa, 6-(N-CBZ)aminohexanoic acid is replaced with an analog of "m" methylenes such as 7-(N-CBZ)aminoheptanoic acid. To prepare a compound where A is

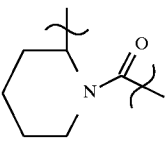

replace the illustrated reactant IVb with D-pipecolinic acid t-butyl ester. A compound where G is

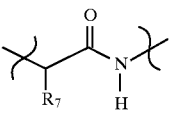

and $R_7$ is butyl can be prepared by replacing IVd with D-norleucine. When active aromatic substituents are desired such as hydroxy, amino or carboxy, those compounds may be prepared as protected derivatives where the protecting groups well known in the art are described in Green, Theodora *Protecting Groups in Organic Synthesis*; John Wiley & Sons, New York, 1981. For example to prepare compound where $R_7$ is 4-hydroxybenzyl, a t-butyidimethylsilyl group is used as protecting group and removed with HF in the last step of the scheme.

SCHEME IV

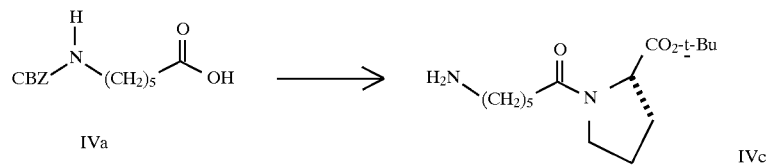

-continued
SCHEME IV
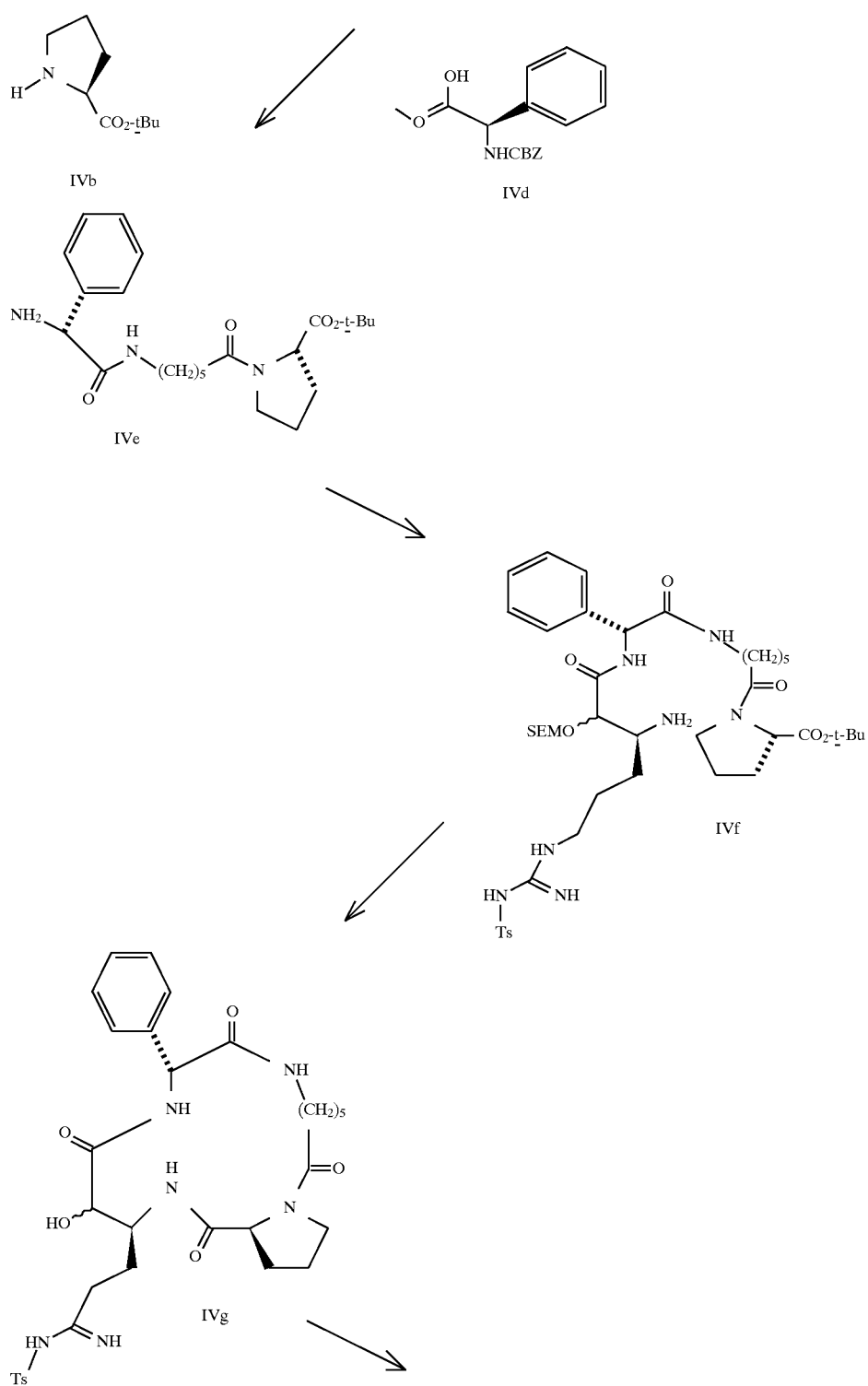

-continued
SCHEME IV

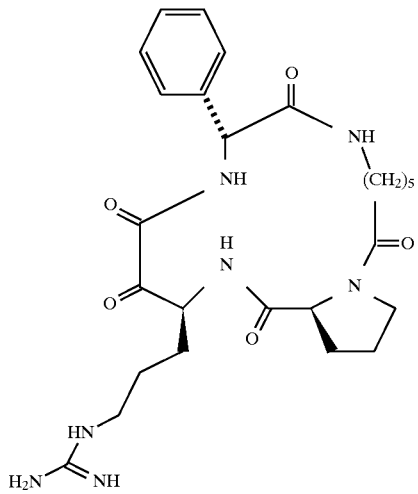

Another method of synthesis is illustrated by Scheme V and may be used to prepare a compound of Formula I where m is 5;

A is

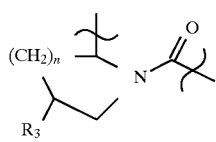

where $R_3$ is methoxy;
n is 1;
B is

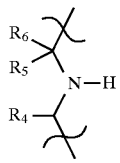

where $R_4$ is 4-chlorobenzyl and $R_5$ is taken together with R6 to form a carbonyl; and
G is

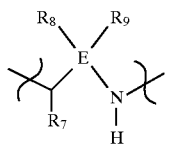

where E is carbon, $R_8$ and $R_9$ are hydrogen and $R_7$ is hydrogen.

A known Fmoc-protected amino aldehyde Va, is reductively aminated at room temperature to a known t-butoxy-protected amino acid Vb, using $NaB(O_2CCH_3)H$ in an inert solvent, such as $CH_2Cl_2$, over 5–24 h. The nitrogen of the resulting intermediate is protected with CBZ and the O-t-butoxy group is cleaved to give the acid Vc. This intermediate is coupled to a C-protected dipeptide Vd using HOBT/DCC followed by the removal of the FMoc protection with an anhydrous base such as diethylamine to give Ve. Intermediate Ve is coupled to 6-[[imino[4-methylbenzenesulfonyl)-amino]methyl]amino]-2-(R,S)-[[2-(trimethylsilyl)ethoxy]methoxy]-3(S)-[9-fluorenyllmethoxycarbonyl)-amino]hexanoic acid, (Maryanoff et al. *Journal of the American Chemical Society* 1995, 117, 1225–39) using HOBT/DCC at room temperature for 4–24 h in an inert solvent and deprotected with diethylamine to give the acyclic arginine derivative Vf. The t-butoxycarbonyl and SEM protecting groups are removed with TFA and the resulting intermediate is coupled at room temperature with BOP-Cl and DMAP in an inert solvent such as $CH_2Cl_2$ to give the hydroxy macrocyclic derivative Vg. Compound Vg is oxidized using periodinane in an anhydrous aprotic solvent and deprotected using HF in the presence of a carbocation scavenger to give a compound of Formula I.

This Scheme V may be used to form the compounds of the invention where m is 2–12, A is

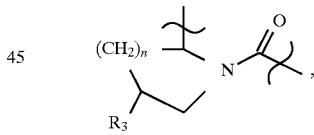

B is

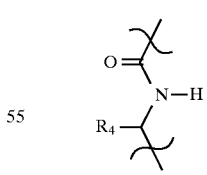

where $R_4$ is hydrogen, $C_{1-5}$alkyl, phenyl, substituted phenyl (where the phenyl substituents are $C_{1-5}$alkyl, carboxy $C_{1-5}$alkoxycarbonyl, carboxamido, amino, $C_{1-5}$alkylamino, hydroxy, $C_{1-5}$alkylcarbonylamino, $C_{1-5}$alkoxy, fluorine bromine or chlorine), phenyl$C_{1-5}$alkyl, substituted phenyl$C_{1-5}$alkyl (where the phenyl substituents are $C_{1-5}$alkyl, carboxy $C_{1-5}$alkoxycarbonyl, carboxamido, amino, $C_{1-5}$alkylamino, hydroxy, $C_{1-5}$alkylcarbonylamino, $C_{1-5}$alkoxy, fluorine bromine or chlorine), 3-pyridyl$C_{1-5}$alkyl, 4-pyridyl$C_{1-5}$alkyl naphthyl or diphenyl$C_{1-2}$alkyl, and G is

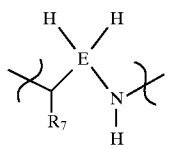

where $R_7$ is hydrogen, $C_{1-5}$alkyl, phenyl, substituted phenyl (where the phenyl substituents are $C_{1-5}$alkoxy, fluorine or chlorine), phenyl$C_{1-5}$alkyl, substituted phenyl$C_{1-5}$alkyl (where the phenyl substituents are $C_{1-5}$alkoxy, fluorine or chlorine), 3-pyridyl$C_{1-5}$alkyl, 4-pyridyl$C_{1-5}$alkyl naphthyl or diphenyl$C_{1-2}$alkyl and E is $C(CH_2)_q$, where q is 0–12. For example to prepare compounds where m is 2–12, the illustrated reactant Vb, is replaced with an analog of "m" methylenes such as 8-aminooctanoic acid -t-butyl ester. To prepare a compound where A is

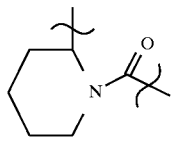

and B is

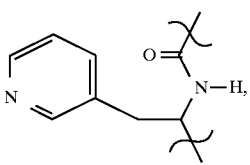

replace the illustrated reactant Vd with 3-pyridylalanine-D-pipecolinic acid -t-butyl ester. A compound where G is

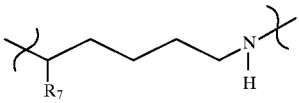

and $R_7$ is hydrogen can be prepared by replacing Va with 6-(N-9-fluorenylmethoxycarbonyl)aminobutylraldehyde. To prepare compounds where $R_7$ is other than hydrogen, start with an N-protected α-amino acid, reduce the carboxy to an aldehyde. Any of the standard reagents and conditions may be used including 1,1'-carbonyldiimidazole in THF at 0°–10° C., followed by treatment with DIBAL/hexane at −42° C. This α-substituted aldehyde is used in place of Va and the remaining steps of the synthesis are carried through with only minor modifications.

SCHEME V

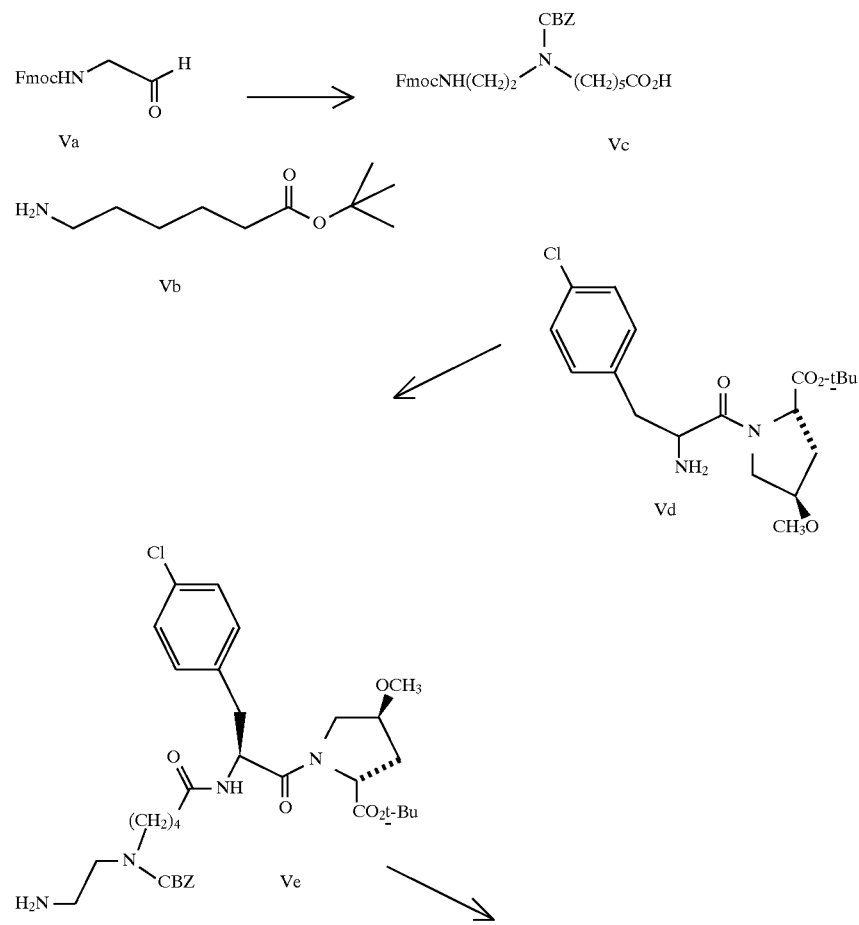

-continued
SCHEME V
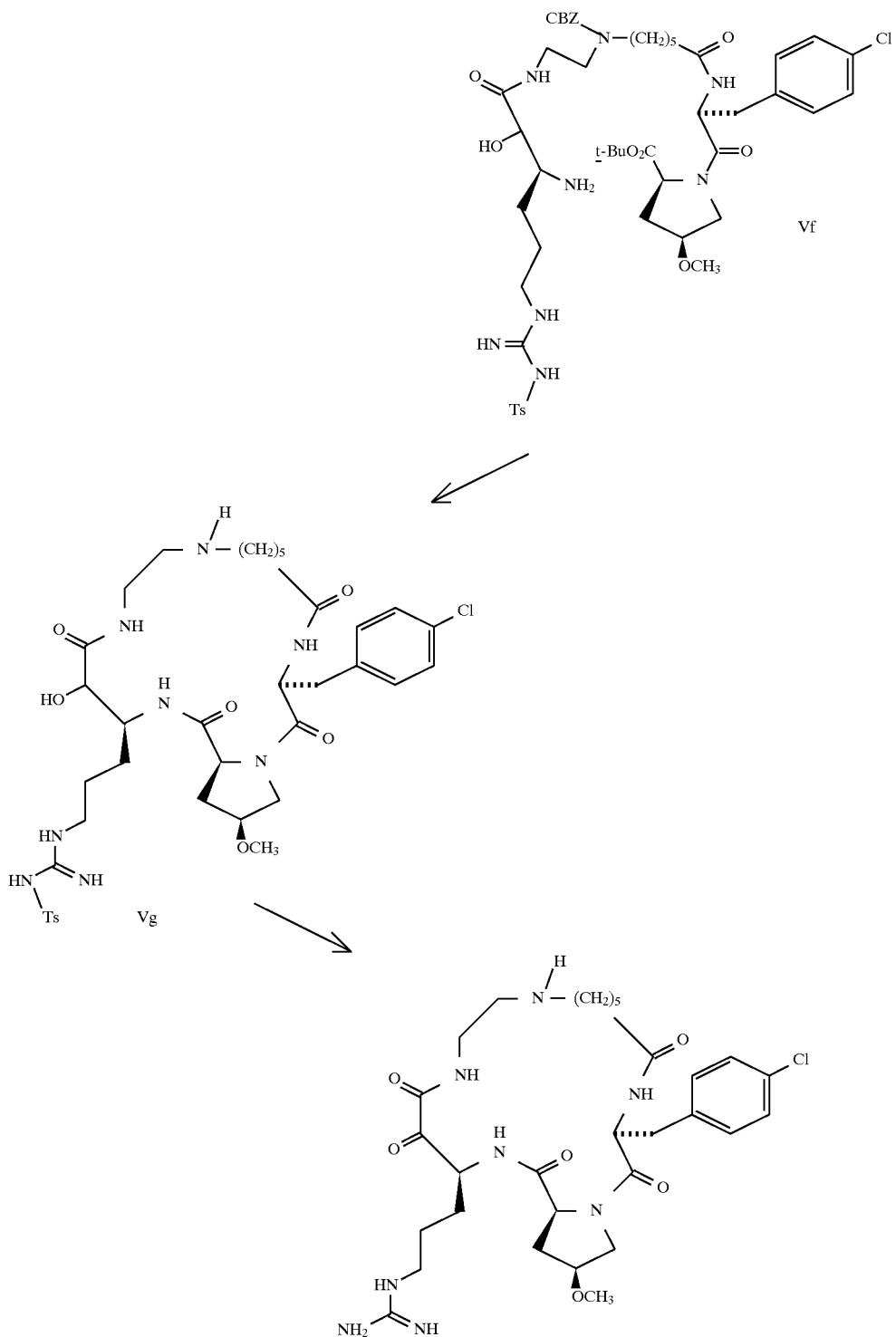
Yet another method of synthesis is illustrated by Scheme VI. This scheme is used to prepare a compound where m is 5 and G is
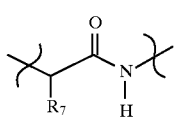

and $R_7$ is 4-chlorobenzyl.

A known N-protected amino acid VIa, is coupled at room temperature to a known C-protected amino acid VIb, using HOBT/DCC in an inert solvent, such as DMF, $CH_3CN$ or THF, over 5–24 h to give VIc. Although HOBT/DCC is the preferred coupling agent other agents be used and include: BOP, BOP-Cl and PyBrOP. The preferred protecting groups are CBZ for nitrogen and t-butoxycarbonyl for carboxy; however, other protecting groups may be substituted as discussed previously. The protecting groups are removed by sequential treatment with TFA and $Pd/(OH)_2/H_2$ to give VIc. Intermediate VIc is coupled to 6-[[imino[4-methylbenzenesulfonyl)-amino]methyl]amino]-2-(R,S)-[[2-(trimethylsilyl)ethoxy]methoxy]-3(S)-[9-phenylmethoxycarbonyl)-amino]hexanoic acid, (Maryanoff et al. *Journal of the American Chemical Society* 1995, 117, 1225–39) using HOBT/DCC at room temperature for 4–24 h in an inert solvent to give VId. The CBZ, t-butoxycarbonyl and SEM protecting groups are removed by sequential treatment with TFA and $Pd(OH)_2/H_2$ to give VIe. This intermediate is coupled at room temperature with BOP-Cl and DMAP in an inert solvent such as $CH_2Cl_2$ to give the hydroxy macrocyclic derivative VIf. Compound VIf is oxidized using periodinane in an anhydrous aprotic solvent and deprotected using HF in the presence of a carbocation scavenger such as anisole, thioanisole, pentamethylbenzene, dimethylsulfide or cresol to give a compound of Formula I.

This Scheme VI may be used to form the compounds of the invention where m is 2–12, and G is

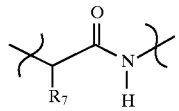

where $R_7$ is hydrogen, $C_{1-5}$alkyl, phenyl, substituted phenyl (where the phenyl substituents are $C_{1-5}$alkyl, carboxy $C_{1-5}$alkoxycarbonyl, carboxamido, amino, $C_{1-5}$alkylamino, hydroxy, $C_{1-5}$alkylcarbonylamino, $C_{1-5}$alkoxy, fluorine bromine or chlorine), phenyl$C_{1-5}$alkyl, substituted phenyl$C_{1-5}$alkyl (where the phenyl substituents are $C_{1-5}$alkyl, carboxy $C_{1-5}$alkoxycarbonyl, carboxamido, amino, $C_{1-5}$alkylamino, hydroxy, $C_{1-5}$alkylcarbonylamino, $C_{1-5}$alkoxy, fluorine bromine or chlorine), 3-pyridyl$C_{1-5}$alkyl, 4-pyridyl$C_{1-5}$alkyl naphthyl or diphenyl$C_{1-2}$alkyl. For example to prepare compounds where m is 2–12, the illustrated reactant VIb is replaced with an analog of "m" methylenes such as 8-aminoooctanoic acid t-butyl ester. A compound where G is

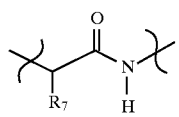

and $R_7$ is butyl can be prepared by replacing VIb with N-BOC-D-norleucine

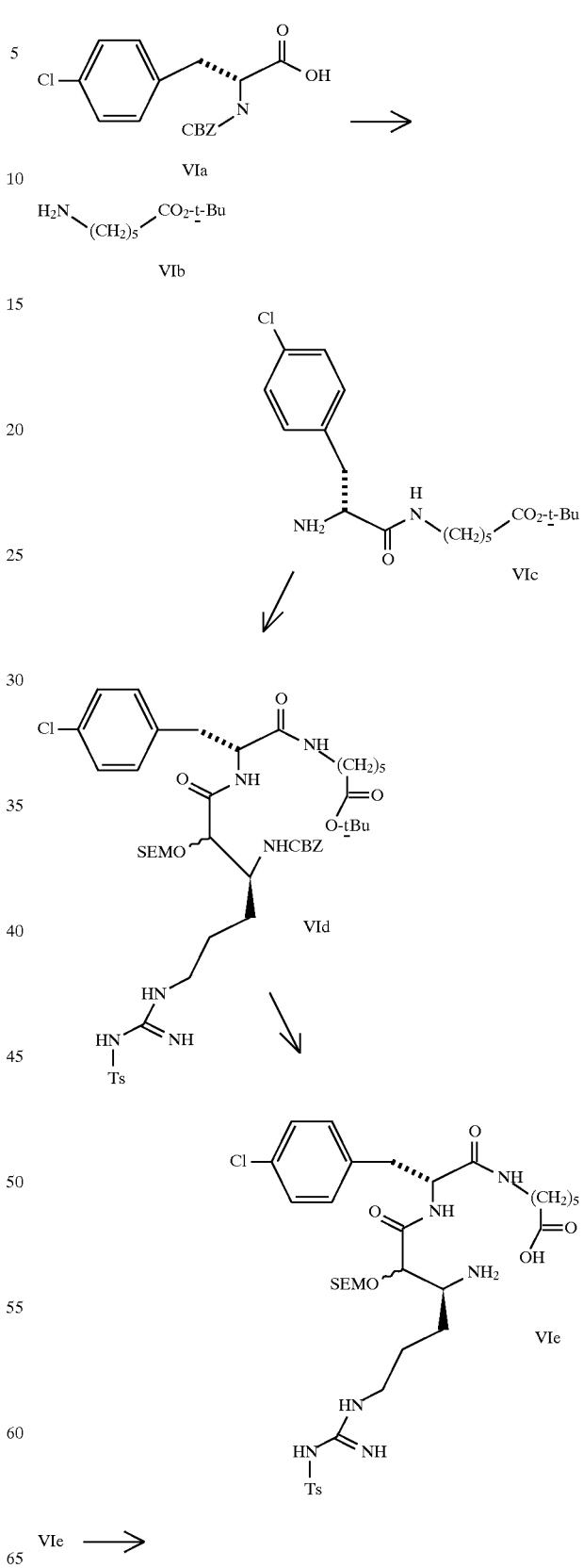

SCHEME VI

-continued
SCHEME VI

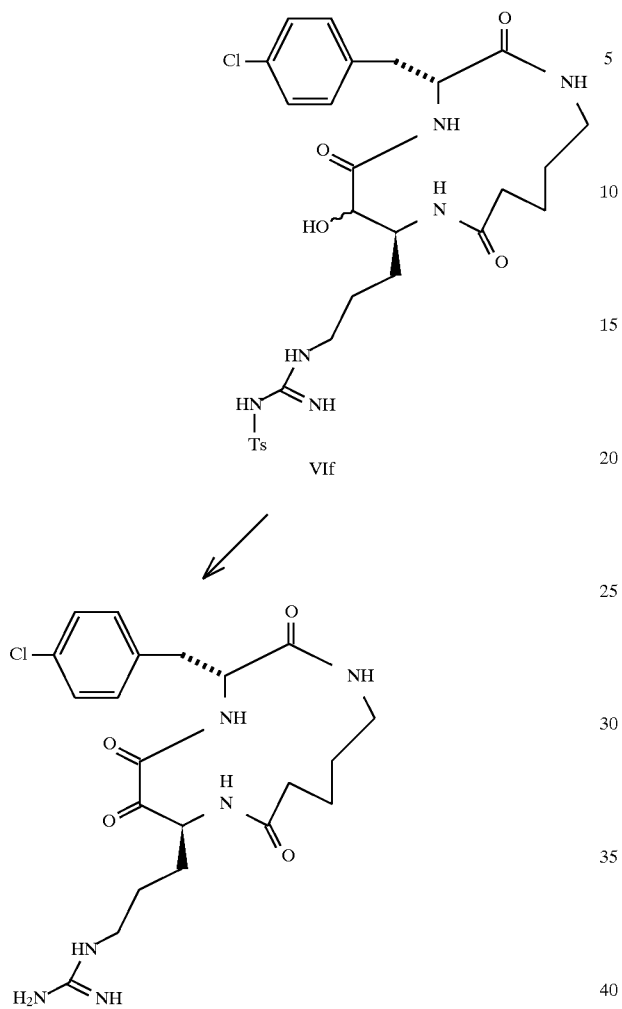

Scheme VII may be used to prepare the compounds of Formula III where m is 4, W is sulfur,
A is

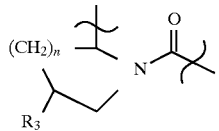

where $R_3$ is hydrogen and n is 1;
B is

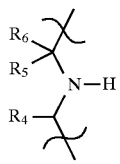

where $R_4$ is benzyl and $R_5$ is taken together with $R_6$ to form a carbonyl; and G is

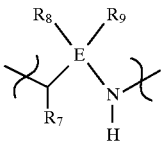

where E, $R_8$ and $R_9$ are taken together to form a carbonyl and $R_7$ is benzyl.

N-α-Fmoc-N-γ-tosyl-L-arginine is treated with carbonyidiimidazole at 0° C. in THF and reduced with DIBAL at about −48° C. to give the corresponding aldehyde. The cyanohydrin VIIb is produced by treating the aldehyde with KCN and $H_2O$ at room temperature over several days in ethyl acetate. Treatment of VIIb with gaseous HCl in an alcohol such as MeOH at about −40° to −15° C. over several hours gives the imidate VIIc. Treatment of the imidate with VIId (cysteine methyl ester hydrochloride) in an inert solvent such as $CH_2Cl_2$ at room temperature for 1–5 h gives the Fmoc protected amino alcohol VIIe. The hydroxy of VIIe can be converted to the trisilylalkyl ether with standard silylating agents such as t butyidimethylsilyltriflate and an organic base such as 2,6-lutidine at 0° C. The Fmoc group is removed by treatment with an organic base such as diethyl amine at room temperature over 2–5 h. The free amine can be protected as the N-Boc derivative by treatment with di-t-butyl dicarbonate in an inert solvent at 0 20 C. over 16 h to give the 4,5-dihydrothiazole intermediate VIIf. Intermediate VIIf can be oxidized to the thiazole by treatment with with an oxidizing agent such as $MnO_2$ in an inert solvent such as $CH_2Cl_2$ at room temperature over several hours. The isolated 5-carboalkoxy thiazole intermediate is saponified at room temperature with LiOH in dioxane/water to give the 5-carboxy thiazole derivative VIIg.

Derivative VIIg is coupled using HOBT/DCC to the C-protected tripeptide VIIh, where the peptide is prepared using any of the methods discussed in the previous schemes. Treatment with TFA removes the Boc group to give the coupled intermediate VIIi. This intermediate is treated at room temperature with BOP-Cl and DMAP in an inert solvent followed by removal of the silyl protecting group with $Bu_4NF/THF$ at room temperature to give the macrocycle VIIj. This intermediate is oxidized using Dess-Martin periodinane in an anhydrous aprotic solvent and deprotected using HF in the presence of a carbocation scavenger to give a compound of Formula III.

To produce compounds where W is nitrogen or oxygen, VIId is replaced with 2,3-diamino propionic acid methyl ester or serine ethyl ester respectively.

Intermediate VIIc is used to produce all of the compounds of Formula III. This intermediate can be used in place of 6-[[imino[4-methylbenzenesulfonyl)-amino]methyl]amino] 2-(R,S)-[[2-(trimethylsilyl)ethoxy]methoxy]-3(S)-[9-phenylmethoxycarbonyl)-amino]hexanoic acid or 6-[[imino [4-methylbenzenesulfonyl)-amino]methyl]amino]-2-(R,S)-[ [2-(trimethylsilyl)ethoxy]methoxy]-3(S)-[9-fluorenylmethoxycarbonyl)-amino]hexanoic acid in Schemes I through VIII with only minor modification to give the desired compounds.

SCHEME VII
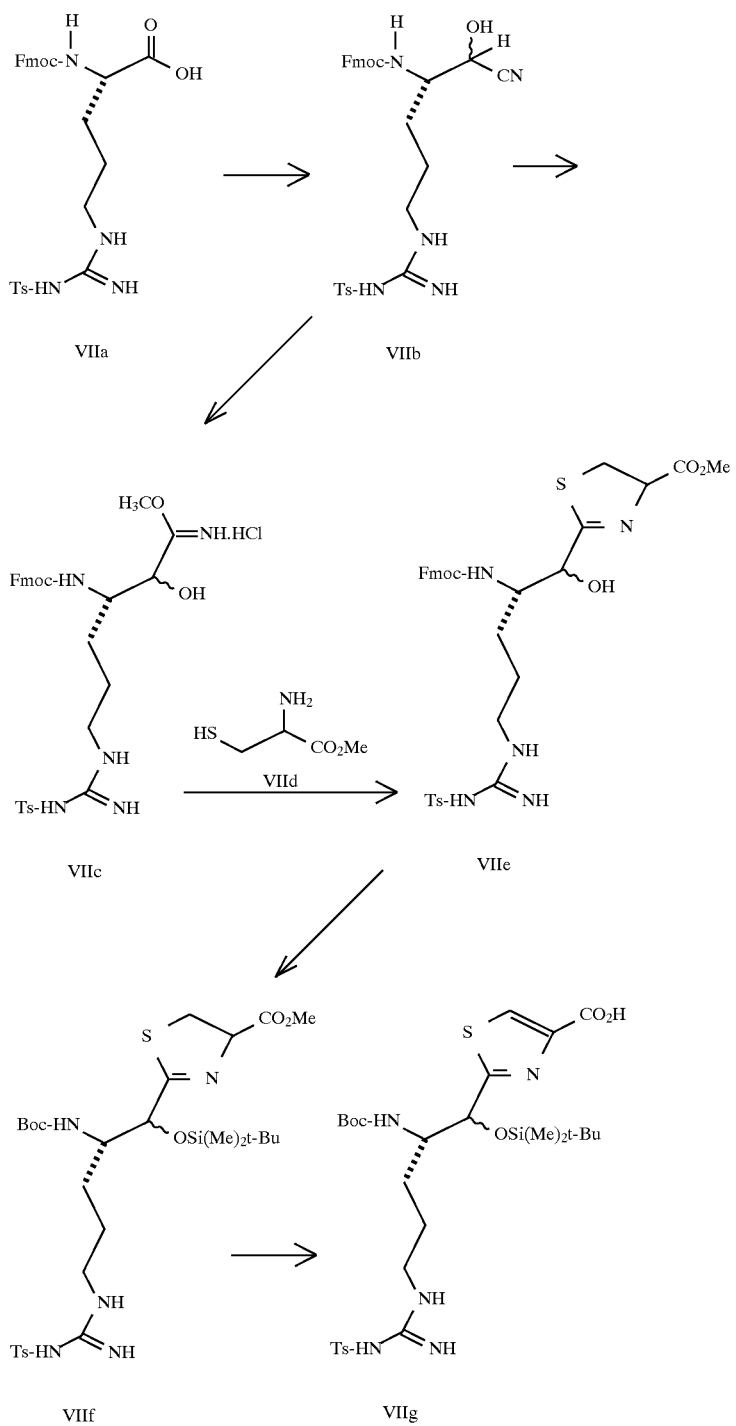

-continued
SCHEME VII
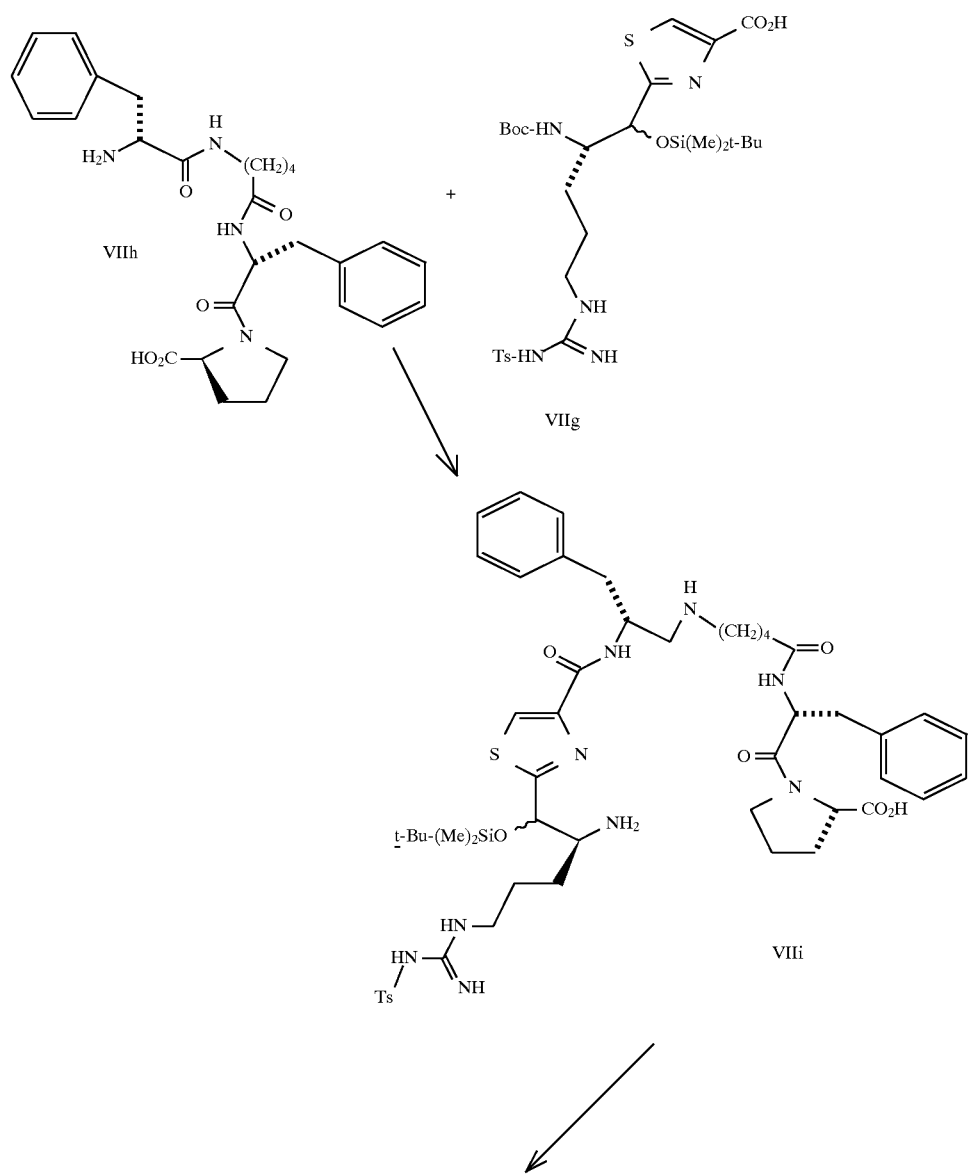

-continued
SCHEME VII

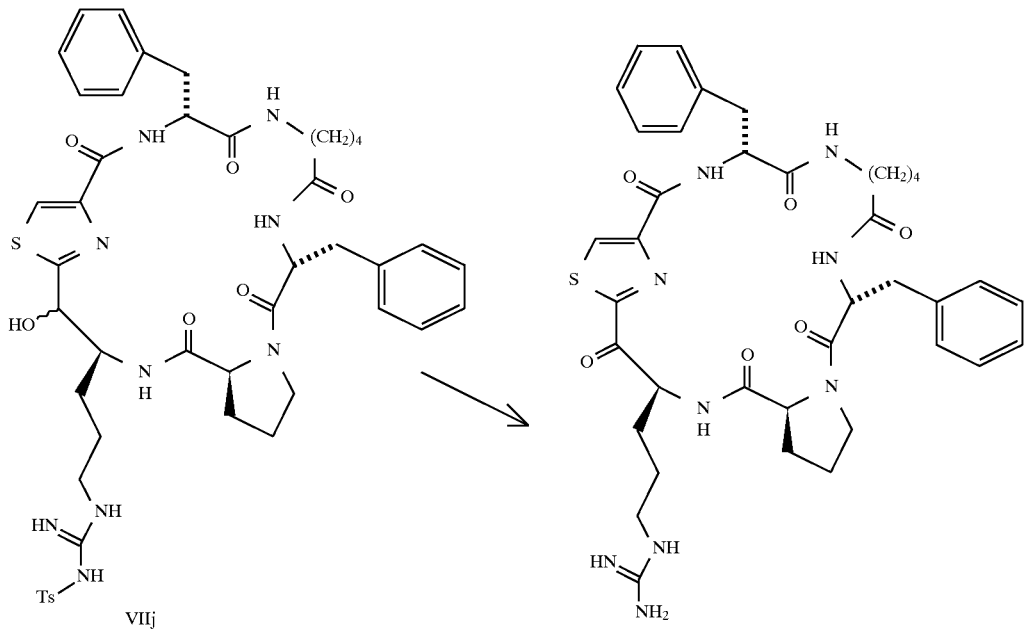

The compounds of the invention were tested for their ability to inhibit thrombin mediated hydrolysis. Two in vitro enzyme assays were performed to give both Michaelis-Menten kinetics or slow, tight-binding kinetics In addition, the compounds were tested in vitro for their ability to inhibit trypsin, as an indication of their selectivity Thrombin-catalyzed hydrolysis rates were measured spectrophotometrically using commercial human alpha-thrombin (American Diagnostica), a chromogenic substrate (Spectozyme® TH (H-D-HHT-Ala-Arg-pNA.2AcOH), American Diagnostica) in aqueous buffer (10 mM Tris, 10 mM Hepes, 150 mM NaCl, 0.1% PEG; pH 7.4), and a microplate reader (Molecular Devices). Changes in absorbance at 405 nm were monitored (Softmax, Molecular Devices), upon addition of enzyme, both with and without inhibitor present at 37° C. over 30 minutes. Inhibition constants (Ki) were determined by fixing the enzyme and inhibitor concentrations and varying the substrate concentration (1 nM thrombin, 5–100 μM Spectozyme® TH). Michaelis-Menton kinetics were applied to the initial reaction slopes using the program K Cat (Bio Metallics Inc.).

Trypsin-catalyzed hydrolysis rates were measured using the same method as the thrombin procedure. Bovine type 1 trypsin (Sigma) and Spectrozyme® TRY (Cbo-Gly-D-Ala-Arg-pNA.AcOH, American Diagnostics) replaced their thrombin equivalents in a concentration range of 3.2 U/ml trypsin and 0.1–0.3 mM Spectrozyme.

Compounds of the invention showed slow binding inhibition with thrombin which was demonstrated in the following assay. Serial dilutions of compounds and human alpha-thrombin (0.1 nM, American Diagnostica) were incubated at 25° C. for 4 h. A chromogenic substrate was added (50 μM Spectozyme® TH (H-D-HHT-Ala-Arg-pNA◊2AcOH), American Diagnostica) and the increase in absorbance at 405 nM was measured with a microplate reader (Molecular Devices) at 25° C. using an aqueous buffer (10 mM Tris, 10 mM Hepes, 150 mM NaCl, 0.1%PEG; pH 7.4). Data was collected over 4 h and plotted (MOD v. Time). A compound was determined to be slow binding if the plot for any compound at any concentration was concave.

Ki-slow was determined by measuring enzyme-catalyzed hydrolysis rates. A mixture of human alpha-thrombin (0.1 nM, American Diagnostica), substrate (50 μM Spectozyme® TH (H-D-HHT-Ala-Arg-pNA◊2AcOH), American Diagnostica), compound and aqueous buffer (10 mM Tris, 10 mM Hepes, 150 mM NaCl, 0.1% PEG; pH 7.4) was monitored over 4 h for changes in absorbance at 405 nM at 25° C. A vehicle mixture was run under the same condition and inhibition constants were determined by applying the data to the following equation: $P=v_s t-(1/k'(V_s-V_z)(1-\exp^{(-k't)})$. Plotting k' Vs. I gives Ki from the equation $k'=k_6(1+S/Km)+k_6/Ki(I)$. (Ref: Tight-Binding Inhibitors-I. Sungman Cha, Biochemical Pharmacology 1995. Vol 24 pp2177–2185). The $K_i$s and $K_i$-slow (μM) for representative compounds are listed in Table A. Cyclotheonamide, N-Me PPACK aldehyde ("GYKI-14766/LY-294468, Anticoagulant Thrombin Inhibitor", Drugs Future 1993, 18, 1159–1160) and argatroban ("Argaroban/Novastan/Slonnon, Anticoagulant Thrombin Inhibitor., Drugs Future 1990, 15, 1115–1116) were used as reference standards and their values are listed below. The compound numbers in the table correspond to the examples described hereinafter.

TABLE A

| Cpd # | Thr $K_i$ | Trp $K_i$ | Thr $K_i$-slow |
|---|---|---|---|
| 2 | 0.35 ± 0.1 (N = 8) | 0.45 ± 0.37 (N = 6) | |
| 15 | 0.15 ± 0.1 (N = 10) | 0.026 ± 0.018 (N = 8) | |
| 14 | 1.61 ± 1.32 (N = 10) | 0.011 ± 0.003 (N = 5) | |
| 3 | 0.021 ± 0.012 (N = 6) | 0.015 ± 0.0038 (N = 6) | |
| 11 | 0.0031 ± 0.0008 (N = 5) | 0.004 ± 0.0018 (N = 6) | |
| 18 | 3.8 ± 0.2 (N = 3) | 0.31 ± 0.01 (N = 3) | |
| 16 | 85.9 ± 16.3 (N = 3) | 0.62 ± 0.48 (N = 8) | |
| 7 | 0.2 ± 0.072 (N = 7) | 0.039 ± 0.025 (N = 5) | |
| 6 | 0.021 ± 0.005 (N = 6) | 0.0068 ± 0.005 (N = 8) | |
| 5 | 0.09 ± 0.0086 (N = 6) | 0.085 ± 0.029 (N = 5) | |
| 1 | 0.014 ± 0.001 (N = 5) | 0.045 ± 0.036 (N = 6) | |
| 10 | 0.015 ± 0.004 (N = 6) | 0.025 ± 0.02 (N = 4) | |
| 8 | 1.8 ± 1 (N = 6) | 0.28 ± 0.02 (N = 6) | 491.996 ± 268.809 (N = |
| 17 | 0.018 ± 0.004 (N = 6) | 0.0029 ± 0.0015 (N = 5) | |
| 21 | 0.092 ± 0.046 (N = 5) | 0.022 ± 0.014 (N = 6) | 4.705 ± 1.509 (N = 2) |
| 9 | 0.0099 ± 0.0017 (N = 7) | 0.0021 ± 0.0011 (N = 5) | |
| 4 | 0.16 ± 0.06 (N = 9) | 0.013 ± 0.005 (N = 6) | |
| 22 | no activity at 50 μM | | |
| 19 | 0.0053 ± 0.0026 (N = 6) | 0.0025 ± 0.00075 (N = 5) | |
| 12 | 1 ± 0.12 (N = 6) | 0.017 ± 0.0073 (N = 6) | |
| 20 | 0.019 ± 0.0044 (N = 6) | 0.0053 ± 0.0026 (N = 5) | 1.362 ± 0.7 (N = 3) |
| 23 | 1 ± 0.4 (N = 6) | 0.066 ± 0.026 (N = 6) | |
| 13 | 0.0023 ± 0.0005 (N = 6) | 0.0015 ± 0.0009 (N = 3) | |
| CtA | .170 ± 0.08 | 23.0 | 4.0 ± 1.9 (N = 4) |
| N-Me-PPAC | 0.010 | 0.0039 | |
| Argatroban | 0.010 | 2.9 | |

As indicated by Table A, the compounds of Formula I may be used in pharmaceutical compositions to treat patients (humans and other primates) with thrombotic disorders in a similar manner as known heparins and coumarins. The compounds can be administered by any parenteral route (intravenous, intraperitoneal, subcutaneous, dermal patch), where the preferred route is intravenous infusion. Infusion doses can range from about 0.1–300 μg/kg/min of inhibitor, admixed with a pharmaceutical carrier over a period ranging from several minutes to several days.

The pharmaceutical compositions can be prepared using conventional pharmaceutical excipients and compounding techniques. Oral dosage forms may be elixers, syrups, capsules tablets and the like. Where the typical solid carrier is an inert substance such as lactose, starch, glucose, methyl cellulose, magnesium sterate, dicalcium phosphate, mannitol and the like; and typical liquid oral excipients include ethanol, glycerol, water and the like. All excipients may be mixed as needed with disintegrants, diluents, granulating agents, lubricants, binders and the like using conventional techniques known to those skilled in the art of preparing dosage forms. Parenteral dosage forms may be prepared using water or another sterile carrier.

Typically the compounds of Formula I are isolated and used as their pharmaceutically acceptable salts. Examples of such salts include hydrobromic, hydroiodic, hydrochloric, perchloric, sulfuric, maleic, fumaric, malic, tartatic, citric, benzoic, mandelic, methanesulfonic, hydroethanesulfonic, benzenesulfonic, oxalic, pamoic, 2-naphthalenesulfonic, p-toluenesulfonic, cyclohexanesulfamic and saccharic.

In addition to the treatment of thrombotic disorders, the compounds of Formula I may be used to prevent coagulation of stored blood samples and as coatings on medical devices such as stents and orthopedic devices. Generally they may be used in any circumstance where one seeks to inhibit coagulation by placing the compounds in contact with the medium containing thrombin. Those experienced in the use of anticoagulant agents, may find a variety of other uses for the thrombin inhibitors of this invention. These uses are considered to be within the scope of this invention, for this invention contemplates the use of compounds of Formula I as antithrombotic agents.

Yet another use for the compounds of the invention is as trypsin inhibitors. Inhibitors of trypsin have been used clinically in the treatment of pancreatic disorders, such as pancreatitis. The $IC_{50}$ values for the compounds of the invention compare favorably with the pancreatic agents camostat mesilate and nafamostat ($IC_{50}$ s, $1\times10^{-8}$ and $1.3\times10^{-8}$ respectively). The compounds of Formula I may be used in the same manner as those therapeutic agents.

Although all of the claimed compounds are useful as thrombin or trypsin inhibitors, the preferred compounds of Formula I include

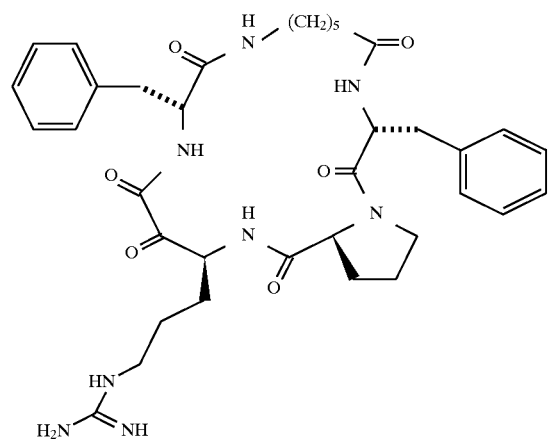

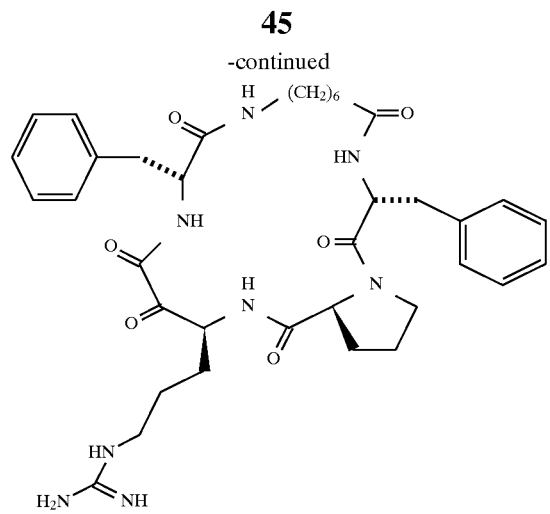
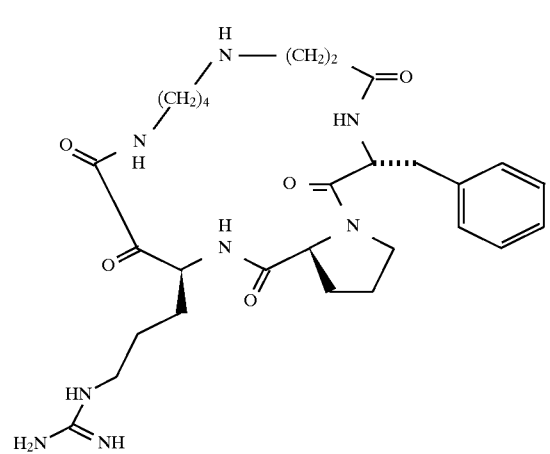
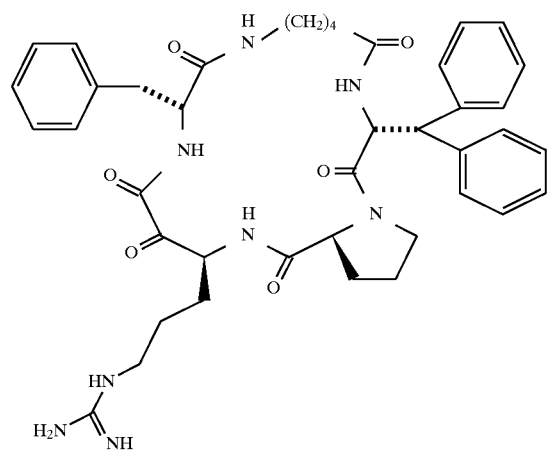
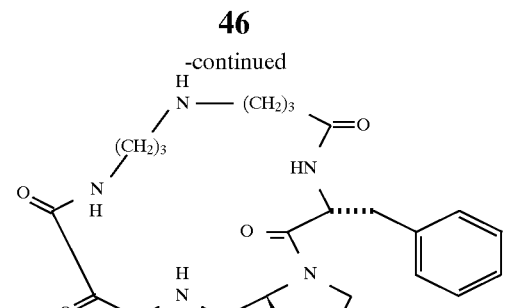
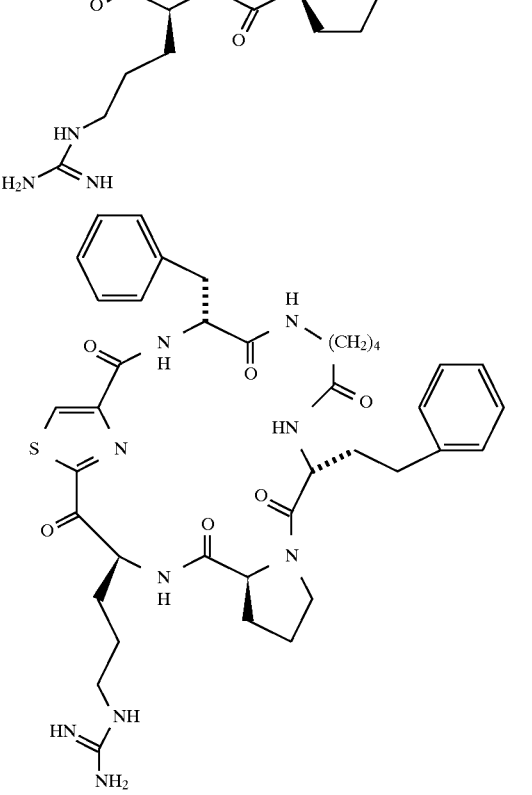
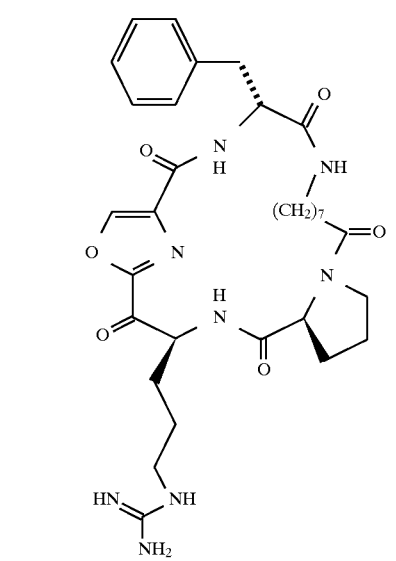
and

-continued

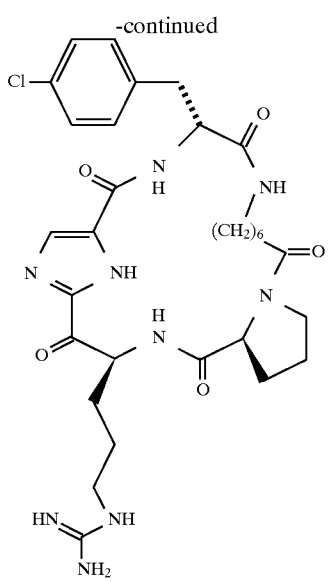

With respect to compounds of Formulas I and II. the particularly preferred substituents are as follows. The particularly preferred "A"s are

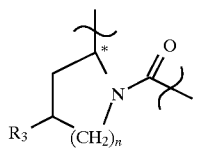

where n is 1, $R_3$ is hydrogen and the preferred stereochemistry of the starred carbon is S.

The particularly preferred "B"s are

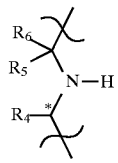

where $R_5$ and $R_6$ are taken with the carbon to which they are each attached to form a carbonyl; and $R_4$ is naphthyl methyl, diphenyl methyl, phenyl$C_{1-5}$alkyl or substituted phenyl$C_{1-5}$alkyl where the phenyl substituents are chlorine or fluorine. The preferred stereochemistry of the starred (*) carbon is R.

The particularly preferred "G"s are

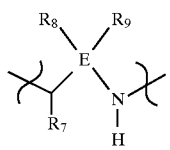

where $R_8$ and $R_9$ are taken with the carbon to which each is attached to form a carbonyl; and $R_7$ is naphthylmethyl, diphenylmethyl, phenyl$C_{1-5}$alkyl or substituted phenyl$C_{1-5}$alkyl where the phenyl substituents are chlorine or fluorine. The ring size of the macrocycle is determined by A, B, G and m, where a ring size of 15 to 25 is particularly preferred.

With respect to the compounds of Formula III, the particularly preferred "W" is sulfur. All other particularly preferred substituents are as described for Formulas I and II.

In order to illustrate the invention the following examples are included. These examples do not limit the invention. They are only meant to suggest a method of practicing the invention. Those skilled in the art may find other methods of practicing the invention, which are obvious to them. However, those methods are deemed to be within the scope of this invention.

EXAMPLE 1

5R, 18S, 21S-N-[3-(4, 7, 16, 17, 20-PENTAOXO-5-PHENETHYLEICOSAHYDRO-3a, 6, 15, 19-TETRAAZACYCLOPENTACYCLONON-ADECENE-18-YL) PROPYL] GUANIDINE

Step 1a

1a

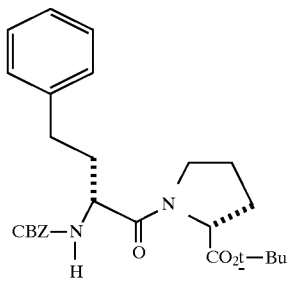

A solution of CBZ-D-homophenylalanine 5.6 g (18 mmol), ProO-t-Bu (3.4 g, 19.8 mmol) and HOBT, (3.65 g, 27 mmol) in $CH_3CN$ (70 mL) was stirred for 20 min, treated with a solution of DCC (4 g, 19.8 mmol) in $CH_3CN$ (30 mL) and stirred overnight. This mixture was filtered, the filtrate was concentrated and dissolved in $CHCl_3$ (400 mL). This solution was washed with successive portions of 2% $Na_2CO_3$(aq) (100 mL) and brine (100 mL). The resulting organic layer was dried ($Na_2SO_4$), concentrated in vacuo and purified by flash column chromatography (silica, $CHCl_3$) to afford 1a as an oil: (8.4g).

Step 1b

1b

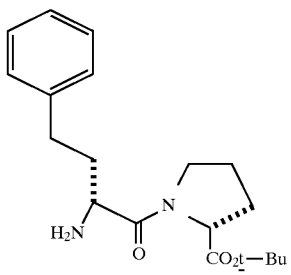

A mixture 1a (5.0 g) and Pd(OH)$_2$—C in MeOH (100 mL) was shaken under 20 psig for 1.5 h. The catalyst was filtered, and the filtrate concentrated to give the free amine 1b, as an oil (61.6 g).

Step 1c

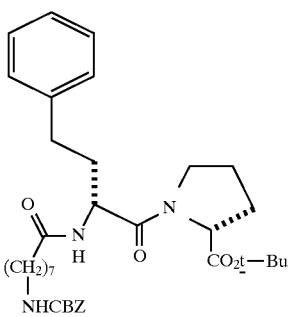

A solution of DCC (3.8 g, 18.5 mmol) in CH$_3$CN (40 mL) was added to a stirred mixture of 1b (6.2 9, 18.5 mmol) 8-carbobenzoxyaminooctanoic acid (4.94 g, 16.8 mmol) and HOBT (3.4 g, 25.2 mmol) in CH3CN (300 mL). The resulting mixture was stirred for 16 h, filtered and concentrated in vacuo. The residue was dissolved in CHCl$_3$, washed sequentially with 5% Na$_2$CO$_3$(aq) and brine, dried (Na$_2$SO$_4$), and concentrated in vacuo . The residue was purified by flash column chromatography (ether-MeOH; 100%→95:5) to give ester 1c as an oil: (7.8 g, 70%); m/e=607 (MH$^+$).

Step 1d

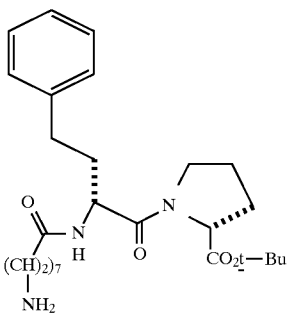

A mixture of 1c, (7.8 g, 12.8 mmol), 20% Pd(OH)$_2$/C (5.0 g) and 150 mL of MeOH was shaken under 20 psig of H$_2$ for 3 h. The mixture was filtered and concentrated to give the amine 1d as an oil: (5.5 g, 91%), m/e=474 (MH$^+$).

Step 1e

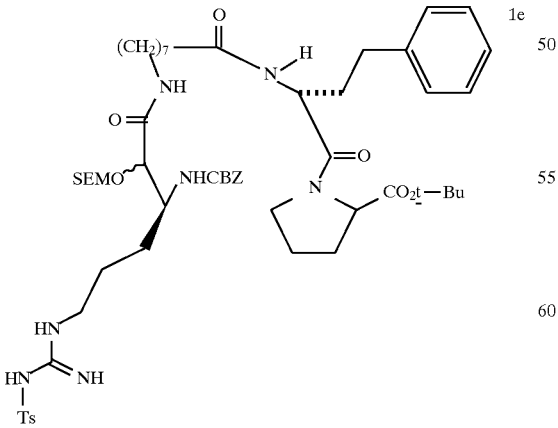

A solution of DCC (0.91, 4.4 mmol) in DMF (15 mL) was added to a solution of 6-[[imino[4-methylbenzenesulfonyl) amino]methyl]amino]-2-(R,S)-[[2-(trimethylsilyl)ethoxy] methoxy]-3(S)-[9-phenylmethoxycarbonyl)-amino] hexanoic acid, (2.5 g, 4.0 mmol: Maryanoff et al. *Journal of the American Chemical Society* 1995, 117, 1225–39), amine 1d (2.0 g, 4.4 mmol) and HOBT (0.8 g) in DMF (150 mL). This mixture was stirred overnight, and filtered. The filter cake was washed with CH$_3$CN, and the filtrate was concentrated in vacuo. The residue was purified by flash column chromatography (silica gel, 100% CHCl$_3$, then 2% MeOH—CHCl$_3$) to give ester 1e as a foam: (3.4 g 78%); m/e=1078 (MH$^+$).

Step f

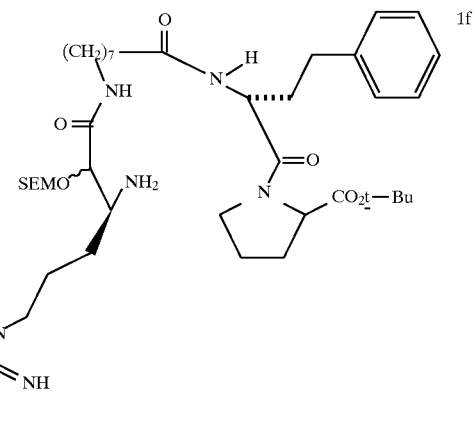

A solution of 1e (3.3 g) in MeOH (50 mL) was treated with 20% Pd(OH)$_2$/C (2.0 g) and shaken under 20 psig of H$_2$ for 3 h. The mixture was filtered and concentrated to the ester 1f as a foam: (2.7 g); m/e=944 (MH$^+$).

Step g

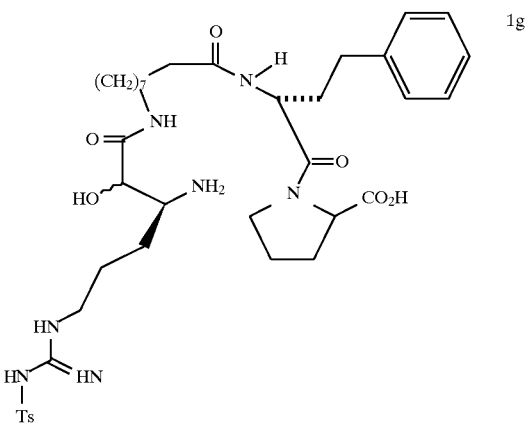

A solution 1f (2.6 g) in CH$_2$Cl$_2$ (10 mL) was added to a solution of 1:1 CH$_2$Cl$_2$:trifluoroacetic acid (40 mL) at 0° C. and stirred for 2.5 h. Volatiles were removed under a stream of N$_2$, and the resulting gum was triturated three times with ether to give the acid 1g as a white solid: (2.5 g); m/e=758 (MH$^+$).

Step h

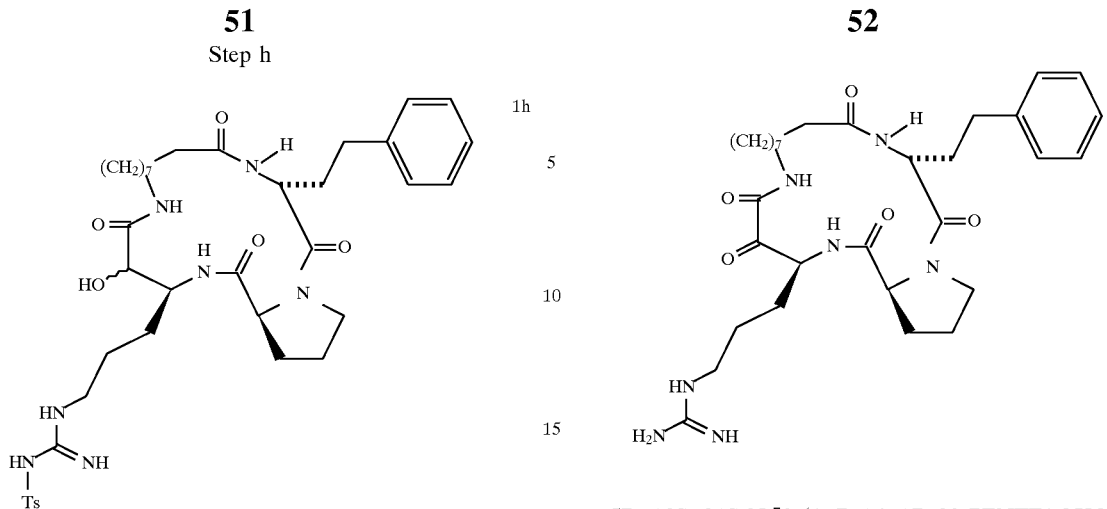

A mixture of (1.2 g, 1.38 mmol) in 1.4 L of $CH_2Cl_2$ was treated with DMAP (0.93 g, 7.6 mmol), and stirred for 20 min. BOP-Cl (0.1, 2.76 mmol) was added and the mixture was stirred for another 2 h and concentrated in vacuo. The residue was dissolved in $CH_2Cl_2$ (500 mL) and washed twice with 10% citric acid (aq)(2×250 mL). The organic layer was washed with brine, dried ($Na_2SO_4$), filtered, and concentrated in vacuo . The residue was purified by flash column chromatography ($CHCl_3$-MeOH; 100%→90%; silica gel) to give the coupled intermediate 1 h: (600 mg, 81%); m/e=740 ($MH^+$).

Step i

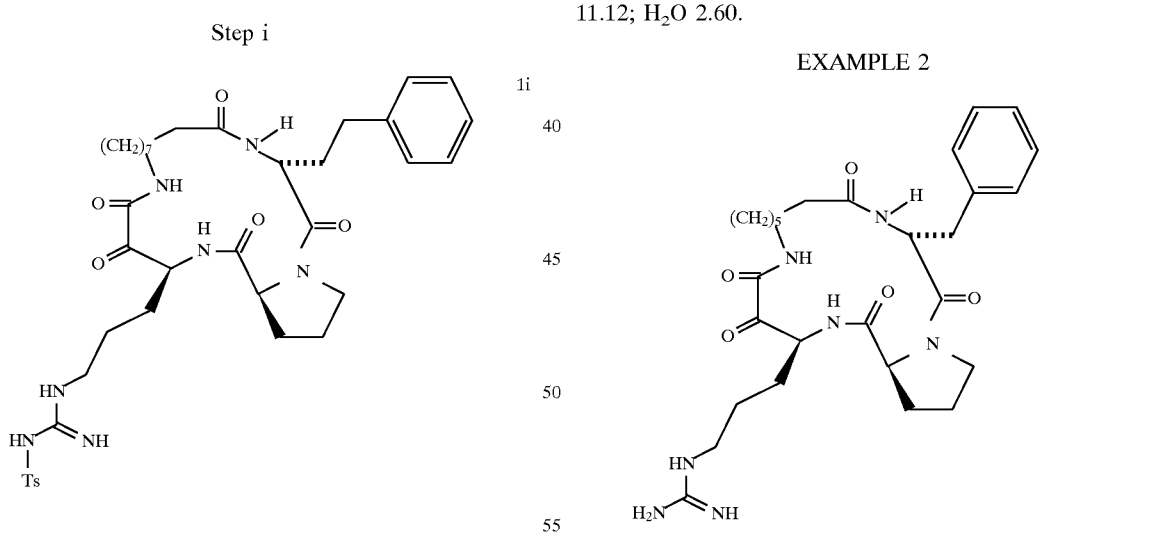

Dess-Martin periodinane (499 mg, 1.2 mmol) was added to a stirred solution of 1h (580 mg, 0.78 mmol) in $CH_2Cl_2$ (50 mL) at room temperature. This mixture was stirred for 1.5 h, treated with an excess of 25% $Na_2S_2O_4$ (aq) in $NaHCO_3$ (sat'd. aq) and stirred for another 5 min. The aqueous layer was extracted with several portions of $CH_2Cl_2$ and the combined organic extracts were washed twice with NaCl (sat'd, aq), dried ($Na_2SO_4$), filtered and concentrated to give the diketone 1i as a white solid: (495 mg); m/e=738 ($MH^+$).

5R, 18S, 21S-N-[3-(4, 7, 16, 17, 20-PENTFAOXO-5-PHENETHYLEICOSAHYDRO-3a, 6, 15, 19-TETRAAZACYCLOPENTACYCLONON-ADECENE-18-YL) PROPYL] GUANIDINE

COMPOUND 1

A suspension of 1i (480 mg, 0.65 mmol) in anisole (3 mL) was cooled to −78° C. and treated with anhydrous HF ( ca. 10 mL) using a standard HF apparatus. This mixture was stirred at 0° C. for 3.5 h, concentrated in vacuo and triturated twice with 25 mL portions of ether. A solid was collected, washed with ether, and purified by reverse-phase HPLC (MeCN-water-TFA, 35:65:0.2). The resulting solid was lyophilized to give the title compound as a white solid: 272 mg; mp 50° C.; FAB-MS m/e 584 ($MH^+$); Anal Calcd. for $C_{30}H_{45}N_7O_5 \cdot 2.5\ CF_3CO_2H \cdot 1.25\ H_2O$; Calcd.: C, 47.16; H, 5.65; N, 11.00; $H_2O$, 2.53; Found: C, 46.90; H, 5.23; N, 11.12; $H_2O$ 2.60.

EXAMPLE 2

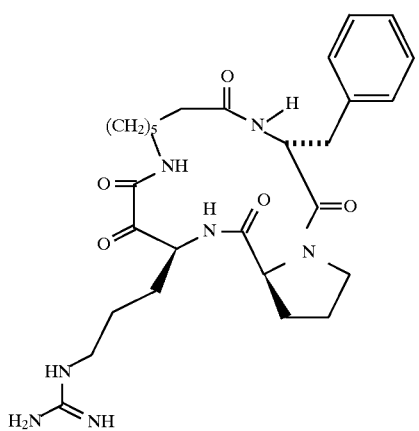

5R, 16S, 19S-N-[3-(5-BENZYL-4, 7, 14, 15, 18-PENTAOXOOCTADECAHYDRO)-3a, 16, 13, 17-(TETRAAZACYCLOPENTACYCLOHEPTADECEN-16-YL)PROPYL]-GUANIDINE DI-TRIFLUOROACETIC ACID SESQUIHYDRATE.

COMPOUND 2

Compound 2 was prepared using the general method of Example 1. CBZ-D-PheOH replaced CBZ-D-homophenylalanine in Step 1a and 5-carbobenzoxyami nopentanoic acid replaced 8-carbobenzoxyaminooctanoic acid in Step 1c to give the title compound as a solid. FAB-MS m/e 541 (MH⁺); Anal. Calc'd for $C_{27}H_{39}N_7O_5$.2 $(C_2HF_3O_2)$.1.5 $H_2O$; Calc'd: C, 46.73; H, 5.57; N, 12.31, $H_2O$, 3.39; Found: C, 46.71; H, 5.73; N, 12.78; $H_2O$, 3.52.

EXAMPLE 3

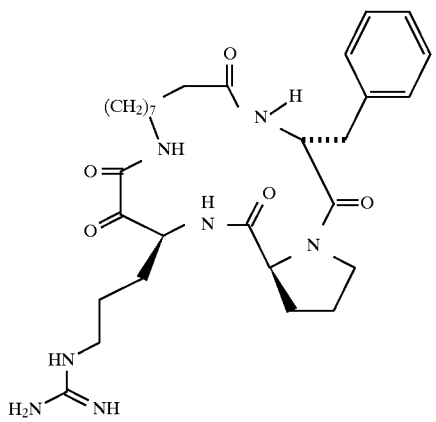

2S, 5S, 18R-N-[3-(18-BENZYL)-3,6,7,16,19-(PENTAOXOEICOSAHYDRO)-1A, 4, 8, 17-(TETRAAZACYCLOPENTACYCLONONODECEN-5-YL)PROPYL] GUANIDINE TRIFLUOROACETIC ACID HYDRATE.

COMPOUND 3

Compound 3 was prepared following the method of Example 1 with only slight modifications. CBZ-D-PheOH replaced CBZ-D-homophenylalanine in Step 1a to give the title compound as a solid. FAB-MS m/z 570, (MH⁺) Anal. Calc'd for $C_{29}H_{43}N_7O_5$.2.5$C_2HF_3O_2$.$H_2O$; Calc'd: C, 46.79; H, 5.49; N, 11.23; $H_2O$, 2.06; Found: C, 47.05; H, 5.43; N, 11.29; $H_2O$, 2.25.

EXAMPLE 4

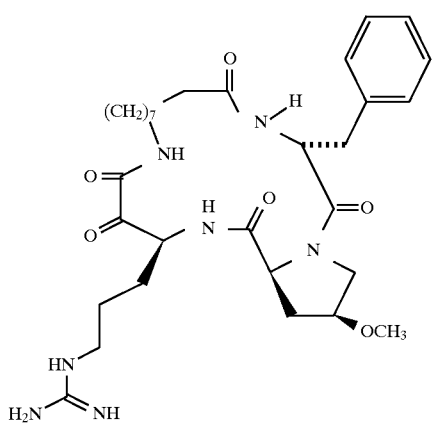

2S, 5R, 18S, 21S-[3-(5-BENZYL-2METHOXY-4, 7, 16, 17, 20-PENTAOXOEICOSAHYDRO-3a, 6, 15, 19-TETRMZACYCLOPENTACYCLONON-ADECEN-18-YL) PROPPYL] GUANIDINE TRIFLUOROACETIC ACID HYDRATE

COMPOUND 4

Compound 4 was prepared following the method of Example 1 with only slight modifications. CBZ-D-PheOH replaced CBZ-D-homophenylalanine in Step 1a and cis-methoxyproline (prepared according to Barlos, K., et al. *Tetrahedron Lett*. 1983, 39, 475) replaced ProO-t-Bu in the same step to give the title compound as a solid: FAB-MS m/z 600 (MH⁺); Anal. Calc'd for $C_{30}H_{45}N_7O_6$.2.25 $C_2HF3O_2$.1.5 $H_2O$; Calc'd: C, 46.91; H, 5.73; N, 11.10; $H_2O$, 3.05; Found: C, 46.90; H, 6.03; N, 11.44; $H_2O$, 3.00.

EXAMPLE 5

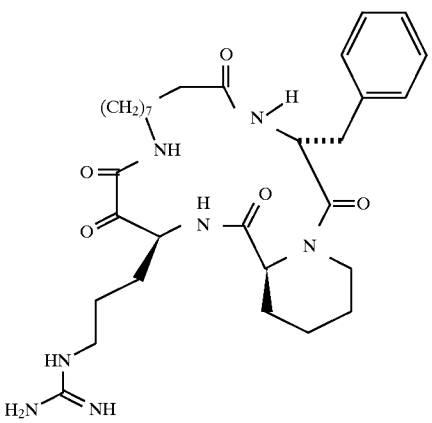

6R, 19S, 22S-N-[3-(6-BENZYL-5, 8, 17, 18, 21-PENTAOXODOCOSAHYDRO-4a, 7, 16, 20-TETRAAZABENCBZOCYCLONONADECEN-19-YL) PROPYL] GUANIDINE TRIFLUOROACETIC ACID HYDRATE

COMPOUND 5

Compound 5 was prepared following the method of Example 1 with only slight modifications. CBZ-D-PheOH replaced CBZ-D-homophenylalanine in Step 1a and L-pipecolinic acid replaced ProO-t-Bu in the same step to give the title compound as a solid: FAB-MS m/z 584 (MH⁺); Anal. Calcd for $C_{30}H_{45}N_7O_5$.2.0 $C_2HF_3O_2$.1.0 $H_2O$; Calc'd: C, 49.21; H, 5.95; N, 11.82; $H_2O$, 2.17; Found: C, 49.28; H, 5.66; N, 11.67, $H_2O$, 2.56.

EXAMPLE 6

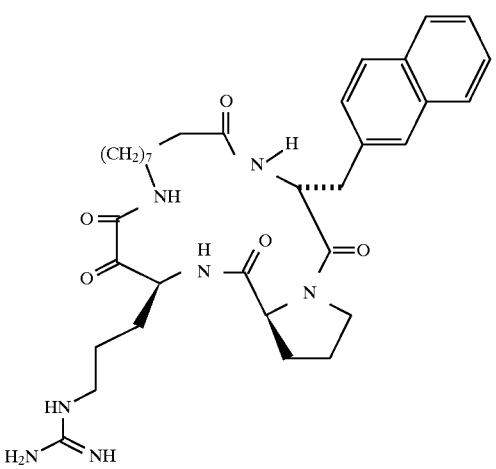

5R, 2S, 18S-N-[3-(5-NAPTHALEN-2-YLMETHYL-4, 17, 16, 17, 20-PENTAOXOEICOSAHYDRO-3a, 6, 15, 19-TETRAAZACYCLOPENTACYCLONONADECEN-18-YL)PROPYL] GUANIDINE TRIFLUOROACETATE HYDRATE

COMPOUND 6

Compound 6 was prepared following the method of Example 1 with only slight modifications. CBZ-D-2-napthylalanine replaced CBZ-D-homophenylalanine in Step 1a to give the title compound as a solid: FAB-MS m/z: FAB-MS m/z 620 (MH$^+$); Anal. Calc'd for $C_{33}H_{45}N_7O_5 \cdot 1.5$ $C_2HF_3O_2 \cdot 1.75$ $H_2O$; Cacl'd: C, 51.80; H, 5.93; N, 11.59; $H_2O$, 3.19; Found: C, 51.44; H, 5.95; N, 11.44; $H_2O$, 3.23.

EXAMPLE 7

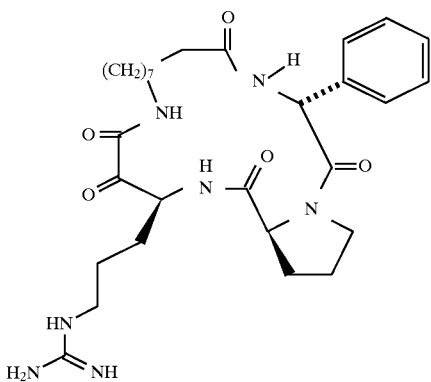

3S, 16R, 19S-N-[3-(1, 4, 5, 14, 17-PENTAOXO-16-PHENYL-2, 6, 15, 18-TETRAAZACYCLOPENTACYCLONONADECAN-3-YL)PROPYL] GUANIDINE TRIFLUOROACETIC ACID HYDRATE

COMPOUND 7

Compound 7 was prepared following the method of Example 1 with only slight modifications. CBZ-D-phenylglycine replaced CBZ-D-homophenylalanine in Step 1a to give the title compound as a solid: FAB-MS m/z 556 (MH$^+$); Anal; Calcd for $C_{28}H_{41}N_7O_5 \cdot 1.75$ $C_2HF_3O_2 \cdot 1.5$ $H_2O$; Calc'd: C, 48.37; H, 5.90; N, 12.53; H2O 3.45; Found: C, 48.40; H, 5.95; N, 12.52; H2O, 3.64.

EXAMPLE 8

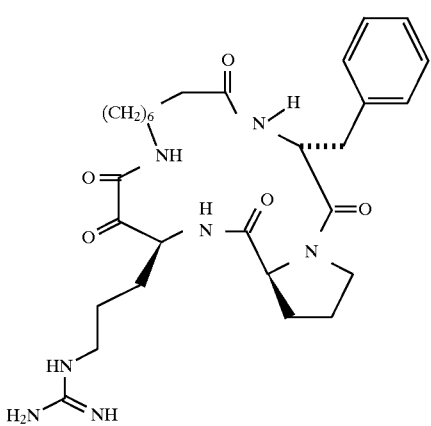

5R, 17S, 19AS-N-[3-(5-BENZYL-4, 7, 15, 16, 19-PENTAOXOOCTADECAHYDRO-3a, 6, 14, 18-TETRAAZACYCLOPENTACYCLOOCTADECEN-17-YL)PROPYL] GUANIDINE TRIFLUOROACETIC ACID HYDRATE

COMPOUND 8

Compound 8 was prepared using the general method of Example 1. CBZ-D-PheOH replaced CBZ-D-homophenylalanine in Step 1a and 7-carbobenzyloxyaminoheptanoic acid replaced 8-carbobenzoxyam inooctanoic acid in Step 1c to give the title compound as a solid: FAB-MS m/z 556 (MH$^+$); Anal. Calc'd for $C_{28}H_{41}N_7O_5 \cdot 1.5 C_2HF_3O_2 \cdot 2.0 H_2O$; Calc'd: C, 48.82; H, 6.15; N, 12.85, $H_2O$, 4.72; Found: C, 48.68; H, 6.07; N, 12.74, $H_2O$, 4.83.

EXAMPLE 9

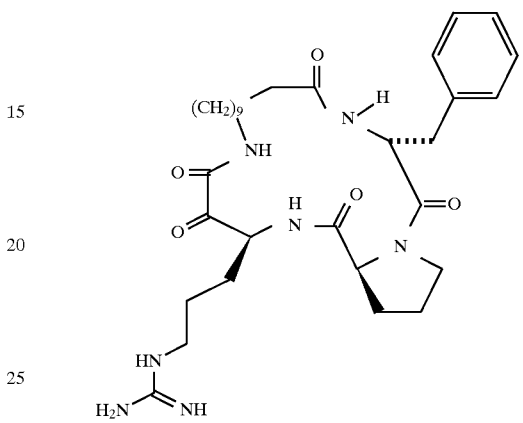

5R, 20S, 23S-[3-(5-BENZYL-4, 7, 18, 19, 22-PENTAOXOCYCLOEICOSAHYDRO-3A, 6, 17, 21-TETRAAZACYLOPENTACYCLOHENEI-COSEN-20-YL)PROPYL]GUANIDINE TRIFLUOROACETIC ACID HYDRATE

COMPOUND 9

A slurry of 9-cyanopelargonic acid (8.6 g, 48 mrnol), a catalytic amount 5%Rh/Al$_2$O$_3$, and 200 mL of 2.0N NH$_3$-EtOH was shaken under 50 psig of H2 pressure for 6 h, then filtered through dicalite. The filter pad was washed with 100 mL of hot 1:1 MeOH—H$_2$O, and the combined filtrates were concentrated to give 6.1 g of 10-aminodecanoic acid. The crude product (5.7 g) was dissolved in 15.5 mL of 2N NaOH and treated simultaneously with 23 mL of 2N NaOH and 5.8 g of carbobenzoxychloride at 0° C. with vigorous stirring over 0.5 h. Water and 2N NaOH were added as needed to maintain stirring and a pH between 10–14. After stirring for 2.5 h, the reaction was diluted with 400 mL of H$_2$O and filtered through dicalite. The filtrate was acidified (pH 2) with H$_2$SO$_4$, then extracted with ether. The combined ether extracts were dried (Na$_2$SO4), filtered and concentrated. The residue was dissolved in CH3CN, filtered, and the filtrate concentrated to afford 5.3 g of 10-(N-carbobenzoxy)-aminodecanoic acid which was used without further purification: FAB-MS m/z 322 (MH$^+$).

Compound 9 was prepared using the general method of Example 1. CBZ-D-PheOH replaced CBZ-D-homophenylalanine in Step 1a and 10-(N-carbobenzoxy)-aminodecanoic acid replaced 8-carbobenzoxyaminooctanoic acid in Step 1c to give the title compound as a solid: FAB-MS m/z 598 (MH$^+$); Anal Calc'd for $C_{31}H_{47}N_7O_5 \cdot 1.75 C_2HF_3O_2 \cdot 1.75 H_2O$; Calc'd: C, 50.00; H, 6.35; N, 11.83; H$_2$O, 3.80; Found: C, 49.62; H, 6.23; N, 11.93; H$_2$O, 3.46.

EXAMPLE 10

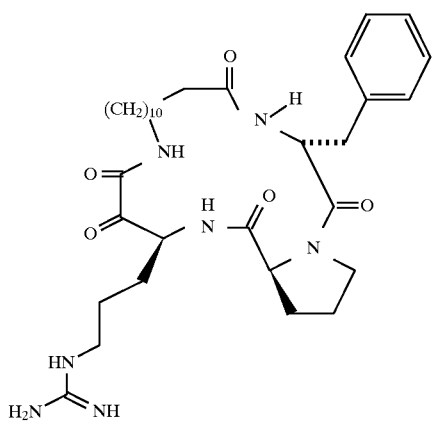

21S, 24S, 27R-N-[3-(5-BENCBZYL-4, 7, 19, 20, 23-PENTAOXOTETRACOSAHYDRO-3a, 6, 18, 22-TETRAACBZACYCLOPENTACYCLODO COSEN- 21-YL)PROPYL]GUANIDINE

COMPOUND 10

Compound 10 was prepared using the general method of Example 1. CBZ-D-PheOH replaced CBZ-D-homophenylalanine in Step 1a and 11-carbobenzoxyaminoundecanoic acid replaced 8-carbobenzoxyaminooctanoic acid in Step 1c to give the title compound as a solid: FAB-MS m/z 612 (MH$^+$); Anal Calc'd for $C_{32}H_{49}N_7O_5 \cdot 1.75\ H_2O \cdot 1.5\ C_2HF_3O_2$; Calc'd: C, 51.62; H, 6.68; N, 12.05; $H_2O$, 3.93; Found: C, 51.83; H, 6.12; N, 11.98; $H_2O$, 3.93

EXAMPLE 11

Preparation of Compound 11

Step 11a

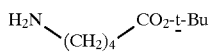   11a

Carbobenzoxy chloride (271 mL, 1.9 mol) and 4N NaOH (475 mL) were added simultaneously to a solution of 6-aminopentanoic acid (100 g, 0.76 mol) in 4N NaOH (aq.) (190 mL) at such a rate as to maintain the temperature $\leq 10°$ C. The reaction was stirred an additional 2 h at 0°–5° C. while the pH was maintained between 10 and 12. The mixture was then diluted with $H_2O$ (250 mL) and extracted four portions of ether (250 mL). The aqueous extract was acidified with 3N $H_2SO_4$ (pH=3), and extracted repeatedly with $CH_2Cl_2$. The organic extracts were combined and washed with brine, dried ($Na_2SO_4$), filtered, and concentrated in vacuo to yield 196 g of 6-carbobenzyloxyaminopentanoic acid as an oil which solidified upon standing: FAB-MS m/z 266 (MH$^+$).

A solution of 6-carbobenzyloxyaminopentanoic acid (50 g) in $CH_2Cl_2$ (500 mL) was treated with 2.2 mL of $H_2SO_4$ (conc.), saturated with isobutylene and stirred for 4 h. The resulting mixture was treated with 5% KOH (aq) (200 mL) and the layers were separated. The organic layer was washed twice with brine (2×100 mL), dried ($Na_2SO_4$) and concentrated. in vacuo. The residue was purified by flash column chromatography (silica gel, hexanes-ether) to afford 38 g of 6-carbobenzyloxyaminopentanoic acid t-butyl ester: MS m/z 322 (MH$_+$).

A mixture of 6-carbobenzyloxyaminohexanoic acid t-butyl ester (9 g, ?? mmol), Pd(OH)$_2$/C (4.5 g) and 50 mL of ethanol was shaken under 15 psig for 2h, filtered and concentrated in vacuo to give the amine 11a, as an oil: MS m/z 188 (MH$_+$). The material was used without further purification.

Step 11b

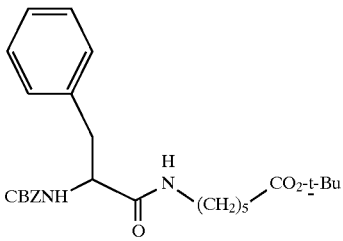   11b

A solution of HOBT (4.0 g, 30.2 mmol), DCC (4.6 g, 22.3 mmol) in DMF (35 mL) was added to a solution of amine 11a (4.2 g, 22.2 mmol) and CBZ-D-Phe (6.0 g, 20.0 mmol) in DMF (35 mL). This mixture was stirred overnight, filtered and concentrated in vacuo. The residue was dissolved in CHCl$_3$, washed sequentially with 10% NaHCO$_3$ (aq) and brine, dried (Na$_2$SO$_4$) and concentrated in vacuo. A 2.0 g portion of the crude residue was purified by flash column chromatography (silica gel, CHCl$_3$) to afford 1.8 g of the coupled ester 11b: MS m/z 469 (MH$_+$).

Step 11c

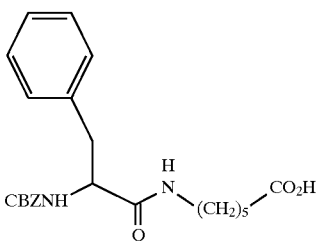   11c

A solution of 11 b (2.2 g, 4.7 mmol) in $CH_2Cl_2$ (5 mL) was added to a solution of 1:1 TFA—$CH_2Cl_2$ (25 mL) at 0° C. This solution was gradually warmed to RT and stirred for an additional 1.5h. The volatiles were removed under a stream of N$_2$, and the residue was triturated with ether to give the acid 11c as a white solid: (1.8 g); MS m/z 413 (MH$_+$).

Step 11d

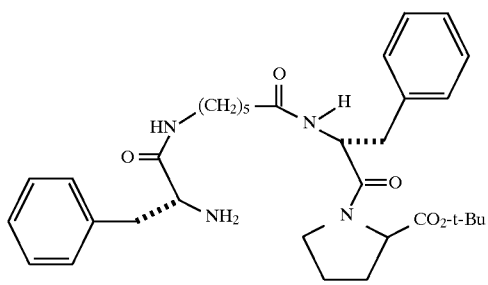

A solution of DCC (1.1 g, 5.5 mmol) in CH$_3$CN (5 mL) was added to a stirred solution of 11c (2.0 g, 5.0 mmol), D-Phe-Pro-O-t-Bu (1.8 g, 5.5 mmol) and HOBT (1.07 g, 7.5 mmol) in CH$_3$CN (35 mL). This mixture was stirred for 16 h, filtered and concentrated in vacuo. The residue was dissolved in CHCl$_3$, washed sequentially with 10% NaHCO$_3$ and brine, dried (Na$_2$SO$_4$) and concentrated in vacuo. This residue was purified by flash column chromatography (silica gel, CHCl$_3$→CHCl$_3$—MeOH) to give the coupled product as a foam: MS m/z 542 (M-Pro-O-t-Bu)$^+$. This material was combined with MeOH (50 mL) and Pd(OH)$_2$ (1.2 g) and shaken under H$_2$ (20 psig) for 2.5 h. The reaction was filtererd through dicalite and the filter pad thoroughly washed with MeOH. The filtrate was concentrated to give intermediate 11d as a foam: (1.8 g,); MS 579 (MH$^+$).

Step 11e

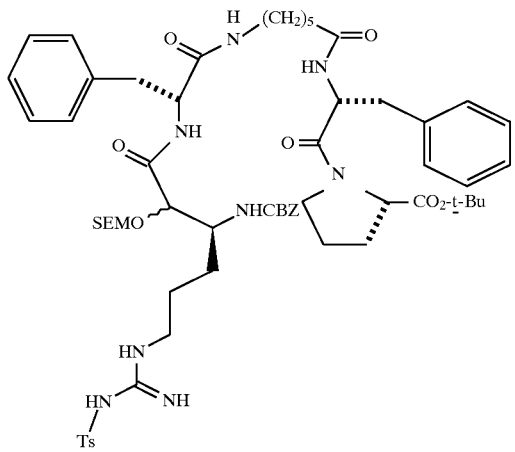

A solution of 6-[[imino[4-methylbenzenesulfonyl) amino]methyl]amino]-2-(R,S)-[[2-(trimethylsilyl)ethoxy] methoxy]-3(S)-[9-phenylrnethoxycarbonyl)-amino] hexanoic acid, (1.0 g, 1.6 mmol) of 11d (1.0 g, 1.8 mmol) and HOBT (0.3 g, 2.2 mmol) in CH$_3$CN (35 mL) was treated with a solution of DCC (0.4 g, 1.8 mmol) in CH$_3$CN (5 mL) and stirred overnight. The mixture was filtered and the filtrate was concentrated in vacuo. The residue was dissolved in CHCl$_3$, washed successively with 10% Na$_2$CO$_3$ and H$_2$O, dried (Na$_2$SO4) and concentrated in vacup. The residue was purified by flash chromatography (siica gel, CHCl$_3$→CHCl$_3$—MeOH) to give the arginine derivative 11e as a solid: (1.5 g); MS m/z 1184 (MH$^+$).

Step 11f

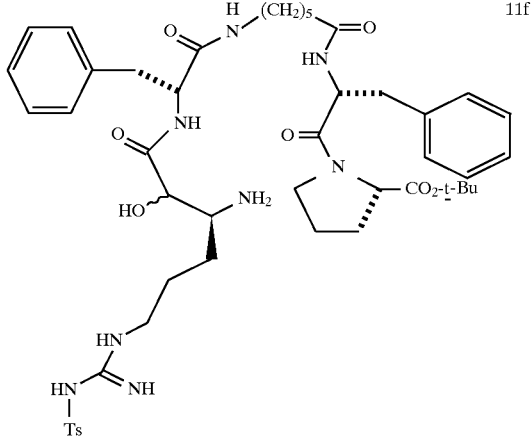

A mixture of 11e (1.5 g, 1.26 mmol), Pd(OH)$_2$, (0.8 g) and MeOH (50 mL)was shaken under of H$_2$ at 20 psig for 2.5 h. The mixture was filtered and the filtrate was concentrated in vacuo to give the deprotected intermediate 11f 1.2 g as an off white solid: MS m/z 1049 (MH$^+$).

Step 11g

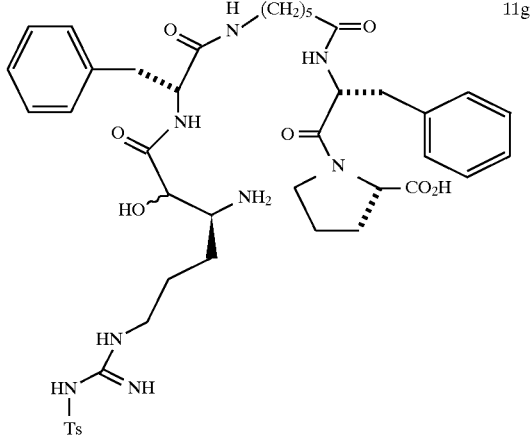

To a solution of 1:1 TFA—CH$_2$Cl$_2$ (15 mL) was added to a solution of 11h (1.24 g, 1.2 mmol) in CH$_2$Cl$_2$ (5 mL) at 0° C. This mixture was stirred for 2.5 h at room temperature, and the volatiles were removed under a stream of N$_2$. The residue was triturated with ether and collected to afford 11g, 1.1 g as a white solid: MS 863 (MH$^+$).

Step 11h

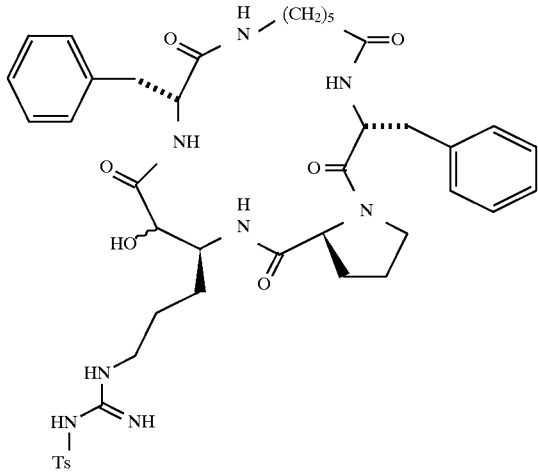

A mixture of 11g (1.1 g, 1.1 mmol) in CH$_2$Cl$_2$ (1.1 L) was treated with DMAP (0.7 g, 5.7 mmol) followed by BOP-Cl (0.6 g, 2.3 mmol). This mixture was stirred for 24 h, then concentrated in vacuo. The residue was dissolved in CH$_2$Cl$_2$, washed with 10% citric acid (aq), dried (Na$_2$SO4) and concentrated. in vacuo. The residue was purified by flash column chromatography (silica gel, CH$_2$Cl$_2$→95% CH$_2$Cl$_2$—MeOH to yield 11h, (0.3 g )as a solid: MS 845 (MH$^+$).

Step 11i

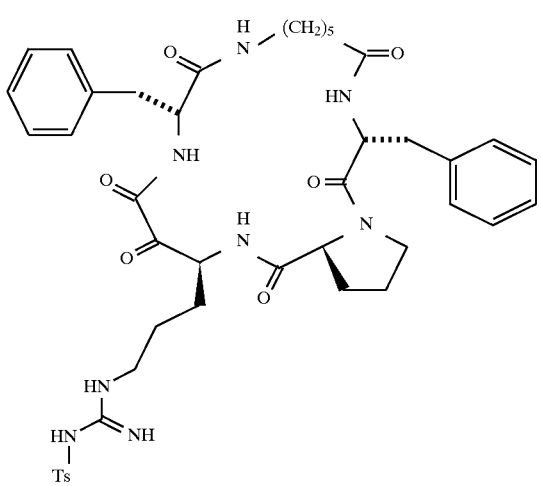

Intermediate 11h (0.3 g, 0.3 mmol) was added to a mixture of of Dess-Martin periodinane (2.0 g, 0.5 mmol) in CH$_2$Cl$_2$ (10 mL). The mixture was stirred for 1.5 h, and treated with an excess of 10% Na$_2$S$_{O3}$ (aq) in NaHCO$_3$ (satd. aq.). The layers were separated, and the aqueous layer was extracted three times with CHCl$_3$. The combined organic extracts were washed with H$_2$O, dried (Na$_2$SO$_4$), and concentrated in vacuo to give 11i (0.3 g) as a white solid which was used without purification.

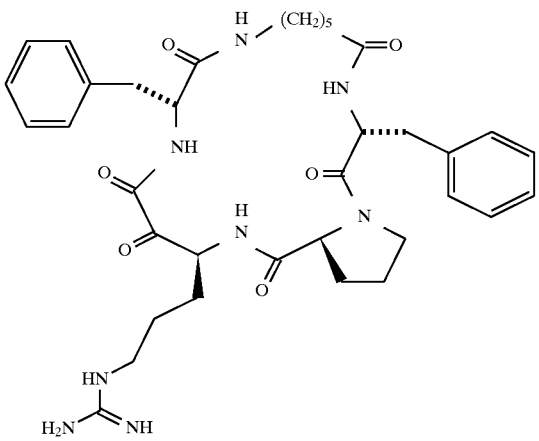

5R, 15R, 19S, 21AS-N-[3-(5, 15-DIBENZYL-4, 7, 14, 17,18, 21, HEXAOXOEICOSAHYDRO-3a, 6, 16, 20-PENTAAZACYCLOPENTACYCLOEI-COSEN-19-YL)PROPYL]GUANIDINE TRIFLUOROACETATE

COMPOUND 11

A mixture of intermediate 11i (0.3 g) and anisole (6 mL) was treated with HF (ca. 10 mL) at −78° C., and warmed to 0° C. This mixture was stirred for 4.5 h and the HF was removed in vacuo. The residue was triturated with ether and the resulting solid was purified by reverse phase HPLC (1:1 0.2 CH$_3$CN—H$_2$O—TFA) to afford the title compound (0.1 g ) as a white powder: MS 620 (MH$^+$); Anal. Calc'd for C$_{23}$H$_{45}$N$_7$O$_5$.1.75 C$_2$HF$_3$O$_2$.1.5 H$_2$O; Calc'd: C, 51.14; H, 5.63; N, 11.93; H$_2$O, 2.40; Found: C, 51.19; H, 5.70; N, 12.08; H$_2$O, 2.59.

EXAMPLE 12

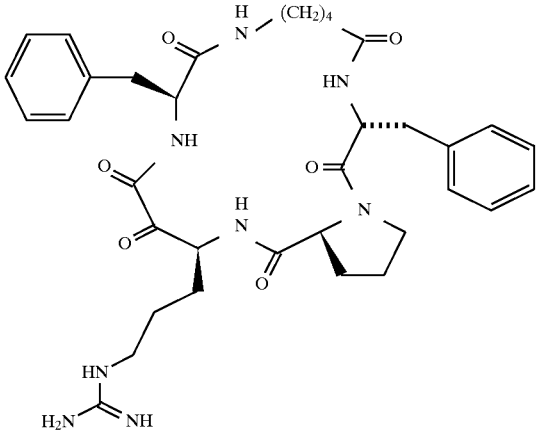

5R, 15S, 19S, 21a-S-N-[3-(5, 15-DIBENZYL-4, 7, 14, 17, 18, 21-HEXAOXODOCOSAHYDRO-3a, 6, 13, 16, 20-PENTAAZACYCLOPENTACYCLO-EICOSEN-19-YL)PROPYL)GUANIDINE TRIFLUOROACETATE

COMPOUND 12

Compound 12 was prepared following the method of Example 11. N-α-CBZ-L-Phe was used in place of N-α-

CBZ-D-Phe in Step 11b and all other steps were carried out with only minor modifications: Anal calc'd for $C_{36}H_{48}N_8O_6 \cdot 1.35 \, C_2HF_3O_2 \cdot 2.0 \, H_2O$; Calc'd: C, 52.89; H, 6.12; N, 12.75; $H_2O$, 4.10; Found: C, 53.02; H, 5.92; N, 12.82; $H_2O$, 3.97

EXAMPLE 13

5R, 18S, 20a-S-N-[3-(5-BENZYL-4, 16, 17, 20-TETRAOXOEICOSAHYDRO-3a, 6, 15, 19-TETRAAZACYCLOPENTACYCLONONADECEN-18-YL) PROPYL]GUANIDINE TRIFLUOROACETATE

Step 13a

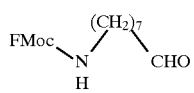

Fluorenylmethoxycarbonyl chloride (4.87 g, 0.02 mol) to a mixture of aminooctanoic acid (3.0 g ,0.02 mol) in 200 mL of 10% $Na_2CO_3$ (aq) and dioxane (150 mL) at 0° C. The mixture was stirred for 2.5 h at 0° C., acidified to pH 5 with acetic acid and extracted three times with $CHCl_3$. The combined organic extracts were washed with $H_2O$, dried ($Na_2SO_4$) and concentrated in vacuo. The residue was purified by flash chromatography (silica gel, $CHCl_3 \rightarrow 95:5$ $CHCl_3$—MeOH) to afford 8-fluorenylmethoxycarbonylaminooctanoic acid (6.4 g) as a solid: MS 382 (MH+). The product was dissolved in $CH_2Cl_2$ (40 mL), cooled to 0° C., and treated with methoxymethyl amine hydrochloride (2.05 g, 21.1 mmol), triethylamine (8.1 mL) and BOP reagent (8.0 g). This mixture was stirred for 12 h at 0° C., washed sequentially with 3N HCl, $NaHCO_3$ (sat"d. aq.) and brine. The organic phase was dried ($Na_2SO_4$) and concentrated. in vacuo. The residue was purified by flash column chromatography (silica gel; $CHCl_3 \rightarrow 98:2$ $CHCl_3$—MeOH) to afford 8-fluorenylmethoxycarbonyl-aminooctanoic acid N,N-methoxymethyl amide (7.1 g): MS m/z 425 (MH$_+$). A solution of the product (6.8 g) in THF (80 mL) was cooled to −40° C. and treated dropwise with 1.0M DIBAL/THF (48.5 mL). The mixture was stirred an additional 15 min, quenched with 3N HCl (50 mL) and warmed to room temperature. The resulting aqueous layer was extracted repeatedly with $CHCl_3$ and the combined organic extracts were washed with brine, dried ($Na_2SO_4$) and concentrated in vacuo. The residue was purified by chromatography (silica gel; $CH_2Cl_2 \rightarrow 2\%$ MeOH—CH2Cl2) to afford aldehyde 13a as a solid: 5.2 g; MS m/z 366 (MH+).

Step 13b

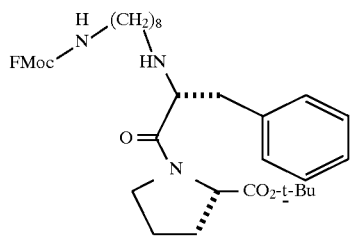

A solution of 13a (4.2 g, 11.6 mmol) and D-Phe-Pro-O-t-Bu (4.1 g, 12.7 mmol) in $CH_2Cl_2$ (100 mL) was treated with sodium triacetoxy borohydride (3.7 g, 17.4 mmol), followed by glacial acetic acid (0.7 g). This mixture was stirred for 3.5 h, treated with excess $NaHCO_3$ (sat'd) and the resulting aqueous layer was extracted repeatedly with $CH_2Cl_2$. The combined organic layers were washed with brine, dried ($Na_2SO_4$), and concentrated in vacuo to give the coupled product 13b as a semi-solid: 7.8 g; MS m/z 668 (MH+).

Step 13c

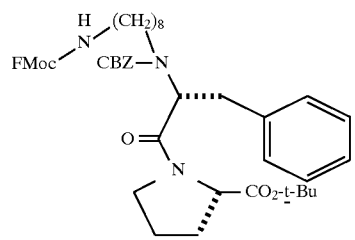

A mixture of 13b (7.8 g, in 1:1 $CH_2Cl_2$—$H_2O$ (30 mL) was cooled to 0° C. and treated with $NaHCO_3$ (1.1 g, 12.7 mmol) of followed by dropwise addition of benzylchloroformate (1.8 mL, 12.7 mmol). This mixture was stirred for 2 h at 0° C., and the aqueous phase was extracted repeatedly with $CH_2Cl_2$. The combined organic layers were washed sequentially with $H_2O$ and brine, dried ($Na_2SO_4$) and concentrated in vacuo. The residue was purfied by flash chromatography (silica gel, $CHCl_3$) to give 13c as a semi-solid: 7.3 9; MS m/z 802 (MH+).

Step 13d

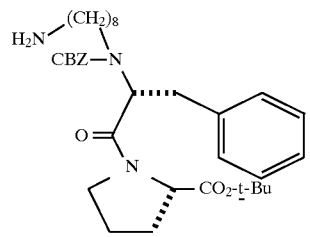

A solution of 13c (2.4 g) in DMF (20 mL) was treated with piperidine 4 mL and stirred for 25 min. The resulting mixture was concentrated in vacuo and triturated with hexane to give 13d as an oil: 1.5 g; MS m/z 580 (MH+).

Step 13e

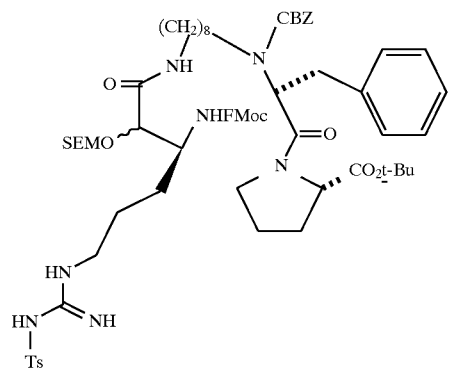

A solution of 6-[[imino[4-methylbenzenesulfonyl) amiino]methyl]amino]-2-(R,S)-[[2-(trimethylsilyl)ethoxy]

methoxy]-3(S)-[9-fluorenylmethoxycarbonyl)-amino]
hexanoic acid (1.6 g, 2.3 mmol), 13d (1.4 g, 2.5 mmol), and
HOBT (0.46 g, 3.4 mmol) in CH₃CN (35 mL) was treated
with a solution of DCC (0.51 g, 2.5 mmol) in CH₃CN (5
mL). This mixture was stirred for 12 h, filtered, and the
filtrate was concentrated in vacuo. The residue was purified
by flash column chromatography (silica gel, CHCl₃→5%
MeOH—CHCl₃) to afford 13e as a semi solid: 1.8 g; MS m/z
1273 (MH+)

Step 13f

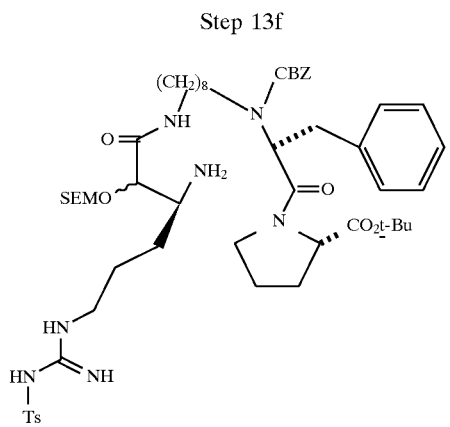

13f

Piperidine (4 mL) was added to a solution of 13e (1.7 g)
in DMF (20 mL) and stirred for 30 min. This mixture was
concentrated in vacuo and the residue was washed with
hexanes to yield 13f as an oil: 1.4 g; MS m/z 1050 (MH+)

Step 13g

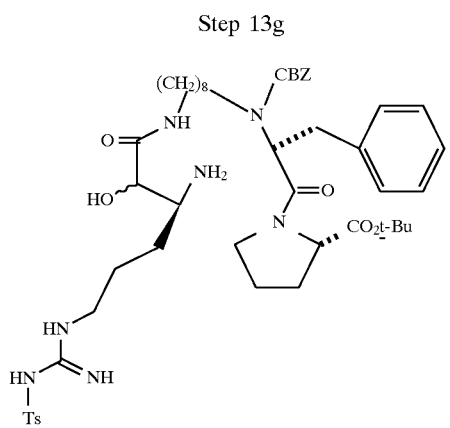

13g

A solution of TFA (15 mL) and CH₂Cl₂ (10 mL) was
added a solution of 13f (1.4 g) in CH₂Cl₂ (5 mL) at 020 C.
This mixture was warmed to room temperature and stirred
for 2 h. The volatiles were removed under a stream of N₂.
and the residue was triturated with ether to afford 13g as a
solid: 1.1 g; MS m/z 864 (MH+).

Step 13h

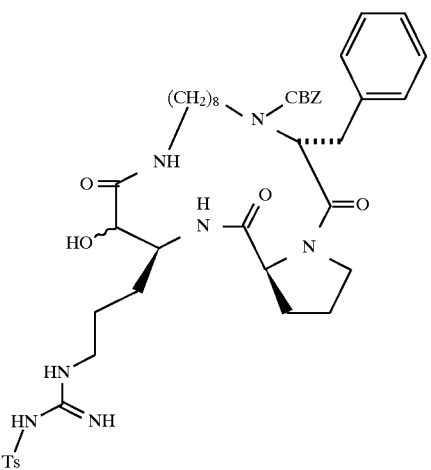

13h

BOP-CI (0.5 g, 2.0 mmol) was added to a solution of 13g
(1.1 g, 1.0 mmol) and DMAP (0.63 g, 5.2 mmol) in CH₂Cl₂
(1.0 L). This mixture was stirred for 6 h and concentrated in
vacuo. The residue was purified by flash column chromatography (silca gel; 5% MeOH—CH₂Cl₂) to afford 13 h as
a white foam: 0.31 g; MS m/z 846 (MH+).

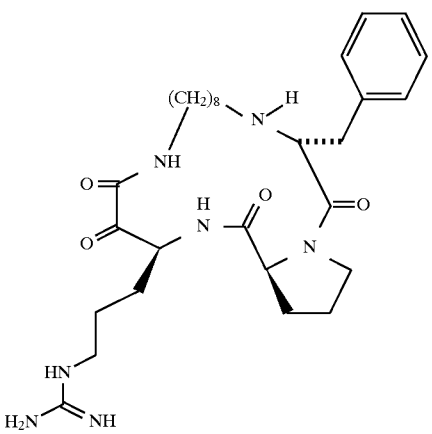

5R, 18S, 20a-S-N-[3-(5-BENZYL-4, 16, 17, 20-
TETRAOXOEICOSAHYDRO-3a, 6, 15, 19-
TETRAAZACYCLOPENTACYCLONONADECEN-
18-YL) PROPYL]GUANIDINE
TRIFLUOROACETATE

COMPOUND 13

A suspension of 13e (0.2 g, 0.4 mmol) in CH₂Cl₂ (10 mL)
was treated with (0.3 g, 0.6 mmol) of the Dess-Martin
periodinane and stirred for 2 h. The mixture was treated with
excess solution of 25% NaS₂O₃ in NaHCO₃ (sat'd aq.) and
the the aqueous layer was extracted repeatedly with CH₂Cl₂.
The combined organic extracts were washed with water,
dried (Na₂SO₄) and concentrated in vacuo to yield the
keto-amide product (0.3 g)which was used in the next step
without purification: MS m/z 844 (MH+). A stirred mixture
of the keto-amide and anisole (3 mL) was treated with HF
(ca. 15 mL) at −78° C. This mixture was stirred an additional
3.5 h at 0° C., and the HF was removed in vacuo at 0° C. The residue was triturated with ether, and the residue was purified by reverse-phase HPLC (30:70:0.2 CH$_3$CN—H$_2$O—TFA). The desired fractions were lyophilized to give the title compound as a white solid:0.1 g; MS m/z 556.5 (MH+); Anal. Calcd for C$_{29}$H$_{45}$N$_7$O$_4$.2.75 C$_2$HF$_3$O$_2$.1.25 H$_2$O; Calc'd: C, 46.46; H, 5.68; N, 10.99; H$_2$O, 2.47; Found: C, 46.53; H, 5.72; N, 11.15; H$_2$O, 2.77.

EXAMPLE 14

2S, 5S, 9R-N[3-(9-BENZYL-3, 6, 7, 10, 19-(PENTAOXOEICOSAHYDRO)-1a, 4, 8, 11-(TETRAAZACYCLOPENTACYCLONONADECEN-5-YL)PROPYL] GUANIDINE TRIFLUOROACETIC ACID.

Step 14a

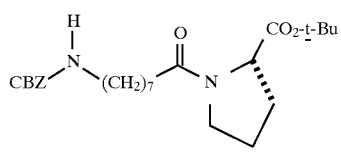

A solution of N-αCbz-aminooctanoic acid (2.5 g, 8.5 mmol), Pro-O-t-Bu (1.6 g, 9.4 mmol) and HOBT (1.7 g, 12.8 mmol) in CH$_3$CN (80 mL) was added a solution of DCC (1.4 g, 9.4 mmol) in CH$_3$CN. (15 mL). The reaction was stirred overnight, filtered and the resulting filtrate concentrated in vacuo. The residue was purified by flash column chromatography CH$_2$Cl$_2$→2% MeOH—CH$_2$O$_2$) to afford 14a:3.8 g; MS m/z 447 (MH+).

Step 14b

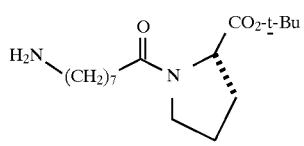

A mixture of 14a (3.6 g), Pd(OH)$_2$ (1.8 g) in MeOH (5 mL) was shaken under H$_2$ (20 psig) for 2.5 h. This mixture was filtered, and the filtrate was concentrated in vacuo to give the free amine 14b (2.5 g) which was used without further purification.

Step 14c

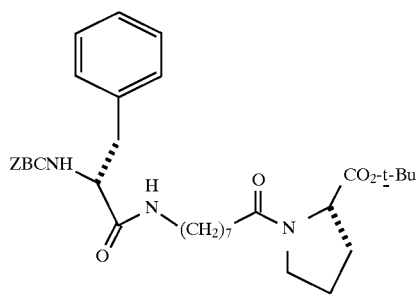

A solution of N-α-Cbz-D-Phe (2.2 g, 7.3 mmol) of, 14c (2.5 g, 8.1 mmol) and HOBT (1.4 g, 11.0 mmol) in CH$_3$CN (10 mL) was treated with DCC (1.7 g, 8.1 mmol) in CH$_3$CN (10 mL). The mixture was stirred overnight, filtered and the filtrate was concentrated in vacuo. The residue was dissolved in CHCl$_3$, washed with NaHCO$_3$ (sat'd. aq), dried (Na$_2$SO$_4$) and concentrated in vacuo. This residue was purified by flash column chromatography (silica gel, 97:3 CHCl$_3$—MeOH) to afford 14c: 3.7 g; MS m/z 594 (MH+).

Step 14d

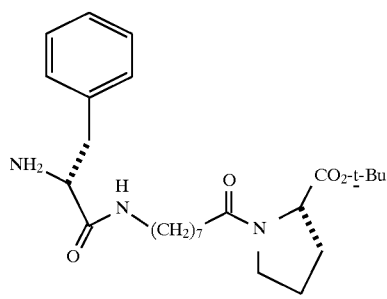

A mixture of 14c (3.7 g), MeOH (75 mL) and PdOH$_2$ (1.4 g)was shaken under H$_2$ (20 psig) for 2.5 h and filtered. The filtrate was concentrated in vacuo to afford 14d (2.5 g) which was used in the next step without purification.

Step 14e

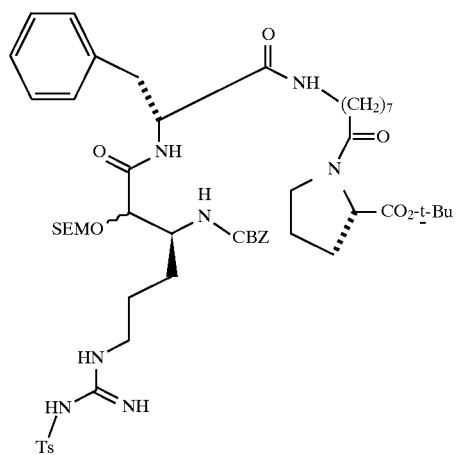

A mixture of 6-[[imino[4-methylbenzenesulfonyl) amino] methyl]amino]-2-(R,S)-[[2-(trimethylsilyl)ethoxy] methoxy]-3(S)-[9-phenylmethoxycarbonyl)-amino] hexanoic acid (1.0 g, 1.6 mmol), 14d (0.81 g, 1.8 mmol) and HOBT (0.32 g, 2.4 mmol) of HOBT in CH$_3$CN (60 mL) was treated with DCC (0.36 g, 1.8 mmol) in CH$_3$CN (60 mL). This mixture was stirred overnight, filtered and the resulting filtrate was concentrated in vacuo. The residue was dissolved in CHCl$_3$, washed with 10% aqueous Na$_2$CO$_3$, dried (Na$_2$SO$_4$) and concentrated in vacuo. This residue was purified by flash column chromatography (silica gel, CHCl$_3$→98% CHCl$_3$—MeOH) to afford 14e (1.42 g) as a white solid: MS m/z 1064 (MH+).

Step 14f

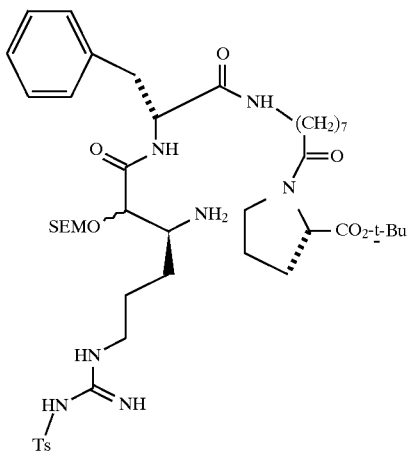

A mixture of 14e (1.42 g) Pd(OH)$_2$ (0.8 g) and MeOH (50 mL) under H$_2$ (20 psig) for 2.5 h. This mixture was filtered, and the filtrate concentrated in vacuo to yield amine 14f (1.18 g): MS m/z 930 (MH+).

Step 14g

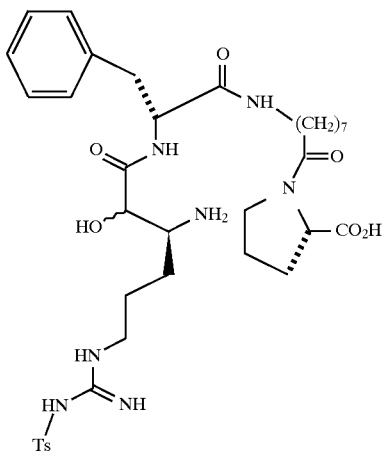

A solution of 14g (1.18 g) in CH$_2$Cl$_2$ (5 mL) was added to a solution of 1:1 TFA—CH$_2$Cl$_2$ (20 mL) at 0° C. This mixture was stirred for 2 h at room temperature and the solvent was removed under a stream, of N$_2$. The residue was triturated with ether to afford 14g (1.02 g) which wasd used without additional purification.

Step 14h

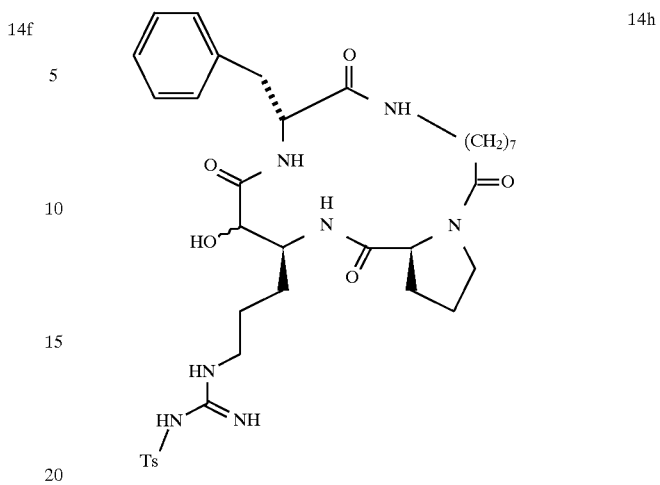

A solution of 14 h (1.01 g, 1.18 mmol) in CH$_2$Cl$_2$ was treated with DMAP (0.73 g, 6.0 mmol) of DMAP followed by BOP-Cl (0.60 g, 2.35 mmol). This mixture was stirred for 24 h and the total volume was reduced to 100 mL in vacuo. This solution was washed with 10% aqueous citric acid, dried (Na$_2$SO$_4$) and concentrated in vacuo. The residue was purified by flash column chromatography (silica gel, CH$_2$Cl$_2$→10% MeOH—CH$_2$Cl$_2$) to yield 14 h (0.30 g)

Step 14i

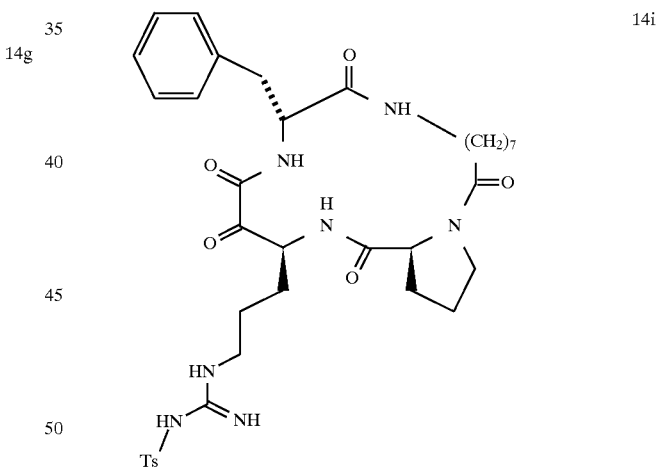

A solution of 14i (0.30 g, 0.42 mmol) in CH$_2$Cl$_2$ (10 mL) was added to a suspension of Dess-Martin periodinane (0.26 g, 0.62 mmol) in CH$_2$Cl$_2$ (10 mL) After 2.5 h, the mixture was treated with an excess of 25% Na$_2$S$_2$O$_4$ (aq) in NaHCO$_3$ (sat'd. aq) and stirred for 5 min. The aqueous layer was extracted with CH$_2$Cl$_2$ and the combined organic extracts were washed with H$_2$O, dried (Na$_2$SO$_4$) and concentrated under in vacuo to afford 14i (0.30 g) which was used in the next step without purification: MS m/z 724 (MH+).

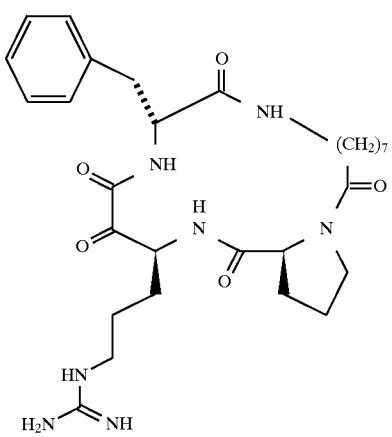

2S, 5S, 9R-N[3-(9-BENZYL-3, 6, 7, 10, 19-(PENTAOXOEICOSAHYDRO)-1a, 4, 8, 11-(TETRAAZACYCLOPENTACYCLONONADECEN-5-YL)PROPYL]GUANIDINE TRIFLUOROACETIC ACID

COMPOUND 14

A suspension of 14i (0.30 g) in anisole (2 mL) was cooled to −78° C. and treated with anhydrous HF (ca. 10 mL) using a standard HF apparatus. This mixture was stirred for 4 h at 0° C. and the HF was removed in vacuo at 0° C. This residue was triturated twice with ether (2×25 mL) and the resulting solid was purified by reverse-phase HPLC (MeCN-water-TFA, 40:60:0.2). Lyophillization of the eluate provided the title compound (0.44 g) as a white solid: FAB-MS m/z 570 (MH+); Anal. Calc'd for $C_{29}H_{43}N_7O_5 \cdot 1.25\ C_2HF_3O_2 \cdot 2.0\ H_2O$; Calc'd: C, 50.56; H, 6.50; N, 13.10; $H_2O$, 4.82; Found: C, 50.31, H, 6.25; N, 12.70; $H_2O$; 4.33.

EXAMPLE 15

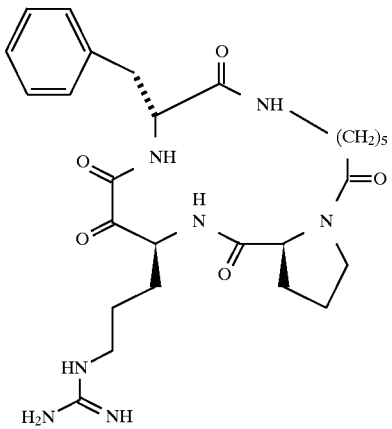

12R, 16S, 19S-N-[3-(12-BENZYL-4, 11, 14, 15, 18-PENTAOXOOCTADECAHYDRO)-3a, 10, 13, 17-(TETRAAZACYCLOPENTACYCLOHEPTADECEN-16-YL)PROPYL]-GUANIDINE TRIFLUOROACETIC ACID

COMPOUND 15

The preparation of compound 15 is analogous to Example 14. The hexanoyl analog of 14d, namely 1(S)-[6-(2(R)-amino-3-phenylpropionylamino)hexanoyl]pyrrolidine-2-carboxylic acid t-butyl ester, was prepared by coupling CBZ-D-Phe with 6-aminohexanoic acid -t-butyl ester, saponifying the ester and coupling the resulting acid with Pro-O-t-Bu. The remaining steps of Example 14 were carried out to give the title compound as a solid: FAB-MS m/z 542 (MH+); Anal Calc'd. for $C_{27}H_{39}N_7O_5 \cdot 1.75\ CF_3CO_2H \cdot 1.5\ H_2O$; Calc'd: C, 47.69; H, 5.74; N, 12.76; $H_2O$, 3.53; Found: C, 47.81; H, 5.74; N, 13.04; $H_2O$, 3.57.

EXAMPLE 16

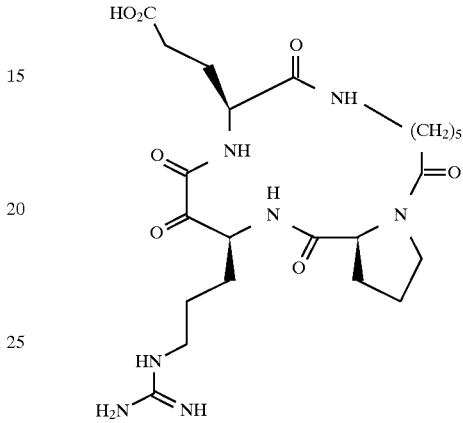

12S, 16S, 19S-3-[16-(3-GUANIDINOPROPYL)-4, 11, 14, 15, 18-PENTAOXOOCTADECAHYDRO-3, 10, 13, 17-TETRAAZACYCLOPENTACYCLO HEPTADECEN-1,2-YL]PROPIONIC ACID TRIFLUOROACETATE

COMPOUND 16

The preparation of compound 16 is analogous to Example 14. The hexanoyl analog of 14d, namely 1(S)-[6-(2(R)-amino-3-(carboxymethyl)propionylamino)hexanoyl] pyrrolidine-2-carboxylic acid t-butyl ester, was prepared by coupling L-N-α-Fmoc-Glu(OBzl)-OH with 6-aminohexanoic acid -t-butyl ester, saponifying the ester and coupling the resulting acid with Pro-O-t-Bu. The remaining steps of Example 14 were carried out to give the title compound as a solid: FAB-MS m/z 523 (MH+); Anal Calc'd. for $C_{23}H_{37}N_7O_7 \cdot 2.0CF_3CO_2H \cdot 1.5\ H_2O$; Calc'd: C, 41.65; H, 5.44; N, 12.59; $H_2O$, 3.47; Found: C, 41.83; H, 5.30; N, 12.64; $H_2O$, 3.57.

EXAMPLE 17

5R, 18S,21S-N-[3-(4,7,16,17,20-PENTAOXO-5-PHENETHYLEICOSAHYDRO-3a, 6, 15, 19-TETRAACBZACYCLOPENTACYCLONONADECEN-18-YL)PROPYL]GUANINDINE TRIFLUOROACETIC ACID

Step 17a

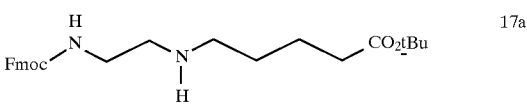

Sodium Trriacetoxyborohydride (6.1 g, 29 mmol) and acetic acid (1 mL) were added to a solution of N-α-

(fluorenylmethyloxycarbonyl)glycinal (5.4 g, 19 mmol: prepared by the method of Ho, et al. *Journal Of Organic Chemistry* 1983, 58, 2313–16) and 5-aminopentanoic acid t-butyl ester (3.6 g, 20 mmol) in $CH_2Cl_2$ (30 mL). This mixture was stirred overnight and concentrated in vacuo to give 17a which was used without purification Step 17b

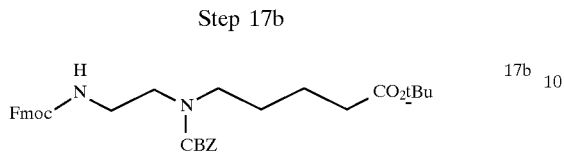

17b

To a solution of 11 g of intermediate 3 and 5.6 mL of triethylamine in 150 mL of $CH_2Cl_2$ at 0° C. Carbobenzoxychloride (3.1 mL) was added to a stirred solution of 14a (11 g) and triethylamine (5.6 mL) in $CH_2Cl_2$ (150 mL). After 2 h, the reaction was quenched with $H_2O$, and the resulting organic layer was extracted twice with $CH_2Cl_2$. The combined organic layers were dried ($Na_2SO_4$) and concentrated. The residue was purified by flash chromatography (silica gel; 3:1 hexanes-ether→3:2 hexanes-ether) to afford 2.6 g of 17b as a white solid: MS m/z 573 (MH+).

Step 17c

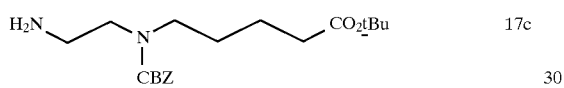

17c

A solution of intermediate 17b (2.42 g) in $CH_2Cl_2$ (5 mL) was added to a 1:1 solution of TFA—$CH_2Cl_2$ (20 mL) at 0° C. The reaction was stirred for 1 h at room temperature, then volatiles were removed under a, stream of $N_2$ at room temperature. The residue was purified by chromatography (flash column, silica gel; 9:1 $CHCl_3$—MeOH) to afford 1.8 g of 17c: MS m/z 517 (MH+).

Step 17d

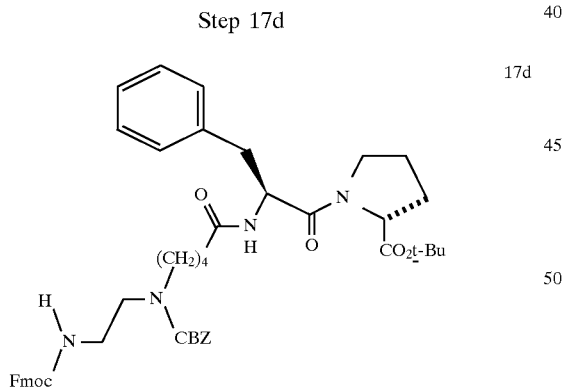

17d

A solution of 17c (1.72 g, 3.33 mmol) and D-Phe-Pro-O-t-Bu (1.58 g, 4.99 mmol) and HOBT (0.67 g, 4.99 mmol) was treated with a solution of DCC (1.03 g, 5.00 mmol) in $CH_3CN$ (3 mL) and stirred overnight. The mixture was filtered and concentrated, and the residue was purified by flash chromatography (silica gel, 100% $CHCl_3$→98% $CHCl_3$—MeOH) to give 2.28 g of intermediate 17d: MS m/z 817 (MH+).

Step 17e

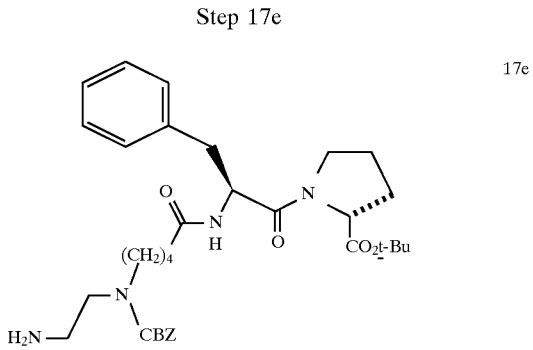

17e

A solution of 17d (2.24 g) in $CH_3CN$ (25 mL) was treated with diethylamine (6 mL) and the mixture was stirred for 2.5 h. The solution was concentrated in vacuo, and the residue was purified by flash chromatography (silica gel, 100% $CHCl_3$→90% $CHCl_3$—MeOH) to give 1.27 g of intermediate 17e: MS m/z 595 (MH+).

Step 17f

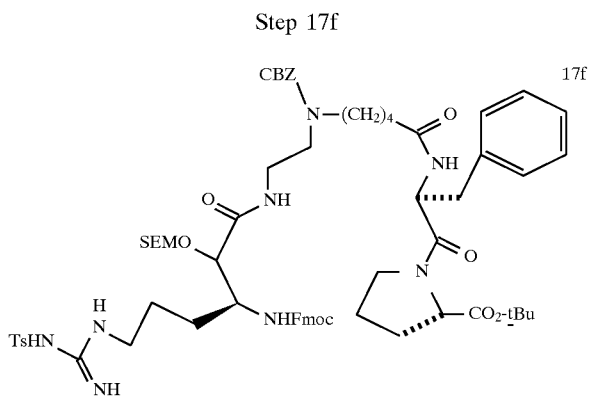

17f

To a stirred solution of [[imino[4-methylbenzenesulfonyl)amino]methyl]amino]-2-(R,S)-[[2-(trimethylsilyl)ethoxy]methoxy]-3(S)-[9-fluorerylmethoxycarbonyl)-amino]hexanoic acid, (2.5 g ,4.0 mmol: prepared analogous to the CBZ derivative in Maryanoff et al. *Journal of the American Chemical Society* 1995, 117, 1225–39) and intermediate 17f (1.27 g, 2.13 mmol) and HOBT (0.39 g, 2.91 mmol) in $CH_3CN$ (45 mL) was added DCC (0.44 g, 2.13 mmol) and this mixture was stirred overnight. The reaction was filtered, the filtrate was concentrated, and the residue was purified by flash chromatography (silica gel, 100% $CHCl_3$→95% $CHCl_3$—MeOH) to yield 1.96 g of intermediate 17f: MS m/z 1287 (MH+).

Step 17g

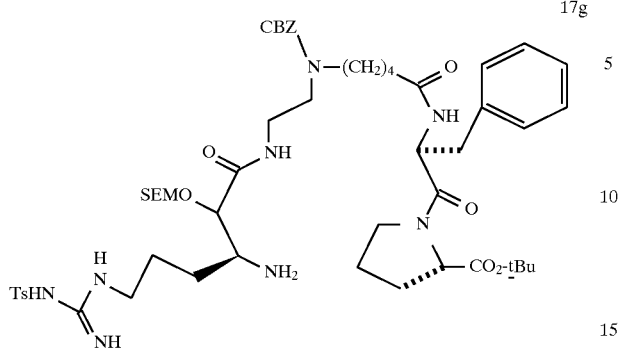

A solution of intermediate 17g (1.93 g) in CH₃CN (20 mL) was treated with diethylamine (5 mL) and stirred for 2 h. The solution was concentrated, and the residue was triturated repeatedly with ether to afford 1.31 g of intermediate 17g: MS m/z 1065 (MH+).

Step 17h

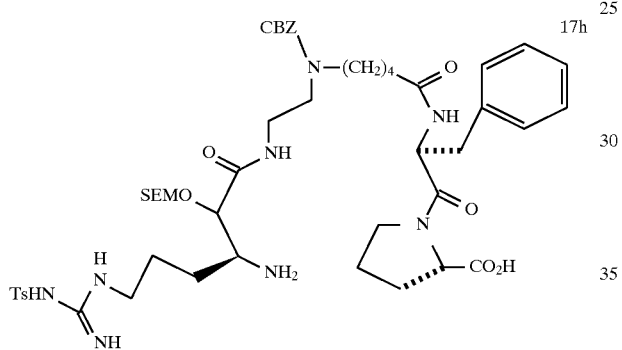

To a solution of 1:1 TFA—CH₂Cl₂ (20 mL) at 0° C. was added a solution of intermediate 17g (1.31 g, 1.23 mmol) in CH₂Cl₂ (5 mL) After stirring at room temperature for 1 h, the solution was concentrated under a stream of N2, and the residue was triturated with ether to afford 1.1 g of intermediate 17 h as a white solid: MS m/z 879 (MH+).

Step 17i

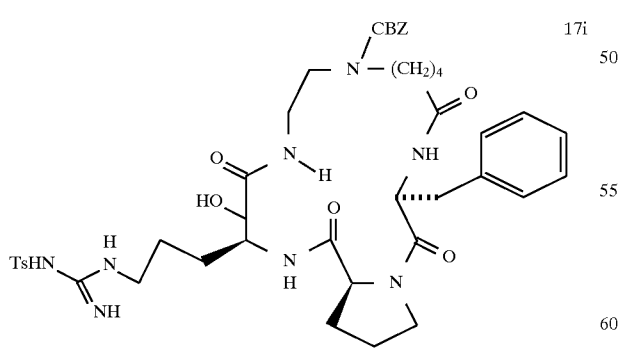

A mixture of intermediate 17 h (1.1 g, 1.0 mmol) and DMAP (0.63 g, 5.1 mmol) in CH₂Cl₂ (1 L) was treated with BOP-Cl (0.51 g, 2.0 mmol) and stirred for 4 h. The mixture was reduced ca. 75%, washed twice with 10% aqueous citric acid, dried (Na2SO4) and concentrated. The residue was purified by flash column chromatography (silica gel, CH2Cl2→10% MeOH—CH2Cl2) to give 0.53 g of intermediate 17i: MS m/z 861 (MH+).

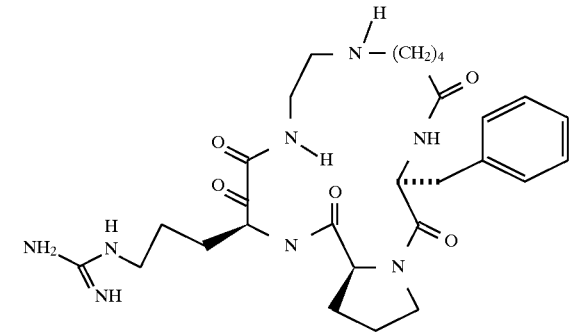

5R, 18S,21S-N-[3-(4,7,16,17,20-PENTAOXO-5-PHENE THYLEICOSAHYDRO-3a, 6, 15, 19-TETRAAZACYCLOPENTACYCLONONADECEN-18-YL)PROPYL]GUANINDINE TRIFLUOROACETIC ACID

COMPOUND 17

To a mixture of Dess-Martin periodinane (0.39 g, 0.89 mmol) in CH₂Cl₂ (10 mL) was added to a solution of intermediate1 17i (0.51 g) in CH₂Cl₂ (10 mL). After stirring for 1 h, the reaction was treated with excess 25% Na₂S₂O₃ (aq) in NaHCO₃ (sat'd., aq.) and the layers were separated. The aqueous layer was extracted three times with CHCl₃, and the combined organic layers were washed with water, dried (Na₂SO₄), and concentrated in vacuo to afford 0.46 g of the corresponding keto-amide: MS m/z 859 (MH+). A mixture of the keto-amide (0.44 g) in anisole (3 mL) was treated with ca. 10 mL of HF at −78° C. and stirred at 0° C. for 3.5 h. Excess HF was removed under in vacuo at 0° C., and the residue was triturated twice with ether. The residue was purified by reverse-phase HPLC (80:20:0.2 H₂O—CH₃CN—TFA) to afford 0.052 g of the title compound as a white solid: MS m/z 571.5 (MH+); mp 102°–106° C.; Anal. Calcd. for C₂₈H₄₂N₈O₅·2.5 C₂HF₃O₂·3.5 H₂O; Calculated C, 43.14; H, 5.65; N, 12.20; H₂O, 6.86; Found: C, 42.91; H, 5.38; N, 12.42; H₂O, 6.44.

EXAMPLE 18

N-[3-(3-BENZYL-2,5,6,9-TETRAOXO-1,4,8-TRIAZACYCLOTETRADEC-7-YL)PROPYL]GUANIDINE TRIFLUOROACETIC ACID

Step 18a

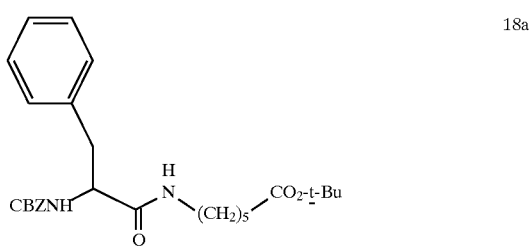

Intermediate 18a was prepared following steps 11a and 11b of example by using 6-aminohexanoic acid instead of aminopentanoic acid in step 11a.

Step 18b

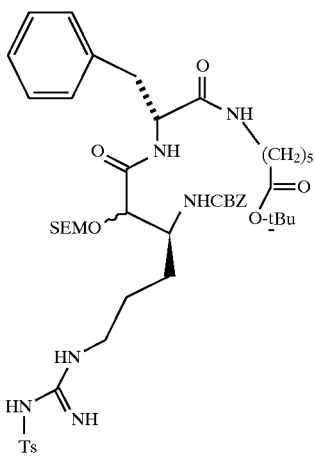

18b

A mixture of 18a (0.72 g, 2.15 mmol), 6-[[imino[4-methylbenzenesulfonyl) amino]methyl]amino]-2-(R,S)-[[2-(trimethylsilyl)ethoxy]methoxy]-3(S)-[9-phenylmethoxycarbonyl)-amino]hexanoic acid (1.47 g, 2.36 mmol) and HOBT (0.44 g, 3.22 mmol) dissolved in CH₃CN (30 mL) was treated with a solution of DCC (0.49 g, 2.36 mmol) in CH₃CN (30 mL) and stirred overnight. The mixture was filtered, concentrated in vacuo and the residue was dissolved in mL ethyl acetate (50 mL) and washed with saturated aqueous NaHCO₃ (5 mL). The organic extract was dried (Na₂SO₄) and concentrated. The residue was purified via flash column chromatography (9:1 CH₂Cl₂-MeOH) to yield 1.72 g of intermediate 18b.

Step 18c

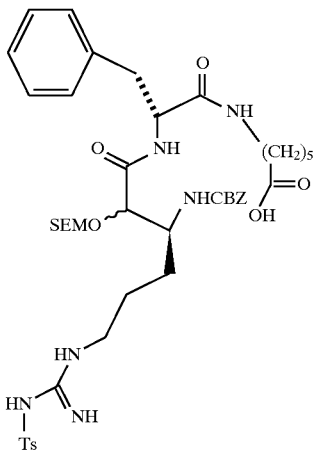

18c

A solution of intermediate 18b (1.71 g, 1.82 mmol) in CH₂Cl₂ (5 mL) was added to 1:1 TFA—CH₂Cl₂ (28 mL) solution at 0° C. The mixture was stirred for 1 h at room temperature and concentrated under a stream of N₂. The residue was triturated with ether to afford 1.6 g of intermediate 18c as a white solid.

Step 18d

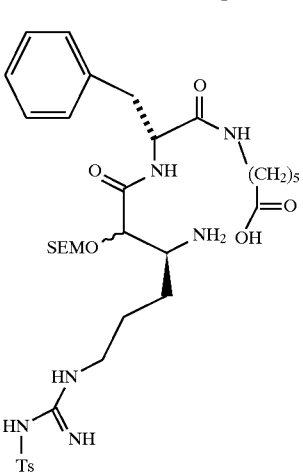

18d

A mixture of intermediate 18c (500 mg, 0.5 mmol), Pd(OH)₂ (600 mg) and methanol (30 mL) was shaken under H₂ at 21 psig for 5 h. The mixture was filtered, and the filtrate was concentrated to afford 390 mg of intermediate 18d as a white solid: m/z 619 (MH+).

Step 18e

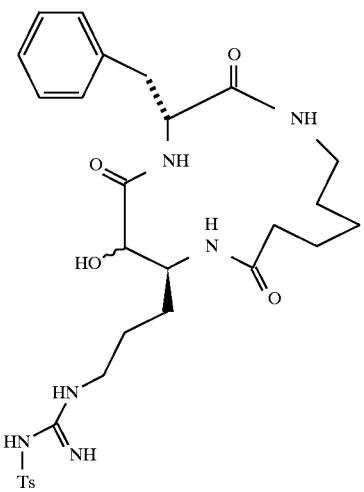

18e

A solution of intermediate 5 (340 mg, 0.464 mmol) and DMAP (283 mg, 2.32 mmol) in 450 mL of CH₂Cl₂ was treated with BOP-Cl (236 mg, 0.928 mmol) and stirred for 5 h. Solvent was removed under reduced pressure, and the residue was purified via flash column chromatography (silica gel, 95:5 CH₂Cl₂—MeOH→90:10 CH₂Cl₂—MeOH) to yield 78 mg of intermediate 18e: m/z 601 (MH+).

Step 18f

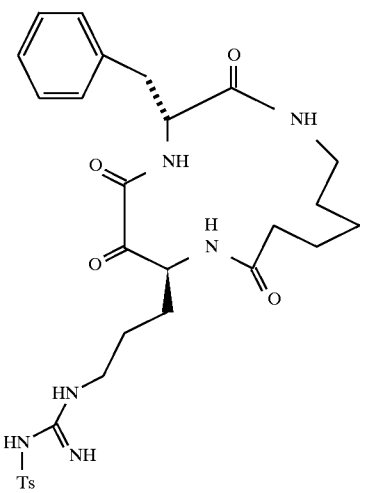

A solution of intermediate 18e (78 mg, 0.13 mmol) in CH$_2$Cl$_2$ (15 mL) was treated with (82 mg, 0.19 mmol) of the Dess-Martin periodinane. The mixture was stirred for 3.5 h, treated with of aqueous 4:1 NaHCO$_3$—Na$_2$S$_2$O$_3$ (20 mL). This mixture was extracted four times with 25 mL portions of CH$_2$Cl$_2$. The combined CH$_2$Cl$_2$ extracts were washed with brine, dried (Na$_2$SO$_4$), and concentrated to provide 49 mg of intermediate 18f which was used in the following step without further purification: m/z 599 (MH+).

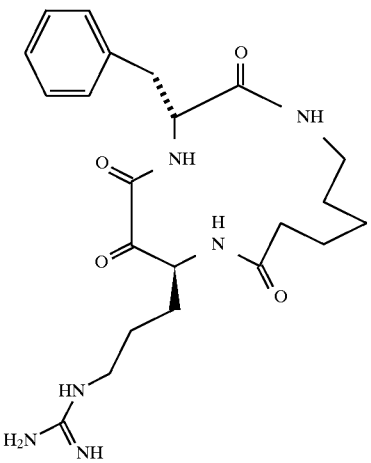

N-[3-(3-BENZYL-2,5,6,9-TETRAOXO-1,4,8-TRIAZACYCLOTETRADEC-7-YL)PROPYL] GUANIDINE TRIFLUOROACETIC ACID

COMPOUND 18

A suspension of intermediate 18f (49 mg) in anisole (1 mL) was treated with ca. 5 mL of anhydrous HF at −78° C. The mixture was stirred at 0° C. for 3.5 h and the excess HF was removed under vacuum. The residue was triturated with ether and purified by reverse-phase HPLC (MeCN-water-TFA, 30:70:0.2) to give 10.4 mg of the title compound as a white solid: m/z 445 (MH+); Anal. Calcd for C$_{22}$H$_{32}$N$_6$O$_4$·1.75C$_2$HF$_3$O$_2$·1.18H$_2$O; Calculated: C, 46.03; H, 5.47; N, 12.63; H$_2$O, 3.19; Found: C, 46.03; H, 4.95; N, 12.99; H$_2$O, 3.49.

EXAMPLE 19

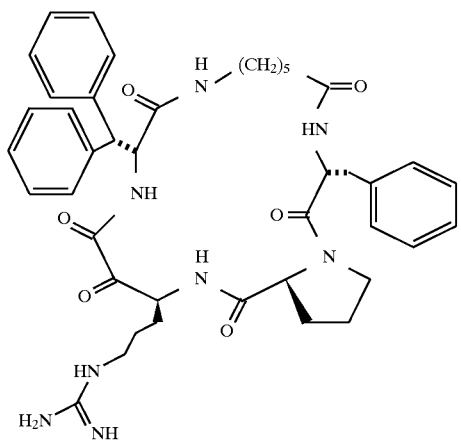

5R,15R,19S,21 AS-N-[3-(15-BENZHYDRYL-5-BENZYL-4,7,14,17,18,21-HEXAOXODOCOSAHYDRO-3a,6,13,16,20-PENTMZACYCLOPENTACYCLOEICOSEN-19-YL)PPROPYL]GUANIDINE TRIFLUOROACETIC ACID

COMPOUND 19

Compound 19 was prepared using the method of Example 11 with the following modifications. 6-Aminohexanoic acid is used in place of 5-aminoheptanoic acid in step 11a and CBZ-D-Phe is replaced with CBZ-D-diPhe (prepared via the method of U.S. Pat. No. 5,198,548) in step 11b to give the title compound as a solid: FAB-MS m/z 766 (MH+); Anal. Calc'd for C$_{42}$H$_{52}$N$_8$O$_6$·1.75 C$_2$HF$_3$O$_2$·2.25 H$_2$O; Calc'd: C, 54.38; H, 5.84; N, 11.15; H$_2$O, 4.03; Found: C, 54.57; H, 5.71; N, 11.29; H$_2$O, 4.09.

EXAMPLE 20

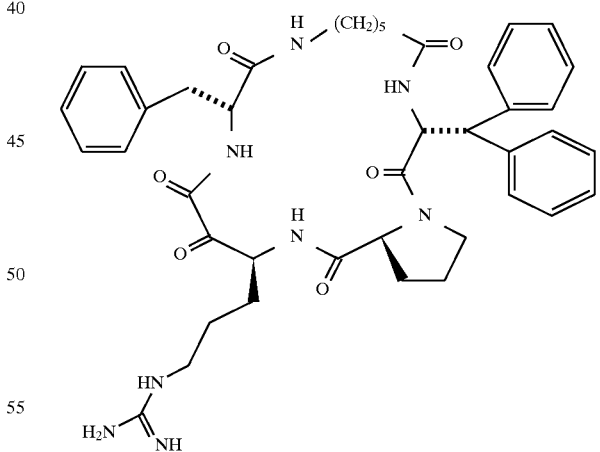

5R,15S,19S,21aS-N-[3-(5,15-DIBENZYL-4,7,14,17,18,21-HEXAOXODOCOSAHYDRO-3a,6,13,16,20-PENTAAZACYCLOPENTACYCLOEICOSEN-19-YL)PROPYL]GUANIDINE TRIFLUOROACETIC ACID

COMPOUND 20

Compound 20 was prepared using the method of Example 11 with the following modifications. 6-Aminohexanoic acid is used in place of 5-aminoheptanoic acid in step 11a and CBZ-D-diPhe-ProO-t-Bu replaced with D-Phe-ProO-t-Bu in step 11d to give the title compound as a solid: FAB-MS m/z 766 (MH+); Anal. Calc'd for C$_{42}$H$_{52}$N$_8$O$_6$.2.0 C$_2$HF$_3$O$_2$.2.75 H$_2$O; Calc'd: C, 53.00; H, 5.75; N, 10.75; H$_2$O, 4.75; Found: C, 53.30; H, 5.51; N, 10.70; H$_2$O, 4.96.

EXAMPLE 21

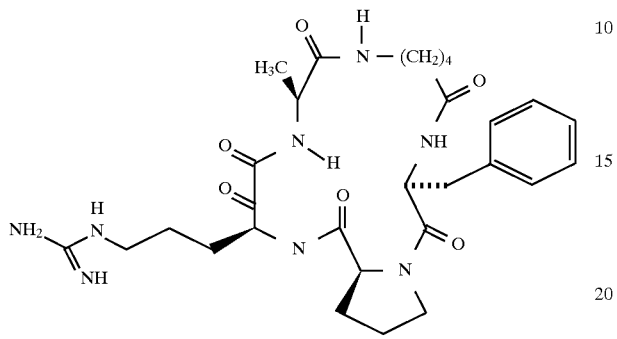

5R,14R,18S,20aS-N-[3-(5-BENZYL-14-METHYI-4,7,13,16,17,20-HEXAOXOEICOSAHYDRO-3a,6, 12,15,19-PENTAAZACYCLOPENTA-CYCLONONADECEN-18-YL)PROPYL] GUANIDINE TRIFLUOROACETIC ACID

COMPOUND 21

Compound 21 was prepared using the method of Example 11 with the following modifications. 6-Aminohexanoic acid is used in place of 5-aminoheptanoic acid in step 11a and CBZ-D-Phe is replaced with CBZ-D-Ala in step 11b to give the title compound as a solid: FAB-MS m/z 600 (MH+); Anal. Calc'd for C$_{29}$H$_{42}$N$_8$O$_6$.2.15 C$_2$HF$_3$O$_2$.2.50 H$_2$O; Calc'd: C, 45.00; H. 5.57; N, 12.16; H$_2$O, 5.07; Found: C, 45.01; H, 5.46; N, 12.82; H$_2$O, 5.31.

EXAMPLE 22

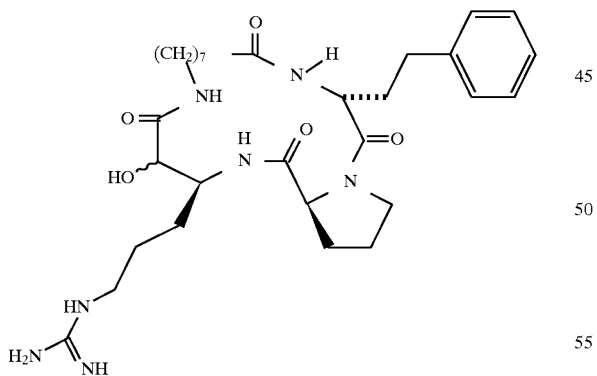

[20aR-(20aR, 5R, 18S)]-N-[3-(5-PHENYLETHYL-17-HYDROXY-4, 7, 16, 20-TETRAOXOEICOSAHYDRO-3a, 6, 15, 19-TETRA-AZACYCLONONADECANE-18-YL) PROPYIL] GUANIDINE

COMPOUND 22

A suspension of intermediate 1 h (0.245 g, 0.372 mmol) anisole (2 mL) was cooled to −78° C. and treated anhydrous HF (ca. 10 mL) using a standard HF apparatus. After stirring for 4 h, HF was removed under reduced pressure at 0° C., and the residue was triturated twice with 25 mL portions of ether. The solid was collected, washed with ether, then purified by reverse-phase HPLC (MeCN-water-TFA, 30:70:0.2). Lyophillization of the eluate provided the title compound as a white solid: FAB-MS m/z 586 (MH$^+$); Anal. Calcd for C$_{30}$H$_{47}$N$_7$O$_5$.2C$_2$HF3O$_2$.0.75 H$_2$O; Calc'd: C, 49.36; H, 6.15; N, 11.85; H2O, 1.63; Found: C, 49.10, H, 6.07; N, 12.15; H2O; 1.42.

EXAMPLE 23

Step a

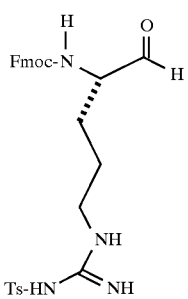

23a 1,1-Carbonyldiimidazole (1.8 g, 11.0 mmol) was added to a solution of N-α-Fmoc-N$^G$-tosyl-L-arginine (6.0 g, 10.0 mmol) in anhydrous THF (30 mL) at 0° C. under argon and stirred at 0° C. for 1.5 h. The reaction mixture was cooled to −48° C. and 1M DIBAL (28 mL, 28 mmol) was added dropwise over 20 min. The resulting mixture was stirred for another 1.5 h and 1.2N HCL (67 mL) was added with stirring. The mixture was allowed to warm up to room temperature and partitioned between 0.6N HCI (65 mL) and chloroform. The resulting aqueous layer was washed with several portions of chloroform. The combined organic extracts were washed with successive portions of water and brine, dried (Na$_2$SO$_4$) and concentrated in vacuo to afford the aldehyde 23a as a white flakey solid.

Step b

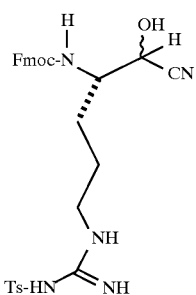

23b

A solution of KCN (1.44 g, 22 mmol) and H$_2$O (125 mL) was added to a solution of aldehyde 23a (5.9 g, 11.0 mmol) in ethyl acetate (250 mL) and the resulting mixture was stirred for 40 h at room temperature under argon. The organic layer was separated and the aqueous layer was washed with three portions of ethyl acetate. The combined ethyl acetate extracts were washed with brine, dried (Na$_2$SO$_4$), concentrated in vacuo and stored in the refrigerator under argon. The residue was partitioned between ethyl acetate (100 mL) and saturated aqueous NaHCO$_3$ (200 mL) and the pH was maintained at 7.0 by the addition of solid $NaHCO_3$. The solid $NaHCO_3$ was removed by filtration and the resulting aqueous layer was washed with several portions of ethyl acetate. The combined organic layer was washed twice with brine, dried ($MgSO_4$) and concentrated in vacuo to give the cyanohydrin 23b as a white solid; FAB-MS m/z562 (MH)+.

Step c

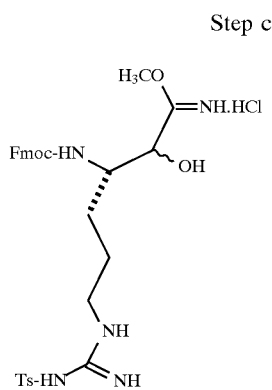

23c

HCl (21 g) was bubbled into a solution of nitrile 23b (3.0 g, 5.34 mmol) and methanol (53 mL) under argon at a temperature of less than −40° C. over 20 min. The reaction vessel was closed under nitrogen and placed in a freezer at −15° C. for 46 h and concentrated in vacuo at room temperature. The residue was partitioned between saturated aqueous $NaHCO_3$ solution (250 mL) and ethyl acetate. The organic layer was washed with two portions of brine, dried ($MgSO_4$) and concentrated in vacuo to give the imidate 23c as a solid.

Step d

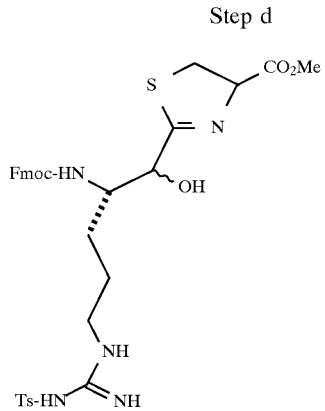

23d

Cysteine methyl ester hydrochloride (2.7 g, 15.9 mmol) was added to a solution of imidate 23c (5.0 g, 7.9 mmol) and $CH_2Cl_2$ (100 mL) and the resulting mixture was stirred under argon at room temperature for 2 d. The mixture was washed sequentially with brine and water, then dried ($Na_2SO_4$) and concentrated. The residue was purified by flash chromatography (silica gel, 95:5 $CH_2Cl_2$—MeOH) to give 3.8 g of 23d as a white foam: MS m/z 680 (MH+).

Step e

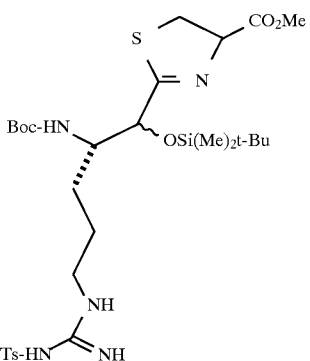

23e t-Butyldimethylsilyltriflate (3.3 g, 12.6 mmol) was added dropwise to a solution of 23d (1.9 g, 2.8 mmol) and 2,6-lutidine and cooled to 0° C. The mixture was stirred for 1 h at 0° C., then quenched with ice. The $CH_2Cl_2$ layer was washed with water, dried ($Na_2SO_4$) and concentrated to give the corresponding silyl ether which was used without purification: m/z 794 (MH+). The silyl ether was dissolved in 50 mL of 20% diethylamine —$CH_3CN$ and stirred for 2.5 h. The solution was concentrated, and the residue was purified via flash chromatography (silica gel, $CH_2Cl_2$→10% MeOH—$CH_2Cl_2$) to yield 1 g (1.85 mmol) of the corresponding a-amino derivative as an oil. This material (1.0 g, 1.85 mmol) was dissolved in $CH_2Cl_2$ (25 mL) and treated with di-t-butyl dicarbonate (0.49 g, 2.25 mmol) at 0° C. After stirring overnight at room temperature the reaction was washed with water and the $CH_2Cl_2$ layer was dried ($Na_2SO_4$) and concentrated. The residue was purified by flash chromatography (silica gel, 95:5 $CH_2Cl_2$—MeOH) to afford 1.1 g of 23e as a semi-solid: m/z 558 (MH+).

Step f

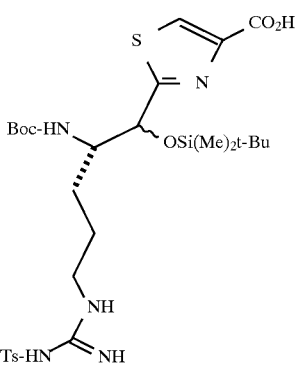

23f

Activated $MnO_2$ (3.5 g) was added to a solution of 23e (1.1 g, 1.7 mmol) in $CH_2Cl_2$ (100 mL). The mixture was stirred for 6.5 h and filtered through dicalite. The filtrate was concentrated, and the residue was purified by flash column chromatography (silica gel; 95:5 $CH_2Cl_2$—MeOH) to afford 800 mg (1.3 mmol) of the corresponding thiazole derivative as a white foam. The material was combined with LiOH (94 mg, 3.9 mmol) and 9:1 dioxane-water solution (12 mL). The mixture was stirred for 4 h, diluted with water and acidified to pH 5 with acetic acid. The mixture was extracted three times with ethyl acetate, dried ($Na_2SO_4$) and concentrated to give 23f as a white semi-solid: m/z 656 (MH+).

85

Step g

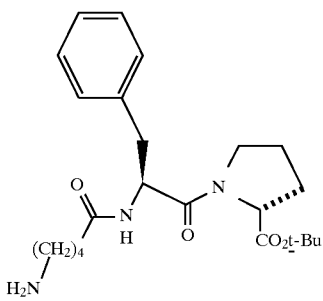

23g

Intermediate 23 g was prepared from D-Phe, ProO-t-Bu and 4-(N-carbobenzoxy)aminobutanoic acid, using steps a–d of Example 1.

Step h

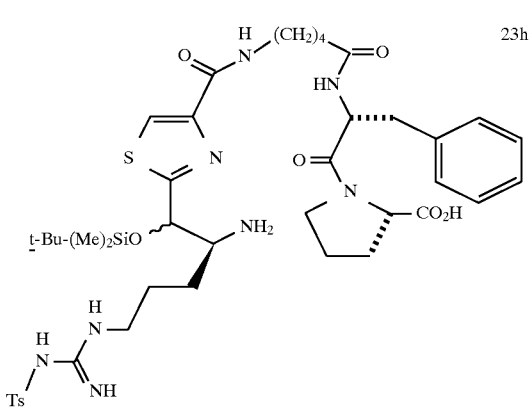

23h

A solution of intermediate 23f (0.4 g, 0.60 mmol), intermediate 23 g (0.26 g, 0.63 mmol), and HOBt (121 mg, 0.90 mmol) in $CH_3CN$ (10 mL) was treated with DCC (130 mg, 0.63 mmol) in $CH_3CN$ (2 mL). The mixture was stirred overnight, filtered and concentrated. The residue was dissolved in $CH_2Cl_2$, washed sequentially with saturated aqueous $NaHCO_3$, dried ($Na_2SO_4$) and concentrated. The residue was purified via flash column chromatography (silica gel, 95:5 $CH_2Cl_2$—MeOH) to afford 350 mg of the coupled product as a white foam: m/z 1055 (MH+). The material was dissolved in $CH_2Cl_2$ (10 mL) and treated with a solution of 1:1 TFA—$CH_2Cl_2$ (10 mL) at 0° C. The mixture was stirred for 1 h at room temperature and concentrated under a stream of $N_2$ at room temperature. The residue was triturated with ether to give 413 mg of intermediate 23 h as a white solid: MS m/z 899 (MH+).

86

Step i

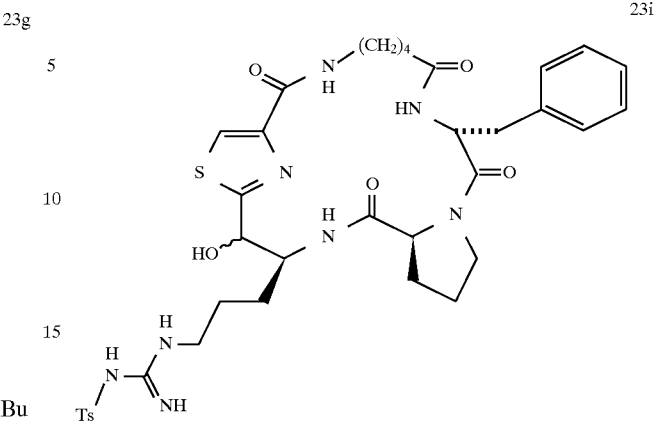

23i

A solution of intermediate 23 h (1.0 g, 0.90 mmol) in $CH_2Cl_2$ (900 mL) was treated with DMAP (560 mg, 4.6 mmol) followed by BOP-Cl (450 mg, 1.8 mmol). The mixture was stirred for 2 h and concentrated in vacuo. The residue was purified via flash column chromatography (silica gel, 95:5 $CH_2Cl_2$—MeOH) to give 500 mg of an off-white solid: m/z 882 (MH+). This solid was stirred for 1 h in 1M $Bu_4NF/THF$ and concentrated under reduced pressure. The residue dissolved in $CH_2Cl_2$ and washed repeatedly with $H_2O$. The organic layer was dried ($Na_2SO_4$) and concentrated under reduced pressure to yield 275 mg of the corresponding alcohol 23i which was used in the following step without further purification: m/z 767 (MH+).

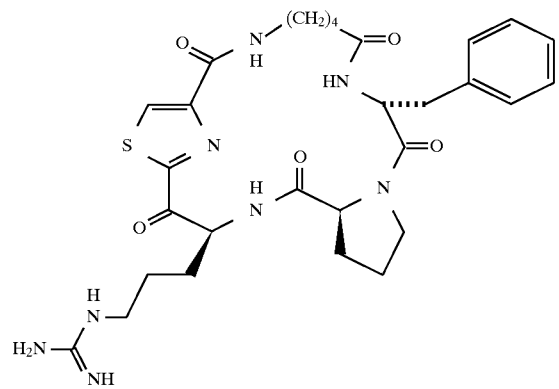

3S,6S,12R-N-[3-(12-BENZYL-2,5,11,14,20-PENTAOXO-23-THIA-4,10,13,19,24-PENTAAZATRICYCLO[19.2.1.3]-6,10-TETRACOSA-1(2H), 21-DIEN-3-YL)PROPYL] GUANIDINE

COMPOUND 23

The alcohol (275 mg) was suspended in 30 mL of $CH_2Cl_2$ and added to a suspension of the Dess-Martin periodinane (228 mg, 0.54 mmol) in 1 mL of $CH_2Cl_2$. The mixture was stirred for 3 h, quenched with 25% $Na_2S_2O_3$ (aq) in $NaHCO_3$ (sat'd., aq.) and stirred for 0.5 h. The layers were separated, and the $CH_2Cl_2$ layer was washed twice with water, dried ($Na_2SO_4$) and concentrated under reduced pressure to yield 273 mg of the corresponding keto-amide derivative as a foam: m/z 611 (MH+). A mixture of 270 mg of the keto-amide derivative was suspended in 2 mL of anisole and treated with excess (ca. 10 mL) anhydrous HF at −78° C. The mixture was stirred at 0° C. for 4.5 h, then HF was removed at 0° C. under reduced pressure. The residue was triturated with ether and purified by reverse-phase HPLC (70:30:0.2 $H_2O$—$CH_3CN$—TFA). Lyophillization of the eluate provided 120 mg of the title compound as a white solid: FAB-MS m/z 556 (MH$^+$); Anal. Calc'd for $C_{29}H_{38}N_8O_5S.1.75C_2HF_3O_2.1.5 H_2O$; Calc'd: C, 46.62; H, 5.15; N, 13.38, $H_2O$, 3.23; Found: C, 46.40; H, 5.03; N, 13.57; $H_2O$; 3.33.

What is claimed is:

1. A compound of the Formula I

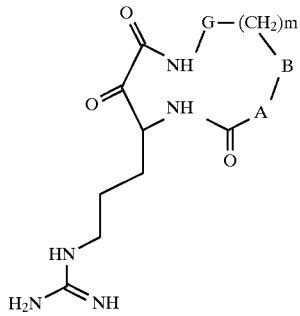

wherein:

m is 2 to 12;

A is

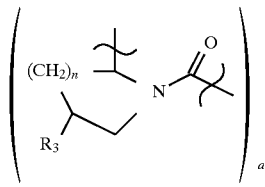

where the amido carbonyl is bound to B and the α aminomethine is bound to the depicted ring carbonyl, $R_3$ is hydrogen, hydroxy or $C_{1-5}$alkoxy, n is 1 or 2, and a is 0 or 1;

B is

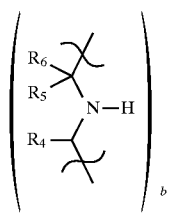

where the amido carbonyl of B is bound to the depicted ring methylene and the methine is bound to A, $R_4$ is independently selected from the group consisting of hydrogen, $C_{1-5}$alkyl, carboxy$C_{1-5}$alkyl, phenyl, substituted phenyl (where the phenyl substituents are $C_{1-5}$alkyl, carboxy $C_{1-5}$alkoxycarbonyl, carboxamido, amino, $C_{1-5}$alkylamino, hydroxy, $C_{1-5}$alkylcarbonylamino, $C_{1-5}$alkoxy, fluorine bromine or chlorine), phenyl$C_{1-5}$alkyl, substituted phenyl$C_{1-5}$alkyl (where the phenyl substituents are $C_{1-5}$alkyl, carboxy $C_{1-5}$alkoxycarbonyl, carboxamido, amino, $C_{1-5}$alkylamino, hydroxy, $C_{1-5}$alkylcarbonylamino, $C_{1-5}$alkoxy, fluorine bromine or chlorine), 3-pyridyl$C_{1-5}$alkyl, 4-pyridyl$C_{1-5}$salkyl, diphenyl$C_{1-2}$alkyl, and naphthyl, substituted naphthyl (where the naphthyl substituents are $C_{1-5}$alkyl, carboxy $C_{1-5}$alkoxycarbonyl, carboxamido, amino, $C_{1-5}$alkylamino, hydroxy, $C_{1-5}$alkylcarbonylamino, $C_{1-5}$alkoxy, fluorine bromine or chlorine), $R_5$ and $R_6$ are hydrogen or taken together with the carbon of attachment to form a carbonyl, and b is 0 or 1;

G is

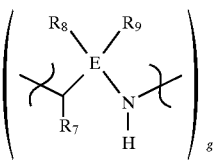

where the amine of G is bound to the ring methylene and the methine is bound to the depicted amide, $R_7$ is independently selected from the group consisting of hydrogen, $C_{1-5}$alkyl, carboxy$C_{1-5}$alkyl, phenyl, substituted phenyl (where the phenyl substituents are $C_{1-5}$alkyl, carboxy $C_{1-5}$alkoxycarbonyl, carboxamido, amino, $C_{1-5}$alkylamino, hydroxy, $C_{1-5}$alkylcarbonylamino, $C_{1-5}$alkoxy, fluorine bromine or chlorine), phenyl$C_{1-5}$alkyl, substituted phenyl$C_{1-5}$alkyl (where the phenyl substituents are $C_{1-5}$alkyl, carboxy $C_{1-5}$alkoxycarbonyl, carboxamido, amino, $C_{1-5}$alkylamino, hydroxy, $C_{1-5}$alkylcarbonylamino, $C_{1-5}$alkoxy, fluorine bromine or chlorine), 3-pyridylCl 5alkyl, 4-pyridyl$C_{1-5}$alkyl, diphenyl$C_{1-2}$alkyl, and naphthyl, substituted naphthyl (where the naphthyl substituents are $C_{1-5}$alkyl, carboxy $C_{1-5}$alkoxycarbonyl, carboxamido, amino, $C_{1-5}$alkylamino, hydroxy, $C_{1-5}$alkylcarbonylamino, $C_{1-5}$alkoxy, fluorine bromine or chlorine), E is carbon or $C(CH_2)_q$—, where q is 0 to 12, $R_8$ and $R_9$ are hydrogen or taken together with the carbon of E to form a carbonyl, and g is 0 or 1;

or the pharmaceutically acceptable salt thereof.

2. The compound of claim 1 where a is 1, b is 0 and g is 0.

3. The compound of claim 2 where n is 1.

4. The compound of claim 1 where a is 0, b is 1 and g is 0.

5. The compound of claim 4 where $R_5$ and $R_6$ are taken together with the carbon to which each is attached to form a carbonyl, and $R_4$ is selected form the group consisting of phenyl, substituted phenyl (where the phenyl substituents are $C_{1-5}$alkyl, carboxy $C_{1-5}$alkoxycarbonyl, carboxamido, amino, $C_{1-5}$alkylamino, hydroxy, $C_{1-5}$alkylcarbonylamino, $C_{1-5}$alkoxy, fluorine bromine or chlorine), phenyl$C_{1-5}$alkyl, substituted phenyl$C_{1-5}$ alkyl (where the phenyl substituents are $C_{1-5}$alkyl, carboxy $C_{1-5}$alkoxycarbonyl, carboxamido, amino, $C_{1-5}$alkylamino, hydroxy, $C_{1-5}$alkylcarbonylamino, $C_{1-5}$alkoxy, fluorine bromine or chlorine), diphenyl$C_{1-2}$alkyl, naphthyl and substituted naphthyl (where the aryl substituents are $C_{1-5}$alkyl, carboxy $C_{1-5}$alkoxycarbonyl, carboxamido, amino, $C_{1-5}$alkylamino, hydroxy, $C_{1-5}$alkylcarbonylamino, $C_{1-5}$alkoxy, fluorine bromine or chlorine).

6. The compound of claim 1 where a is 0, b is 0 and g is 1.

7. The compound of claim 6 where E is carbon, $R_8$ and $R_9$ are taken with the carbon of attachment for form a carbonyl, and $R_7$ is selected form the group consisting of phenyl, substituted phenyl (where the phenyl substituents are $C_{1-5}$alkyl, carboxy $C_{1-5}$alkoxycarbonyl, carboxamido, amino, $C_{1-5}$alkylamino, hydroxy, $C_{1-5}$alkylcarbonylamino, $C_{1-5}$alkoxy, fluorine bromine or chlorine), phenyl$C_{1-5}$alkyl, substituted phenyl$C_{1-5}$alkyl (where the phenyl substituents are $C_{1-5}$alkyl, carboxy $C_{1-5}$alkoxycarbonyl, carboxamido, amino, $C_{1-5}$alkylamino, hydroxy, $C_{1-5}$alkylcarbonylamino, $C_{1-5}$alkoxy, fluorine bromine or chlorine), diphenyl$C_{1-2}$alkyl, naphthyl and substituted naphthyl (where the aryl substituents are $C_{1-5}$alkyl, carboxy $C_{1-5}$alkoxycarbonyl, carboxamido, amino, $C_{1-5}$alkylamino, hydroxy, $C_{1-5}$alkylcarbonylamino, $C_{1-5}$alkoxy, fluorine bromine or chlorine).

8. The compound of claim 6 where $R_8$ and $R_9$ are hydrogen, E is $C(CH_2)_q$ and q is 0–6.

9. The compound of claim 1 where a is 1, b is 1 and g is 0.

10. The compound of claim 9 where n is 1, $R_5$ and $R_6$ are taken together with the carbon of attachment to form a carbonyl, and $R_4$ is selected form the group consisting of phenyl, substituted phenyl (where the phenyl substituents are $C_{1-5}$alkyl, carboxy $C_{1-5}$alkoxycarbonyl, carboxamido, amino, $C_{1-5}$alkylamino, hydroxy, $C_{1-5}$alkylcarbonylamino, $C_{1-5}$alkoxy, fluorine bromine or chlorine), phenyl$C_{1-5}$alkyl, substituted phenyl$C_{1-5}$alkyl (where the phenyl substituents are $C_{1-5}$alkyl, carboxy $C_{1-5}$alkoxycarbonyl, carboxamido, amino, $C_{1-5}$alkylamino, hydroxy, $C_{1-5}$alkylcarbonylamino, $C_{1-5}$alkoxy, fluorine bromine or chlorine), diphenyl$C_{1-2}$alkyl, naphthyl and substituted naphthyl (where the aryl substituents are $C_{1-5}$alkyl, carboxy $C_{1-5}$alkoxycarbonyl, carboxamido, amino, $C_{1-5}$alkylamino, hydroxy, $C_{1-5}$alkylcarbonylamino, $C_{1-5}$alkoxy, fluorine bromine or chlorine).

11. The compound of claim 1 where a is 1, b is 1 and g is 1.

12. The compound of claim 11 where n is 1, $R_5$ and $R_6$ are taken together with the carbon of attachment to form a carbonyl, and $R_4$ is selected form the group consisting of phenyl, substituted phenyl (where the phenyl substituents are $C_{1-5}$alkyl, carboxy $C_{1-5}$alkoxycarbonyl, carboxamido, amino, $C_{1-5}$alkylamino, hydroxy, C1-5alkylcarbonylamino, $C_{1-5}$alkoxy, fluorine bromine or chlorine), phenyl$C_{1-5}$alkyl, substituted phenyl$C_{1-5}$alkyl (where the phenyl substituents are $C_{1-5}$alkyl, carboxy $C_{1-5}$alkoxycarbonyl, carboxamido, amino, $C_{1-5}$alkylamino, hydroxy, $C_{1-5}$alkylcarbonylamino, $C_{1-5}$alkoxy, fluorine bromine or chlorine), diphenyl$C_{1-2}$alkyl, naphthyl and substituted naphthyl (where the aryl substituents are $C_{1-5}$alkyl, carboxy $C_{1-5}$alkoxycarbonyl, carboxamido, amino, $C_{1-5}$alkylamino, hydroxy, $C_{1-5}$alkylcarbonylamino, $C_{1-5}$alkoxy, fluorine bromine or chlorine), E is carbon, $R_8$ and $R_9$ are taken with the carbon of attachment for form a carbonyl, and $R_7$ is selected form the group consisting of phenyl, substituted phenyl (where the phenyl substituents are $C_{1-5}$salkyl, carboxy $C_{1-5}$alkoxycarbonyl, carboxamido, amino, $C_{1-5}$alkylamino, hydroxy, $C_{1-5}$alkylcarbonylamino, $C_{1-5}$alkoxy, fluorine bromine or chlorine), phenyl$C_{1-5}$alkyl, substituted phenyl$C_{1-5}$alkyl (where the phenyl substituents are $C_{1-5}$alkyl, carboxy $C_{1-5}$alkoxycarbonyl, carboxamido, amino, $C_{1-5}$alkylamino, hydroxy, $C_{1-5}$alkylcarbonylamino, $C_{1-5}$alkoxy, fluorine bromine or chlorine), diphenyl$C_{1-2}$alkyl, naphthyl and substituted naphthyl (where the aryl substituents; are $C_{1-5}$salkyl, carboxy $C_{1-5}$alkoxycarbonyl, carboxamido, amino, $C_{1-5}$alkylamino, hydroxy, $C_{1-5}$alkylcarbonylamino, $C_{1-5}$alkoxy, fluorine bromine or chlorine).

13. The compound of claim 11 where n is 1, $R_5$ and $R_6$ are taken together with the carbon of attachment to form a carbonyl, and $R_4$ is selected form the group consisting of phenyl, substituted phenyl (where the phenyl substituents are $C_{1-5}$alkyl, carboxy $C_{1-5}$alkoxycarbonyl, carboxamido, amino, $C_{1-5}$alkylamino, hydroxy, $C_{1-5}$alkylcarbonylamino, $C_{1-5}$alkoxy, fluorine bromine or chlorine), phenyl$C_{1-5}$alkyl, substituted phenyl$C_{1-5}$alkyl (where the phenyl substituents are $C_{1-5}$alkyl, carboxy $C_{1-5}$alkoxycarbonyl, carboxamido, amino, $C_{1-5}$alkylamino, hydroxy, $C_{1-5}$alkylcarbonylamino, $C_{1-5}$alkoxy, fluorine bromine or chlorine), diphenyl$C_{1-2}$alkyl, naphthyl and substituted naphthyl (where the aryl substituents are $C_{1-5}$alkyl, carboxy $C_{1-5}$alkoxycarbonyl, carboxamido, amino, $C_{1-5}$alkylamino, hydroxy, $C_{1-5}$alkylcarbonylamino, $C_{1-5}$alkoxy, fluorine bromine or chlorine), $R_8$ and $R_9$ are hydrogen, E is $C(CH_2)_q$, and q is 0–6.

14. The compound of claim 1 where a is 1, b is 0 and g is 1.

15. The compound of claim 14 where n is 1, E is carbon, $R_8$ and $R_9$ are taken with the carbon of attachment for form a carbonyl, and $R_7$ is selected form the group consisting of phenyl, substituted phenyl (where the phenyl substituents are $C_{1-5}$alkyl, carboxy $C_{1-5}$alkoxycarbonyl, carboxamido, amino, $C_{1-5}$alkylamino, hydroxy, $C_{1-5}$alkylcarbonylamino, $C_{1-5}$alkoxy, fluorine bromine or chlorine), phenyl$C_{1-5}$alkyl, substituted phenyl$C_{1-5}$alkyl (where the phenyl substituents are $C_{1-5}$alkyl, carboxy $C_{1-5}$alkoxycarbonyl, carboxamido, amino, $C_{1-5}$alkylamino, hydroxy, $C_{1-5}$alkylcarbonylamino, $C_{1-5}$alkoxy, fluorine bromine or chlorine), diphenyl$C_{1-2}$alkyl, naphthyl and substituted naphthyl (where the aryl substituents are $C_{1-5}$alkyl, carboxy $C_{1-5}$alkoxycarbonyl, carboxamido, amino, $C_{1-5}$alkylamino, hydroxy, $C_{1-5}$alkylcarbonylamino, $C_{1-5}$alkoxy, fluorine bromine or chlorine).

16. The compound of claim 14 where n is 1, $R_8$ and $R_9$ are hydrogen, E is $C(CH_2)_q$ and q is 0–6.

17. The compound of claim 1 where a is 0, b is 1 and g is 1.

18. The compound of claim 17 where $R_5$ and $R_6$ are taken together with the carbon of attachment to form a carbonyl, and $R_4$ is selected form the group consisting of phenyl, substituted phenyl (where the phenyl substituents are $C_{1-5}$alkyl, carlboxy $C_{1-5}$alkoxycarbonyl, carboxamido, amino, $C_{1-5}$alkylamino, hydroxy, $C_{1-5}$alkylcarbonylamino, $C_{1-5}$alkoxy, fluorine bromine or chlorine), phenyl$C_{1-5}$alkyl, substituted phenyl$C_{1-5}$ alkyl (where the phenyl substituents are $C_{1-5}$alkyl, carboxy $C_{1-5}$alkoxycarbonyl, carboxamido, amino, $C_{1-5}$alkylamino, hydroxy, $C_{1-5}$alkylcarbonylamino, $C_{1-5}$alkoxy, fluorine bromine or chlorine), diphenyl$C_{1-2}$ alkyl, naphthyl and substituted naphthyl (where the aryl substituents are $C_{1-5}$alkyl, carboxy $C_{1-5}$alkoxycarbonyl, carboxamido, amino, $C_{1-5}$alkylamino, hydroxy, $C_{1-5}$alkylcarbonylamino, $C_{1-5}$alkoxy, fluorine bromine or chlorine);

E is carbon, $R_8$ and $R_9$ are taken with the carbon of attachment for form a carbonyl, and $R_7$ is selected form the group consisting of phenyl, substituted phenyl (where the phenyl substituents are $C_{1-5}$alkyl, carboxy $C_{1-5}$alkoxycarbonyl, carboxamido, amino, $C_{1-5}$alkylamino, hydroxy, $C_{1-5}$alkylcarbonylamino, $C_{1-5}$alkoxy, fluorine bromine or chlorine), phenyl$C_{1-5}$alkyl, substituted phenyl$C_{1-5}$ alkyl (where the phenyl substituents are $C_{1-5}$alkyl, carboxy $C_{1-5}$alkoxycarbonyl, carboxamido, amino, $C_{1-5}$alkylamino, hydroxy, $C_{1-5}$alkylcarbonylamino, $C_{1-5}$alkoxy, fluorine bromine or chlorine), diphenyl$C_{1-2}$ alkyl, naphthyl and substituted naphthyl (where the aryl substituents are $C_{1-5}$alkyl, carboxy $C_{1-5}$alkoxycarbonyl, carboxamido, amino, $C_{1-5}$alkylamino, hydroxy, $C_{1-5}$alkylcarbonylamino, $C_{1-5}$alkoxy, fluorine bromine or chlorine).

19. The compound of claim 11 where $R_5$ and $R_6$ are taken together with the carbon of attachment to form a carbonyl, and $R_4$ is selected form the group consisting of phenyl, substituted phenyl (where the phenyl substituents are $C_{1-5}$alkyl, carboxy $C_{1-5}$alkoxycarbonyl, carboxamido, amino, $C_{1-5}$alkylamino, hydroxy, $C_{1-5}$alkylcarbonylamino, $C_{1-5}$alkoxy, fluorine bromine or chlorine), phenyl$C_{1-5}$alkyl, substituted phenyl$C_{1-5}$ alkyl (where the phenyl substituents are $C_{1-5}$alkyl, carboxy $C_{1-5}$alkoxycarbonyl, carboxamido, amino, $C_{1-5}$alkylamino, hydroxy, $C_{1-5}$alkylcarbonylamino, $C_{1-5}$alkoxy, fluorine bromine or chlorine), diphenyl$C_{1-2}$ alkyl, naphthyl and substituted naphthyl (where the aryl substituents are $C_{1-5}$alkyl, carboxy $C_{1-5}$alkoxycarbonyl, carboxamido, amino, $C_{1-5}$alkylamino, hydroxy, $C_{1-5}$alkylcarbonylamino, $C_{1-5}$alkoxy, fluorine bromine or chlorine)

$R_8$ and $R_9$ are hydrogen,

E is $C(CH_2)_q$, and q is 0–6.

20. The compounds of claim 1 selected from the group consisting of

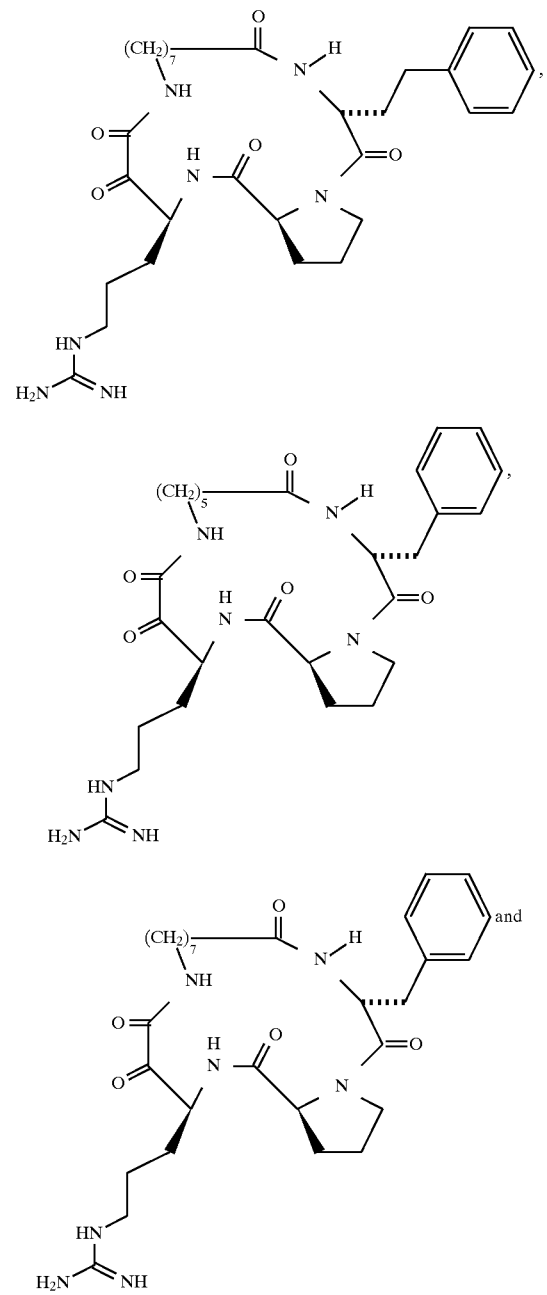

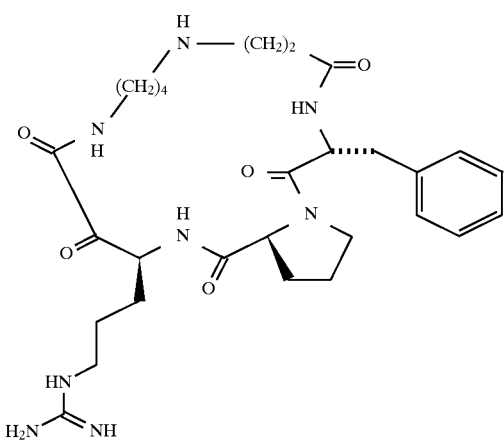
21. The compounds of claim 1 selected from the group consisting of
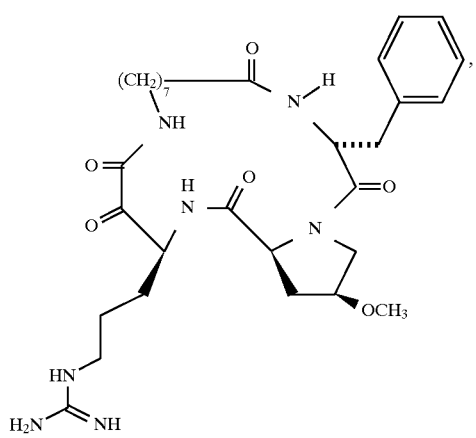
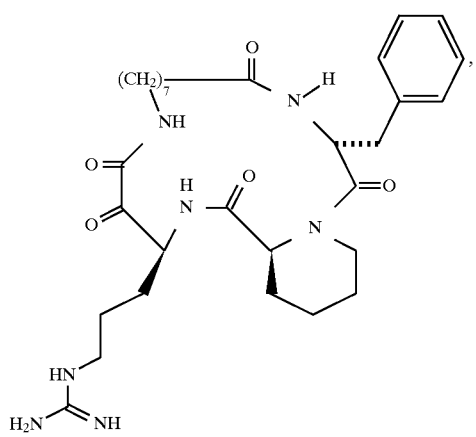
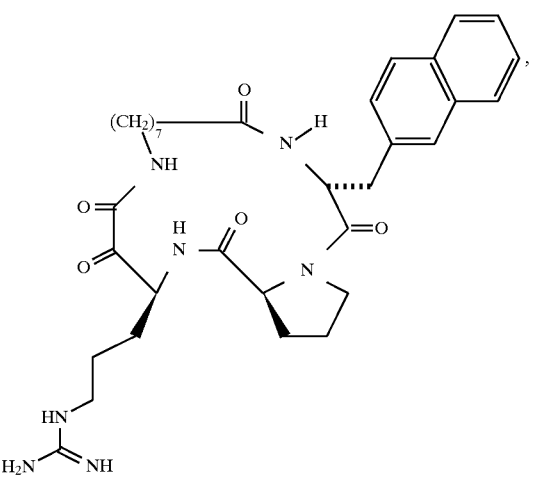
and
22. The compounds of claim 1 selected from the group consisting of 95
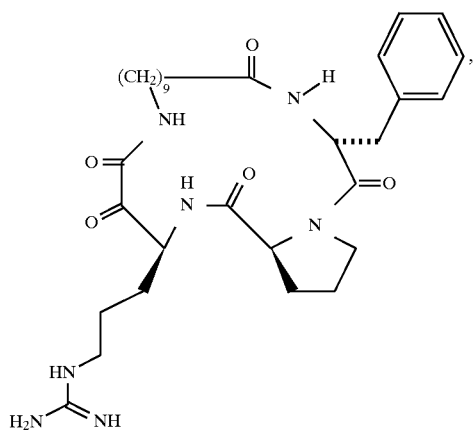
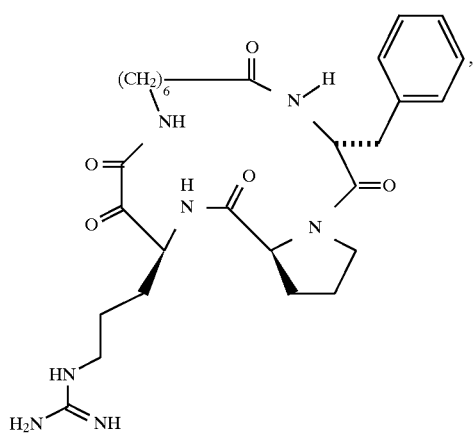
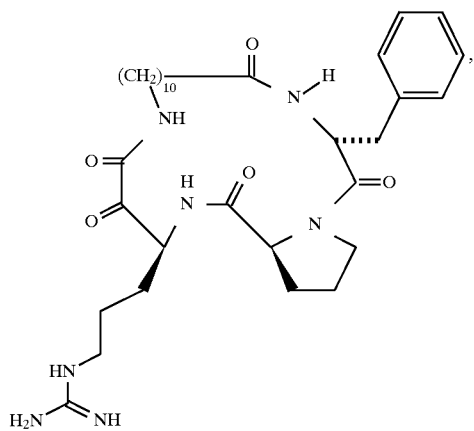
96
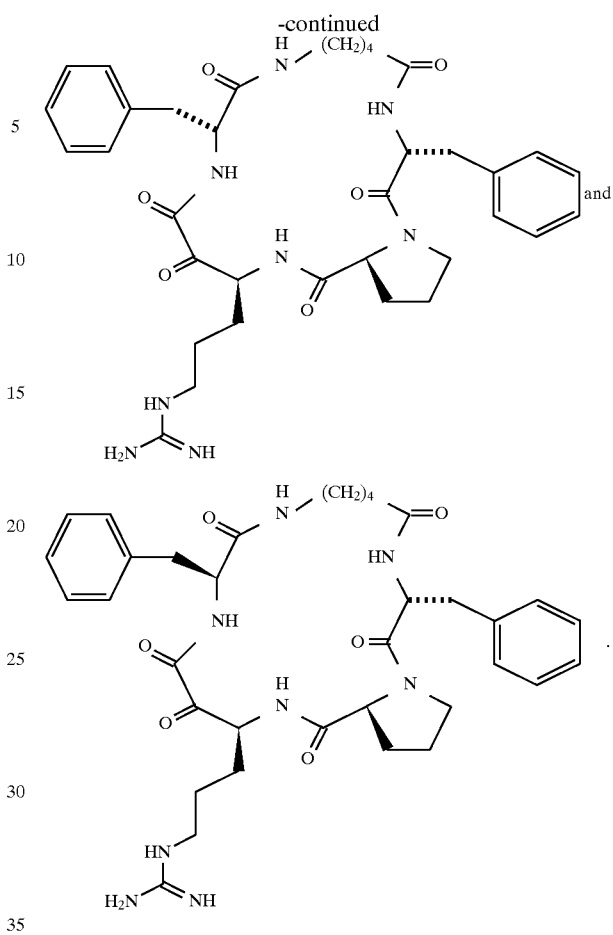
23. The compounds of claim 1 selected from the group consisting of
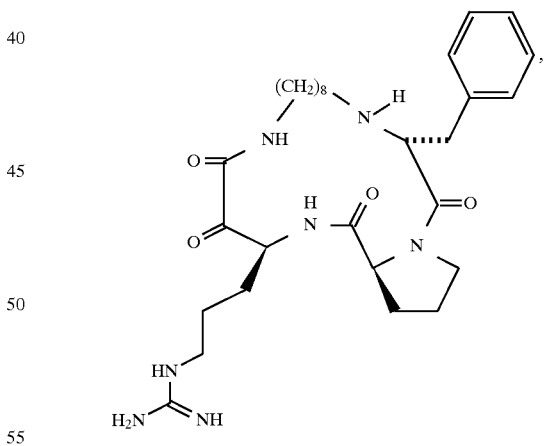

-continued
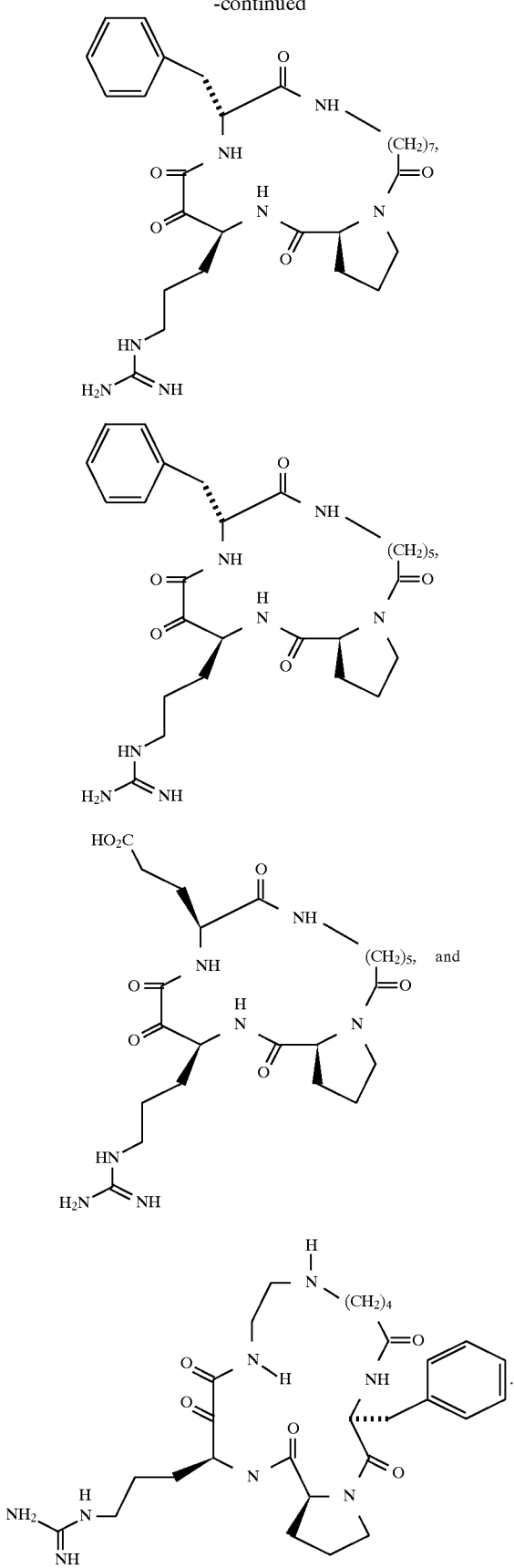
24. The compounds of claim 1 selected from the group consisting of
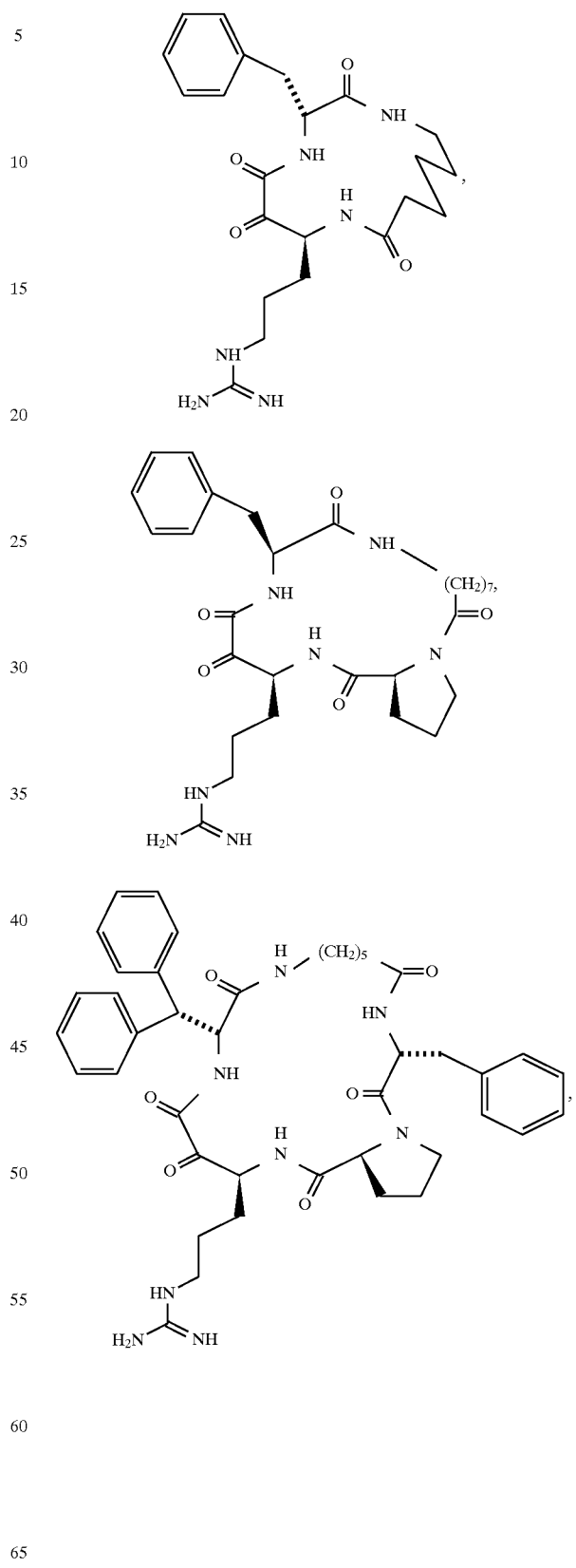

-continued

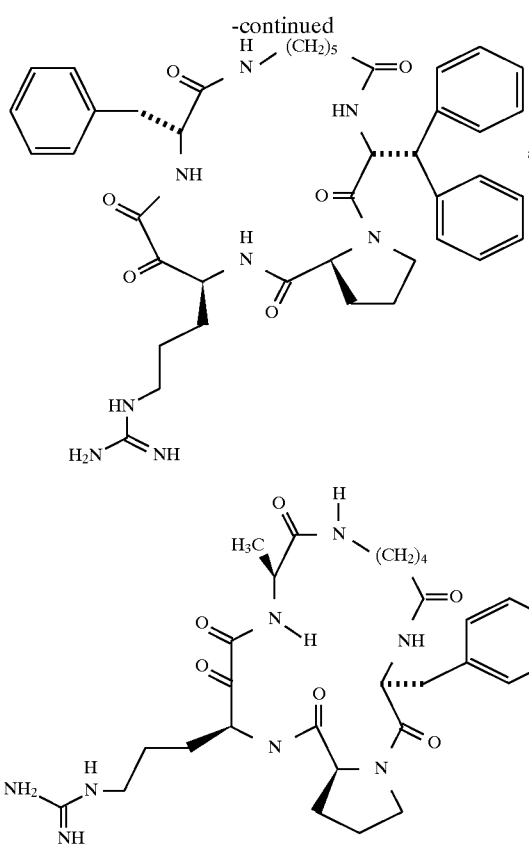

and

25. A compound of the Formula II

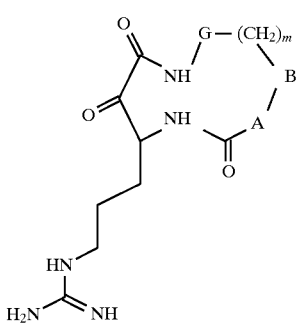
II wherein:
R₁ is hydroxy;
R₂ is hydrogen;
m is 2 to 12;
A is

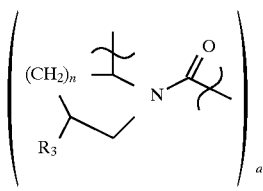

where the amido carbonyl is bound to B and the α aminomethine is bound to the depicted ring carbonyl,
R₃ is hydrogen or C₁₋₅alkoxy,
n is 1 or 2, and
a is 0 or 1;

B is

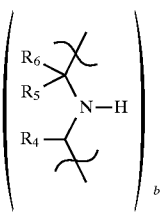

where the amido carbonyl of B is bound to the depicted ring methylenes and the methine is bound to A,
R₄ is independently selected from the group consisting of hydrogen, C₁₋₅alkyl, carboxyC₁₋₅alkyl, phenyl, substituted phenyl (where the phenyl substituents are C₁₋₅alkyl, carboxy C₁₋₅alkoxycarbonyl, carboxamido, amino, C₁₋₅alkylamino, hydroxy, C₁₋₅alkylcarbonylamino, C₁₋₅alkoxy, fluorine bromine or chlorine), phenylC₁₋₅alkyl, substituted phenylC₁₋₅alkyl (where the phenyl substituents are C₁₋₅alkyl, carboxy C₁₋₅alkoxycarbonyl, carboxamido, amino, C₁₋₅alkylamino, hydroxy, C₁₋₅alkylcarbonylamino, C₁₋₅alkoxy, fluorine bromine or chlorine), 3-pyridylC₁₋₅alkyl, 4-pyridylC₁₋₅alkyl, diphenylC₁₋₂alkyl, and naphthyl, substituted naphthyl (where the naphthyl substituents are C₁₋₅alkyl, carboxy C₁₋₅alkoxycarbonyl, carboxamido, amino, C₁₋₅alkylamino, hydroxy, C₁₋₅alkylcarbonylamino, C₁₋₅alkoxy, fluorine bromine or chlorine),
R₅ and R₆ are hydrogen or taken together with the carbon of attachment to form a carbonyl, and
b is 0 or 1;
G is

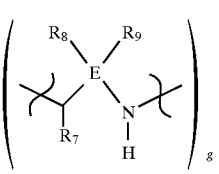

where the amine of G is bound to the ring methylenes and the methine is bound to the depicted amide,
R₇ is independently selected from the group consisting of hydrogen, C₁₋₅alkyl, carboxyC₁₋₅alkyl, phenyl, substituted phenyl (where the phenyl substituents are C₁₋₅alkyl, carboxy C₁₋₅alkoxycarbonyl, carboxamido, amino, C₁₋₅alkylamino, hydroxy, C₁₋₅alkylcarbonylamino, C₁₋₅alkoxy, fluorine bromine or chlorine), phenylC₁₋₅alkyl, substituted phenylC₁₋₅alkyl (where the phenyl substituents are C₁₋₅alkyl, carboxy C₁₋₅alkoxycarbonyl, carboxamido, amino, C₁₋₅alkylamino, hydroxy, C₁₋₅alkylcarbonylamino, C₁₋₅alkoxy, fluorine bromine or chlorine), 3-pyridylC₁₋₅alkyl, 4-pyridylC₁₋₅alkyl, diphenylC₁₋₂alkyl, and naphthyl, substituted naphthyl (where the naphthyl substituents are C₁₋₅alkyl, carboxy C₁₋₅alkoxycarbonyl, carboxamido, amino, C₁₋₅alkylamino, hydroxy, C₁₋₅alkylcarbonylamino, C₁₋₅alkoxy, fluorine bromine or chlorine),
E is carbon or C(CH₂)q—, where q is 0 to 12,
R₈ and R₉ are hydrogen or taken together with the carbon of E to form a carbonyl, and
g is 0 or 1;
and pharmaceutically acceptable salts thereof.

26. A compound of the Formula III,

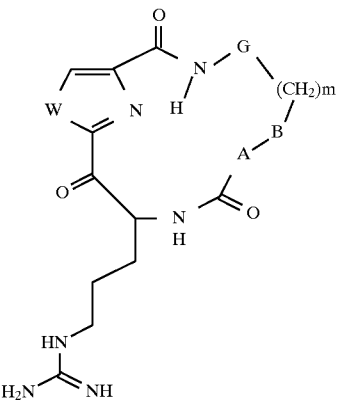

III wherein:
m is 2 to 12;
W is nitrogen, sulfur or oxygen;
A is

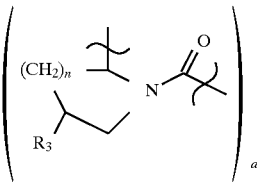

where the amido carbonyl is bound to B and the α aminomethine is bound to the depicted ring carbonyl,
$R_3$ is hydrogen, hydroxy or $C_{1-5}$alkoxy,
n is 1 or 2, and
a is 0 or 1;
B is

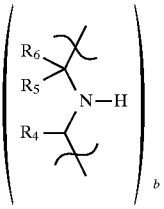

where the amido carbonyl of B is bound to the depicted ring methylene and the methine is bound to A,
$R_4$ is independently selected from the group consisting of hydrogen, $C_{1-5}$alkyl, carboxy$C_{1-5}$alkyl, phenyl, substituted phenyl (where the phenyl substituents are $C_{1-5}$alkyl, carboxy $C_{1-5}$alkoxycarbonyl, carboxamido, amino, $C_{1-5}$alkylamino, hydroxy, $C_{1-5}$alkylcarbonylamino, $C_{1-5}$alkoxy, fluorine bromine or chlorine), phenyl$C_{1-5}$alkyl, substituted phenyl$C_{1-5}$alkyl (where the phenyl substituents are $C_{1-5}$alkyl, carboxy $C_{1-5}$alkoxycarbonyl, carboxamido, amino, $C_{1-5}$alkylamino, hydroxy, $C_{1-5}$alkylcarbonylamino, $C_{1-5}$alkoxy, fluorine bromine or chlorine), 3-pyridyl$C_{1-5}$alkyl, 4-pyridyl$C_{1-5}$ alkyl, diphenyl$C_{1-2}$alkyl, and naphthyl, substituted naphthyl (where the naphthyl substituents are $C_{1-5}$alkyl, carboxy $C_{1-5}$alkoxycarbonyl, carboxamido, amino, $C_{1-5}$alkylamino, hydroxy, $C_{1-5}$alkylcarbonylamino, $C_{1-5}$alkoxy, fluorine bromine or chlorine);

$R_5$ and $R_6$ are hydrogen or taken together with the carbon of attachment to form a carbonyl, and
b is 0 or 1;
G is

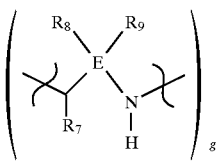

where the amine of G is bound to the ring methylene and the methine is bound to the depicted amide,
$R_7$ is independently selected from the group consisting of hydrogen, $C_{1-5}$alkyl, carboxy$C_{1-5}$alkyl, phenyl, substituted phenyl (where the phenyl substituents are $C_{1-5}$alkyl, carboxy $C_{1-5}$alkoxycarbonyl, carboxamido, amino, $C_{1-5}$alkylamino, hydroxy, $C_{1-5}$alkylcarbonylamino, $C_{1-5}$alkoxy, fluorine bromine or chlorine), phenyl$C_{1-5}$alkyl, substituted phenyl$C_{1-5}$alkyl (where the phenyl substituents are $C_{1-5}$allkyl, carboxy $C_{1-5}$alkoxycarbonyl, carboxamido, amino, $C_{1-5}$alkylamino, hydroxy, $C_{1-5}$alkylcarbonylamino, $C_{1-5}$alkoxy, fluorine bromine or chlorine), 3-pyridyl$C_{1-5}$alkyl, 4-pyridyl$C_{1-5}$ alkyl, diphenyl$C_{1-2}$alkyl, and naphthyl, substituted naphthyl (where the naphthyl substituents are $C_{1-5}$alkyl, carboxy $C_{1-5}$alkoxycarbonyl, carboxamido, amino, $C_{1-5}$alkylamino, hydroxy, $C_{1-5}$alkylcarbonylamino, $C_{1-5}$alkoxy, fluorine bromine or chlorine),
E is carbon or $C(CH_2)_q$—, where q is 0 to 12,
$R_8$ and $R_9$ are hydrogen or taken together with the carbon of E to form a carbonyl, and
g is 0 or 1;
and pharmaceutically acceptable salts thereof.

27. The compound of claim 26 where a is 1, b is 0 and g is 0.

28. The compound of claim 27 where n is 1.

29. The compound of claim 26 where a is 0, b is 1 and g is 0.

30. The compound of claim 29 where $R_5$ and $R_6$ are taken together with the carbon of attachment to form a carbonyl, and
$R_4$ is selected form the group consisting of phenyl, substituted phenyl (where the phenyl substituents are $C_{1-5}$alkyl, carboxy $C_{1-5}$alkoxycarbonyl, carboxamido, amino, $C_{1-5}$alkylamino, hydroxy, $C_{1-5}$alkylcarbonylamino, $C_{1-5}$alkoxy, fluorine bromine or chlorine), phenylClsalkyl, substituted phenyl$C_{1-5}$ alkyl (where the phenyl substituents are $C_{1-5}$alkyl, carboxy $C_{1-5}$alkoxycarbonyl, carboxamido, amino, $C_{1-5}$alkylamino, hydroxy, $C_{1-5}$alkylcarbonylamino, $C_{1-5}$alkoxy, fluorine bromine or chlorine), diphenyl$C_{1-2}$ alkyl, naphthyl and substituted naphthyl (where the aryl substituents are $C_{1-5}$alkyl, carboxy $C_{1-5}$alkoxycarbonyl, carboxamido, amino, $C_{1-5}$alkylamino, hydroxy, $C_{1-5}$alkylcarbonylamino, $C_{1-5}$alkoxy, fluorine bromine or chlorine).

31. The compound of claim 26 where a is 0, b is 0 and g is 1.

32. The compound of claim 31 where E is carbon, $R_8$ and $R_9$ are taken with the carbon of attachment for form a carbonyl, and
$R_7$ is selected form the group consisting of phenyl, substituted phenyl (where the phenyl substituents are $C_{1-5}$alkyl, carboxy $C_{1-5}$alkoxycarbonyl, carboxamido, amino, $C_{1-5}$alkylamino, hydroxy, $C_{1-5}$alkylcarbonylamino, $C_{1-5}$alkoxy, fluorine bromine or chlorine), phenyl$C_{1-5}$alkyl, substituted phenyl$C_{1-5}$alkyl (where the phenyl substituents are $C_{1-5}$alkyl, carboxy $C_{1-5}$alkoxycarbonyl, carboxamido, amino, $C_{1-5}$alkylamino, hydroxy, $C_{1-5}$alkylcarbonylamino, $C_{1-5}$alkoxy, fluorine bromine or chlorine), diphenyl$C_{1-2}$alkyl, naphthyl and substituted naphthyl (where the aryl substituents are $C_{1-5}$alkyl, carboxy $C_{1-5}$alkoxycarbonyl, carboxamido, amino, $C_{1-5}$alkylamino, hydroxy, $C_{1-5}$alkylcarbonylamino, $C_{1-5}$alkoxy, fluorine bromine or chlorine).

33. The compound of claim 31 where $R_8$ and $R_9$ are hydrogen, E is $C(CH_2)_q$ and q is 0–6.

34. The compound of claim 26 where a is 1, b is 1 and g is 0.

35. The compound of claim 34 where n is 1, $R_5$ and $R_6$ are taken together with the carbon of attachment to form a carbonyl, and $R_4$ is selected form the group consisting of phenyl, substituted phenyl (where the phenyl substituents are $C_{1-5}$alkyl, carboxy $C_{1-5}$alkoxycarbonyl, carboxamido, amino, $C_{1-5}$alkylamino, hydroxy, $C_{1-5}$alkylcarbonylamino, $C_{1-5}$alkoxy, fluorine bromine or chlorine), phenyl$C_{1-5}$alkyl, substituted phenyl$C_{1-5}$alkyl (where the phenyl substituents are $C_{1-5}$alkyl, carboxy $C_{1-5}$alkoxycarbonyl, carboxamido, amino, $C_{1-5}$alkylamino, hydroxy, $C_{1-5}$alkylcarbonylamino, $C_{1-5}$alkoxy, fluorine bromine or chlorine), diphenyl$C_{1-2}$alkyl, naphthyl and substituted naphthyl (where the aryl substituents are $C_{1-5}$alkyl, carboxy $C_{1-5}$alkoxycarbonyl, carboxamido, amino, $C_{1-5}$alkylamino, hydroxy, $C_{1-5}$alkylcarbonylamino, $C_{1-5}$alkoxy, fluorine bromine or chlorine).

36. The compound of claim 26 where a is 1, b is 1 and g is 1.

37. The compound of claim 36 where n is 1, $R_5$ and $R_6$ are taken together with the carbon of attachment to form a carbonyl, and $R_4$ is selected form the group consisting of phenyl, substituted phenyl (where the phenyl substituents are $C_{1-5}$alkyl, carboxy $C_{1-5}$alkoxycarbonyl, carboxamido, amino, $C_{1-5}$alkylamino, hydroxy, $C_{1-5}$alkylcarbonylamino, $C_{1-5}$alkoxy, fluorine bromine or chlorine), phenyl$C_{1-5}$alkyl, substituted phenyl$C_{1-5}$alkyl (where the phenyl substituents are $C_{1-5}$alkyl, carboxy $C_{1-5}$alkoxycarbonyl, carboxamido, amino, $C_{1-5}$alkylamino, hydroxy, $C_{1-5}$alkylcarbonylamino, $C_{1-5}$alkoxy, fluorine bromine or chlorine), diphenyl$C_{1-2}$alkyl, naphthyl and substituted naphthyl (where the aryl substituents are $C_{1-5}$alkyl, carboxy $C_{1-5}$alkoxycarbonyl, carboxamido, amino, $C_{1-5}$alkylamino, hydroxy, $C_{1-5}$alkylcarbonylamino, $C_{1-5}$alkoxy, fluorine bromine or chlorine), E is carbon, $R_8$ and $R_9$ are taken with the carbon of attachment for form a carbonyl, and $R_7$ is selected form the group consisting of phenyl, substituted phenyl (where the phenyl substituents are $C_{1-5}$alkyl, carboxy $C_{1-5}$alkoxycarbonyl, carboxamido, amino, $C_{1-5}$alkylamino, hydroxy, $C_{1-5}$alkylcarbonylamino, $C_{1-5}$alkoxy, fluorine bromine or chlorine), phenyl$C_{1-5}$alkyl, substituted phenyl$C_{1-5}$alkyl (where the phenyl substituents are $C_{1-5}$alkyl, carboxy $C_{1-5}$alkoxycarbonyl, carboxamido, amino, $C_{1-5}$alkylamino, hydroxy, $C_{1-5}$alkylcarbonylamino, $C_{1-5}$alkoxy, fluorine bromine or chlorine), diphenyl$C_{1-2}$alkyl, naphthyl and substituted naphthyl (where the aryl substituents are $C_{1-5}$alkyl, carboxy $C_{1-5}$alkoxycarbonyl, carboxamido, amino, $C_{1-2}$alkylamino, hydroxy, $C_{1-5}$alkylcarbonylamino, $C_{1-5}$alkoxy, fluorine bromine or chlorine).

38. The compound of claim 36 where n is 1, $R_5$ and $R_6$ are taken together with the carbon of attachment to form a carbonyl; and $R_4$ is selected form the group consisting of phenyl, substituted phenyl (where the phenyl substituents are $C_{1-5}$alkyl, carlboxy $C_{1-5}$alkoxycarbonyl, carboxamido, amino, $C_{1-5}$alkylamino, hydroxy, $C_{1-5}$alkylcarbonylamino, $C_{1-5}$alkoxy, fluorine bromine or chlorine), phenyl$C_{1-5}$alkyl, substituted phenyl$C_{1-5}$alkyl (where the phenyl substituents are $C_{1-5}$alkyl, carboxy $C_{1-5}$alkoxycarbonyl, carboxamido, amino, $C_{1-5}$alkylamino, hydroxy, $C_{1-5}$alkylcarbonylamino, $C_{1-5}$alkoxy, fluorine bromine or chlorine), diphenyl$C_{1-2}$alkyl, naphthyl and substituted naphthyl (where the aryl substituents are $C_{1-5}$alkyl, carboxy $C_{1-5}$alkoxycarbonyl, carboxamido, amino, $C_{1-5}$alkylamino, hydroxy, $C_{1-5}$alkylcarbonylamino, $C_{1-5}$alkoxy, fluorine bromine or chlorine), $R_8$ and $R_9$ are hydrogen, E is $C(CH_2)_q$, and q is 0–6.

39. The compound of claim 26 where a is 1, b is 0 and g is 1.

40. The compound of claim 39 where n is 1, E is carbon, $R_8$ and $R_9$ are taken with the carbon of attachment for form a carbonyl, and R7 is selected form the group consisting of phenyl, substituted phenyl (where the phenyl substituents are $C_{1-5}$alkyl, carboxy $C_{1-5}$alkoxycarbonyl, carboxamido, amino, $C_{1-5}$alkylamino, hydroxy, $C_{1-5}$alkylcarbonylamino, $C_{1-5}$alkoxy, fluorine bromine or chlorine), phenyl$C_{1-5}$alkyl, substituted phenyl$C_{1-5}$alkyl (where the phenyl substituents are $C_{1-5}$alkyl, carboxy $C_{1-5}$alkoxycarbonyl, carboxamido, amino, $C_{1-5}$alkylamino, hydroxy, $C_{1-5}$alkylcarbonylamino, $C_{1-5}$alkoxy, fluorine bromine or chlorine), diphenyl$C_{1-2}$alkyl, naphthyl and substituted naphthyl (where the aryl substituents are $C_{1-5}$alkyl, carboxy $C_{1-5}$alkoxycarbonyl, carboxamido, amino, $C_{1-5}$alkylamino, hydroxy, $C_{1-5}$alkylcarbonylamino, $C_{1-5}$alkoxy, fluorine bromine or chlorine).

41. The compound of claim 39 where n is 1, $R_8$ and $R_9$ are hydrogen, E is $C(CH_2)$q and q is 0–6.

42. The compound of claim 26 where a is 0, b is 1 and g is 1.

43. The compound of claim 42 where R5 and $R_6$ are taken together with the carbon of attachment to form a carbonyl, and $R_4$ is selected form the group consisting of phenyl, substituted phenyl (where the phenyl substituents are $C_{1-5}$alkyl, carboxy $C_{1-5}$alkoxycarbonyl, carboxamido, amino, $C_{1-5}$alkylamino, hydroxy, $C_{1-5}$alkylcarbonylamino, $C_{1-5}$alkoxy, fluorine bromine or chlorine), phenyl$C_{1-5}$alkyl, substituted phenyl$C_{1-5}$alkyl (where the phenyl substituents are $C_{1-5}$alkyl, carboxy $C_{1-5}$alkoxycarbonyl, carboxamido, amino, $C_{1-5}$alkylamino, hydroxy, $C_{1-5}$alkylcarbonylamino, $C_{1-5}$alkoxy, fluorine bromine or chlorine), diphenyl$C_{1-2}$alkyl, naphthyl and substituted naphthyl (where the aryl substituents are $C_{1-5}$alkyl, carboxy $C_{1-5}$alkoxycarbonyl, carboxamido, amino, $C_{1-5}$alkylamino, hydroxy, $C_{1-5}$alkylcarbonylamino, $C_{1-5}$alkoxy, fluorine bromine or chlorine), E is carbon, $R_8$ and $R_9$ are taken with the carbon of attachment for form a carbonyl, and $R_7$ is selected form the group consisting of phenyl, substituted phenyl (where the phenyl substituents are $C_{1-5}$alkyl, carboxy $C_{1-5}$alkoxycarbonyl, carboxamido, amino, $C_{1-5}$alkylamino, hydroxy, $C_{1-5}$alkylcarbonylamino, $C_{1-5}$alkoxy, fluorine bromine or chlorine), phenyl$C_{1-5}$alkyl, substituted phenyl$C_{1-5}$ alkyl (where the phenyl substituents are $C_{1-5}$alkyl, carboxy $C_{1-5}$alkoxycarbonyl, carboxamido, amino, $C_{1-5}$alkylamino, hydroxy, $C_{1-5}$alkylcarbonylamino, $C_{1-5}$alkoxy, fluorine bromine or chlorine), diphenyl$C_{1-2}$ alkyl, naphthyl and substituted naphthyl (where the aryl substituents are $C_{1-5}$alkyl, carboxy $C_{1-5}$alkoxycarbonyl, carboxamido, amino, $C_{1-5}$alkylamino, hydroxy, $C_{1-5}$alkylcarbonylamino, $C_{1-5}$alkoxy, fluorine bromine or chlorine).

44. The compound of claim 42 where $R_5$ and $R_6$ are taken together with the carbon of attachment to form a carbonyl and $R_4$ is selected form the group consisting of phenyl, substituted phenyl (where the phenyl substituents are $C_{1-5}$alkyl, carboxy $C_{1-5}$alkoxycarbonyl, carboxamido, amino, $C_{1-5}$alkylamino, hydroxy, $C_{1-5}$alkylcarbonylamino, $C_{1-5}$alkoxy, fluorine bromine or chlorine), phenyl$C_{1-5}$alkyl, substituted phenyl$C_{1-5}$ alkyl (where the phenyl substituents are $C_{1-5}$alkyl, carboxy $C_{1-5}$alkoxycarbonyl, carboxamido, amino, $C_{1-5}$alkylamino, hydroxy, $C_{1-5}$alkylcarbonylamino, $C_{1-5}$alkoxy, fluorine bromine or chlorine), diphenyl$C_{1-2}$ alkyl, naphthyl and substituted naphthyl (where the aryl substituents are $C_{1-5}$alkyl, carboxy $C_{1-5}$alkoxycarbonyl, carboxamido, amino, $C_{1-5}$alkylamino, hydroxy, $C_{1-5}$alkylcarbonylamino, $C_{1-5}$alkoxy, fluorine bromine or chlorine);

$R_8$ and $R_9$ are hydrogen, E is $C(CH_2)_q$ and q is 0–6.

45. The compounds of claim 26 selected from the group consisting of

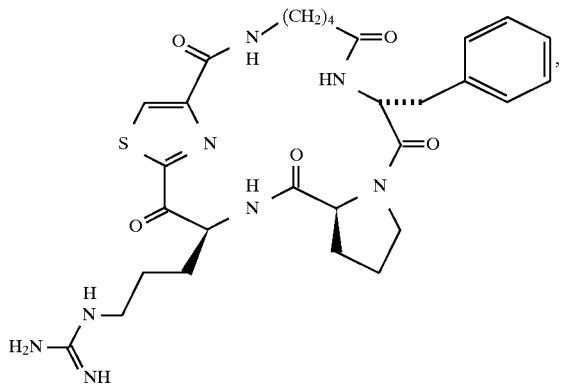

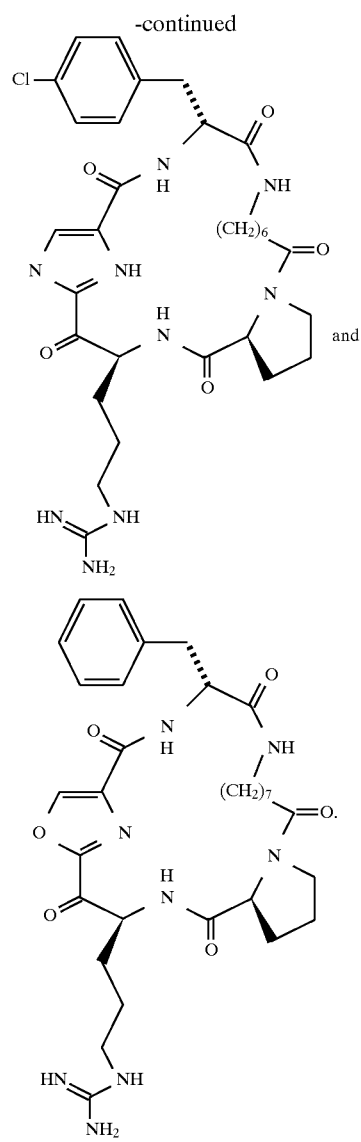

46. A pharmaceutical composition comprising a pharmaceutically acceptable carrier and an effective amount of a compound of claim 1 or of claim 26 for treating thrombin mediated diseases in a mammal.

47. A method for inhibiting thrombin comprising contacting a compound of claim 1 or of claim 26 with a medium containing thrombin.

48. The method of claim 47 where the compound contacts the medium via an orthopedic or a surgical device.

49. The method of claim 47 where the medium is manimailian blood.

50. A method of claim 49 where the mammal is a human.

51. A method treating a thrombin mediated disease in a mammal comprising administering an effective amount of a compound of claim 1 or of claim 26.

52. A method for inhibiting trypsin comprising contacting a compound of claim 1 or of claim 26 with a medium containing trypsin.

53. A method of treating a trypsin related disorder in a mammal comprising administering an effective amount of a compound of claim 1 or of claim 26.

* * * * *